(12) United States Patent
Gu et al.

(10) Patent No.: US 9,168,316 B2
(45) Date of Patent: *Oct. 27, 2015

(54) METHODS FOR TREATING OBESITY

(71) Applicants: Yansong Gu, Bellevue, WA (US); Hongzhe Li, Beaverton, OR (US)

(72) Inventors: Yansong Gu, Bellevue, WA (US); Hongzhe Li, Beaverton, OR (US)

(*) Notice: Subject to any disclaimer, the term of this patent is extended or adjusted under 35 U.S.C. 154(b) by 0 days.

This patent is subject to a terminal disclaimer.

(21) Appl. No.: 14/270,358

(22) Filed: May 6, 2014

(65) Prior Publication Data
US 2014/0322136 A1 Oct. 30, 2014

Related U.S. Application Data

(63) Continuation of application No. 13/123,703, filed as application No. PCT/US2009/060238 on Oct. 9, 2009, now Pat. No. 8,980,852.

(60) Provisional application No. 61/104,526, filed on Oct. 10, 2008.

(51) Int. Cl.
| | |
|---|---|
| *A61K 48/00* | (2006.01) |
| *C12N 15/113* | (2010.01) |
| *A61K 49/00* | (2006.01) |
| *A61K 31/352* | (2006.01) |
| *A61K 31/513* | (2006.01) |
| *A61K 31/465* | (2006.01) |
| *A61K 31/403* | (2006.01) |
| *A61K 31/4245* | (2006.01) |
| *A61K 31/166* | (2006.01) |
| *A61K 31/404* | (2006.01) |
| *C12N 9/80* | (2006.01) |
| *A61K 31/7105* | (2006.01) |
| *A61K 31/713* | (2006.01) |

(52) U.S. Cl.
CPC ............... *A61K 49/00* (2013.01); *A61K 31/166* (2013.01); *A61K 31/352* (2013.01); *A61K 31/403* (2013.01); *A61K 31/404* (2013.01); *A61K 31/4245* (2013.01); *A61K 31/465* (2013.01); *A61K 31/513* (2013.01); *A61K 31/713* (2013.01); *A61K 31/7105* (2013.01); *C12N 9/80* (2013.01); *C12Y 305/01098* (2013.01)

(58) Field of Classification Search
CPC . A61K 48/00; A61K 31/353; A61K 2300/00; A61K 31/00
See application file for complete search history.

(56) References Cited

U.S. PATENT DOCUMENTS 9,089,588 B2 * 7/2015 Collard .............. A61K 31/7088
1/1

* cited by examiner

*Primary Examiner* — Amy Bowman

(57) ABSTRACT

The present invention provides methods to reduce or inhibit weight gain by administering inhibitors of the SirT1 protein to a subject. Methods to identify such inhibitors are also disclosed.

18 Claims, 71 Drawing Sheets

| SYMBOL | DEFINITION | Mean WAT2 Control | Mean WAT2 KOKO | Fold change | P value | T value |
|---|---|---|---|---|---|---|
| 1700011H14Rik | Mus musculus RIKEN cDNA 17000111114 gene (1700011HI4Rik), mRNA. | 7.36483 | 9.19796 | 3.563 up | 0.843 | -1.514 |
| 1700019H03Rik | Mus musculus RIKEN cDNA 17000191103 gene (1700019H03Rik), mRNA. | 6.50355 | 7.54659 | 2.060 up | 0.839 | -1.644 |
| 1700030F18Rik | Mus musculus RIKEN cDNA 1700030F18 gene (1700030F18Rik), mRNA | 6.82804 | 7.85039 | 2.031 up | 0.843 | -1.591 |
| 1700122C07Rik | | 6.2984 | 11.55465 | 38.219 up | 1 | -3.304 |
| 1810056I18Rik | | 6.62268 | 9.48201 | 7.256 up | 0.965 | -2.667 |
| 2010016I18Rik | PREDICTED: Mus musculus RIKEN cDNA 2010016118 gene (2010016I18Rik), misc RNA. | 8.52551 | 7.50158 | 2.033 down | 1 | 5.298 |
| 2310046K01Rik | Mus musculus RIKEN cDNA 2310046K0I gene (2310046K01Rik), mRNA. | 7.96582 | 9.27814 | 2.483 up | 0.839 | -1.755 |

| SYMBOL | DEFINITION | Mean WAT2 Control | Mean WAT2 KOKO | Fold change | P value | T value |
|---|---|---|---|---|---|---|
| 2610017I09Rik | PREDICTED: Mus musculus RIKEN cDNA 2610017109 gene (2610017I09Rik), misc RNA. | 6.44836 | 8.33149 | 3.688 up | 0.933 | -2.4 |
| 2900002J02Rik | | 8.98032 | 7.45887 | 2.870 down | 1 | 4.464 |
| 4631405K08Rik | | 6.09603 | 7.40761 | 2.482 up | 0.958 | -2.619 |
| 4930426D05Rik | | 7.0353 | 8.08805 | 2.074 up | 0.854 | -1.314 |
| 4930525K10Rik | Mus musculus RIKEN cDNA 4930525K10 gene (4930525K10Rik), mRNA. | 6.21806 | 9.52447 | 9.892 up | 0.839 | -1.802 |
| 4931407G18Rik | Mus musculus RIKEN cDNA 4931407G18 gene (4931407G18Rik), mRNA. | 7.70707 | 8.75751 | 2.071 up | 0.927 | -0.654 |
| 4933412E12Rik | PREDICTED: Mus musculus RIKEN cDNA 4933412E12 gene (4933412E12Rik), mRNA. | 7.20565 | 8.44525 | 2.361 up | 0.853 | -1.332 |
| 4933428A15Rik | | 7.4899 | 9.2726 | 3.440 up | 0.891 | -2.225 |
| 4933433J03Rik | | 6.67893 | 7.81508 | 2.197 up | 0.846 | -1.42 |

FIG. 2A

| SYMBOL | DEFINITION | Mean WAT2 Control | Mean WAT2 KOKO | Fold change | P value | T value |
|---|---|---|---|---|---|---|
| 5033403H07Rik | | 6.13843 | 7.4175 | 2.426 up | 0.858 | -1.1227 |
| 5830403L16Rik | Mus musculus RIKEN cDNA 5830403L16 gene (5830403L16Rik), mRNA. | 6.37214 | 9.53047 | 8.927 up | 0.844 | -1.508 |
| 5830411K21Rik | | 8.60245 | 7.42014 | 2.269 down | 0.947 | 2.475 |
| 8430408G22Rik | Mus musculus RIKEN cDNA 8430408G22 gene (8430408G22Rik), mRNA. | 10.55145 | 9.38151 | 2.250 down | 0.843 | 1.607 |
| 9130230L23Rik | PREDICTED: Mus musculus RIKEN cDNA 9130230L23 gene (9130230L23Rik), misc RNA. | 6.53854 | 8.96029 | 5.358 up | 0.924 | -2.374 |
| 9230002F21Rik | Mus musculus RIKEN cDNA 9230002F21 gene (9230002F21Rik), mRNA | 6.07327 | 11.30325 | 37.530 up | 0.99 | -2.897 |

| SYMBOL | DEFINITION | Mean WAT2 Control | Mean WAT2 KOKO | Fold change | P value | T value |
|---|---|---|---|---|---|---|
| 9230101D24Rik | | 6.1349 | 9.3174 | 9.078 up | 0.843 | -1.574 |
| 9230104J12Rik | | 6.25535 | 7.34457 | 2.127 up | 0.879 | -2.153 |
| 9230104LO9Rik | Mus musculus RIKEN cDNA 9230104L09 gene (9230104L09Rik), mRNA. | 6.16832 | 8.01646 | 3.600 up | 0.853 | -1.328 |
| 9230104O11 Rik | | 6.09135 | 7.9693 | 3.675 up | 0.863 | -1.192 |
| 9230107O10Rik | Mus musculus RIKEN cDNA 9230107010 gene (9230107010Rik), mRNA. | 6.14824 | 11.81554 | 50.819 up | 1 | -4.358 |
| 9230108M03Rik | | 6.32616 | 9.46945 | 8.835 up | 0.867 | -2.084 |
| 9230110F15Rik | PREDICTED: Mus musculus RIKEN cDNA 9230110F15 gene (9230110F15Rik), mRNA. | 6.04534 | 8.14352 | 4.281 up | 0.859 | -1.249 |
| 9230113A04Rik | | 6.72846 | 7.73965 | 2.015 up | 0.858 | -1.233 |
| 9530027K23Rik | | 6.39168 | 8.35847 | 3.908 up | 0.915 | -2.295 |
| 9626958_317 | | 7.3376 | 8.58408 | 2.372 up | 0.845 | -1.886 |
| 9626965_344 | | 6.24642 | 8.12542 | 3.678 up | 0.924 | -2.349 |

FIG. 2B

| SYMBOL | DEFINITION | Mean WAT2 Control | Mean WAT2 KOKO | Fold change | P value | T value |
|---|---|---|---|---|---|---|
| 9630015D15Rik | | 8.18501 | 9.85764 | 3.187 up | 0.928 | -2.383 |
| A430065P19Rik | | 6.09259 | 7.18943 | 2.138 up | 0.869 | -2.091 |
| Actg2 | Mus musculus actin, gamma 2, smooth muscle, enteric (Actg2), mRNA. | 9.08553 | 10.7778 | 3.231 up | 0.852 | -1.356 |
| Adam28 | Mus musculus a disintegrin and metallopeptidase domain 28 (Adam28), transcript variant, mRNA | 6.34736 | 8.02232 | 3.193 up | 0.858 | -1.261 |
| Adam7 | Mus musculus a disintegrin and metallopeptidase domain 7 (Adam7), mRNA | 6.22358 | 11.76529 | 46.582 up | 1 | -3.3 |
| Adcy8 | Mus musculus adenylate cyclase 8 (Adcy8), mRNA | 7.62668 | 8.9551 | 2.511 up | 0.869 | -1.133 |
| Adh6b | PREDICTED: Mus musculus alcohol dehydrogenase 6B (class V) (Adh6b), mRNA. | 6.61898 | 7.98497 | 2.577 up | 0.857 | -1.99 |

| SYMBOL | DEFINITION | Mean WAT2 Control | Mean WAT2 KOKO | Fold change | P value | T value |
|---|---|---|---|---|---|---|
| AI586015 | Mus musculus expressed sequence AI586015 (AI586015), mRNA | 6.38134 | 7.39939 | 2.025 up | 0.947 | -2.533 |
| Akrlc19 | Mus musculus aldo-keto reductase family 1, member C19 (Akrlc19), mRNA. | 7.42578 | 9.88101 | 5.484 up | 0.863 | -2.016 |
| Aldh3a1 | Mus musculus aldehyde dehydrogenase family 3, subfamily Al (Aldh3a1), mRNA | 6.18425 | 7.83819 | 3.146 up | 0.95 | -2.507 |
| Angptl4 | | 10.83615 | 9.81008 | 2.036 down | 0.986 | 2.816 |
| Ap1m2 | Mus musculus adaptor protein complex AP-1, mu 2 subunit (Ap1m2), mRNA | 6.31015 | 7.47545 | 2.242 up | 0.861 | -2.008 |
| Apoc3 | Mus musculus apolipoprotein C-III (Apoc3), mRNA. | 8.5895 | 7.34963 | 2.361 down | 1 | 3.305 |
| Aqp9 | Mus musculus aquaporin 9 (Aqp9), mRNA. | 7.46296 | 9.29684 | 3.564 up | 0.845 | -1.886 |

FIG. 2C

| SYMBOL | DEFINITION | Mean WAT2 Control | Mean WAT2 KOKO | Fold change | P value | T value |
|---|---|---|---|---|---|---|
| Asb11 | Mus musculus ankyrin repeat and SOCS box-containing protein 11 (Asb11), mRNA. | 6.17444 | 7.56692 | 2.625 up | 0.945 | -2.561 |
| Atp10b | Mus musculus ATPase, Class V, type 10B (Atp10b), mRNA. | 6.66947 | 8.4893 | 3.530 up | 0.948 | -2.521 |
| Atp13a4 | Mus musculus ATPase type 13A4 (Atp13a4), mRNA. | 6.70157 | 8.15576 | 2.740 up | 0.855 | -1.957 |
| Atp1a2 | Mus musculus ATPase, Na+/K+ transporting, alpha 2 polypeptide (Atp1a2), mRNA. | 11.65516 | 10.31812 | 2.526 down | 1 | 5.137 |
| Atp2b3 | Mus musculus ATPase, Ca++ transporting, plasma membrane 3 (Atp2b3), mRNA. | 6.1133 | 7.12663 | 2.018 up | 0.918 | -2.306 |
| Atp4a | Mus musculus ATPase, H+/K+ exchanging, gastric, alpha polypeptide (Atp4a), mRNA. | 6.16965 | 8.5475 | 5.197 up | 0.878 | -2.151 |

| SYMBOL | DEFINITION | Mean WAT2 Control | Mean WAT2 KOKO | Fold change | P value | T value |
|---|---|---|---|---|---|---|
| AU018778 | Mus musculus expressed sequence AU018778 (AU018778), mRNA. | 9.33341 | 8.27718 | 2.079 down | 1 | 3.955 |
| BC021891 | Mus musculus cDNA sequence BC021891 (BC021891), mRNA. | 6.72562 | 7.81475 | 2.127 up | 0.844 | -1.85 |
| BC037006 | | 7.45465 | 9.24551 | 3.460 up | 0.851 | -1.91 |
| BC043944 | | 6.38052 | 10.01957 | 12.458 up | 0.955 | -2.6 |
| BC048679 | Mus musculus cDNA sequence BC048679 (BC048679), mRNA. | 6.21451 | 12.14706 | 61.076 up | 1 | -3.482 |
| Bex2 | PREDICTED: Mus musculus brain expressed X-linked 2 (Bex2), mRNA. | 7.10564 | 9.23627 | 4.379 up | 0.854 | -1.967 |
| Bglap-rsl | Mus musculus bone gamma-carboxyglutamate protein, related sequence 1 (Bglap-rsl), mRNA. | 6.11193 | 7.67298 | 2.950 up | 0.843 | -1.608 |
| Bspry | | 6.49959 | 7.60467 | 2.151 up | 0.857 | -1.987 |
| C130072N01Rik | | 6.46359 | 7.92496 | 2.753 up | 0.862 | -1.207 |

FIG. 2D

| SYMBOL | DEFINITION | Mean WAT2 Control | Mean WAT2 KOKO | Fold change | P value | T value |
|---|---|---|---|---|---|---|
| C130090K23Rik | Mus musculus RIKEN cDNA C130090K23 gene (C130090K23Rik), mRNA. | 6.35307 | 8.64753 | 4.905 up | 0.872 | -2.125 |
| C4bp | | 6.12936 | 7.16292 | 2.047 up | 0.838 | -1.636 |
| C920004C08Rik | | 7.7363 | 9.02078 | 2.435 up | 0.842 | -1.865 |
| Cad | Mus musculus carbamoyl-phosphate synthetase 2, aspartate transcarbamylase, and dihydroorotase (Cad), mRNA. | 7.03975 | 9.53228 | 5.627 up | 0.946 | -2.464 |
| Calml3 | Mus musculus calmodulin-like 3 (Calml3), mRNA. | 8.04483 | 9.11374 | 2.097 up | 0.903 | -0.845 |
| Camk2b | Mus musculus calcium/calmodulin-dependent protein kinase II, beta (Camk2b), mRNA | 7.0426 | 8.84574 | 3.489 up | 0.854 | -1.959 |
| Capn5 | Mus musculus calpain 5 (Capn5), mRNA. | 8.1989 | 9.58536 | 2.614 up | 0.837 | -1.75 |

| SYMBOL | DEFINITION | Mean WAT2 Control | Mean WAT2 KOKO | Fold change | P value | T value |
|---|---|---|---|---|---|---|
| Car12 | | 6.1574 | 7.81812 | 3.161 up | 0.867 | -2.084 |
| Car4 | Mus musculus carbonic anhydrase 4 (Car4), mRNA | 8.70331 | 9.76556 | 2.088 up | 0.854 | -1.323 |
| Ccno | Mus musculus cyclin O (Ccno), mRNA. | 7.06159 | 8.65875 | 3.025 up | 0.837 | -1.684 |
| Cd52 | | 7.26505 | 10.72252 | 10.985 up | 0.993 | -2.878 |
| Cdh16 | Mus musculus cadherin 16 (Cdh16), mRNA | 6.9758 | 8.30869 | 2.519 up | 0.862 | -1.208 |
| Cds1 | Mus musculus CDP-diacylglycerol synthase 1 (Cds1), mRNA. | 8.55077 | 10.06871 | 2.863 up | 0.876 | -2.143 |
| Ceacam10 | Mus musculus CEA-related cell adhesion molecule 10 (Ceacam10), mRNA. | 6.22706 | 9.31588 | 8.507 up | 0.944 | -2.442 |
| Ces7 | Mus musculus carboxylesterase 7 (Ces7), mRNA. | 6.6324 | 10.63892 | 16.072 up | 0.957 | -2.618 |
| Ch25h | Mus musculus cholesterol 25-hydroxylase (Ch25h), mRNA. | 6.83913 | 8.04623 | 2.308 up | 0.847 | -1.428 |

FIG. 2E

| SYMBOL | DEFINITION | Mean WAT2 Control | Mean WAT2 KOKO | Fold change | P value | T value |
|---|---|---|---|---|---|---|
| Chst10 | Mus musculus carbohydrate sulfotransferase 10 (Chst10), mRNA. | 6.37778 | 7.4571 | 2.113 up | 0.857 | -1.979 |
| Clcnkb | | 6.69823 | 7.89636 | 2.294 up | 0.866 | -2.039 |
| Cldn1 | Mus musculus claudin 1 (Cldn1), mRNA. | 6.71794 | 7.83418 | 2.167 up | 0.843 | -1.855 |
| Cldn2 | Mus musculus claudin 2 (Cldn2), mRNA. | 6.99336 | 8.01302 | 2.027 up | 0.921 | -0.698 |
| Cldn23 | Mus musculus claudin 23 (Cldn23), mRNA. | 6.91636 | 8.00571 | 2.127 up | 0.842 | -1.618 |
| Cldn3 | Mus musculus claudin 3 (Cldn3), mRNA. | 6.79812 | 9.25531 | 5.491 up | 0.95 | -2.507 |
| Cldn4 | Mus musculus claudin 4 (Cldn4), mRNA. | 6.5784 | 8.24085 | 3.165 up | 0.836 | -1.68 |
| Clic3 | Mus musculus chloride intracellular channel 3 (Clic3), mRNA. | 6.47875 | 8.05646 | 2.984 up | 0.904 | -2.262 |

| SYMBOL | DEFINITION | Mean WAT2 Control | Mean WAT2 KOKO | Fold change | P value | T value |
|---|---|---|---|---|---|---|
| Cox8b | Mus musculus cytochrome c oxidase, subunit VIIIb (Cox8b), mRNA | 10.76467 | 9.76191 | 2.003 down | 0.864 | 2.023 |
| Cpn1 | | 6.34749 | 7.59597 | 2.375 up | 0.863 | -2.019 |
| Crisp4 | Mus musculus cysteine-rich secretory protein 4 (Crisp4), mRNA. | 6.2349 | 8.88768 | 6.288 up | 0.919 | -2.317 |
| Cryba4 | Mus musculus crystallin, beta A4 (Cryba4), mRNA. | 6.45468 | 8.94128 | 5.604 up | 0.851 | -1.383 |
| Cst11 | Mus musculus cystatin 11 (Cst11), mRNA. | 6.45513 | 8.6374 | 4.538 up | 0.859 | -1.248 |
| Cst12 | PREDICTED: Mus musculus cystatin 12 (Cst12), mRNA. | 6.49162 | 8.92384 | 5.397 up | 0.858 | -1.279 |
| Cuzd1 | Mus musculus CUB and zona pellucida-like domains 1 (Cuzd1), mRNA | 7.59103 | 12.29817 | 26.121 up | 0.964 | -2.689 |

FIG. 2F

| SYMBOL | DEFINITION | Mean WAT2 Control | Mean WAT2 KOKO | Fold change | P value | T value |
|---|---|---|---|---|---|---|
| Cyb561 | Mus musculus cytochrome b-561 (Cyb561), mRNA | 9.33655 | 11.84739 | 5.699 up | 0.943 | -2.447 |
| Cypl7a1 | Mus musculus cytochrome P450, family 17, subfamily a, polypeptide 1 (Cyp17a1), mRNA. | 6.43933 | 8.08562 | 3.130 up | 0.873 | -2.119 |
| Cyp2f2 | Mus musculus cytochrome P450, family 2, subfamily f, polypeptide 2 (Cyp2f2), mRNA. | 9.35425 | 7.61822 | 3.331 down | 0.834 | 7.965 |
| Cyp4a12a | Mus musculus cytochrome P450, family 4, subfamily a, polypeptide 12a (Cyp4a12a), mRNA. | 6.36348 | 7.68534 | 2.499 up | 0.843 | -1.574 |
| D730046L02Rik | | 5.98019 | 7.5937 | 3.059 up | 0.858 | -1.289 |
| D730048I06Rik | Mus musculus RIKEN cDNA D730048I06 gene (D730048I06Rik), mRNA. | 5.99513 | 8.2174 | 4.666 up | 0.837 | -1.747 |

| SYMBOL | DEFINITION | Mean WAT2 Control | Mean WAT2 KOKO | Fold change | P value | T value |
|---|---|---|---|---|---|---|
| Defb10 | Mus musculus defensin beta 10 (Defb10), mRNA | 6.21041 | 8.56641 | 5.119 up | 0.949 | -2.483 |
| Defb11 | Mus musculus defensin beta 11 (Defb11), mRNA. | 6.12356 | 10.26602 | 17.660 up | 0.948 | -2.516 |
| Defb12 | | 6.12104 | 8.91727 | 6.946 up | 0.846 | -1.443 |
| Defb14 | Mus musculus defensin beta 14 (Defb14), mRNA. | 6.70914 | 7.7437 | 2.048 up | 0.838 | -1.701 |
| Defb15 | Mus musculus defensin beta 15 (Defb15), mRNA. | 6.151 | 8.65821 | 5.685 up | 0.849 | -1.398 |
| Defb2 | Mus musculus defensin beta 2 (Defb2), mRNA. | 5.9315 | 10.11452 | 18.164 up | 0.968 | -2.717 |
| Defb29 | Mus musculus defensin beta 29 (Defb29), mRNA. | 6.63783 | 9.19317 | 5.878 up | 0.856 | -1.983 |
| Defb35 | Mus musculus defensin beta 35 (Defb35), mRNA. | 6.46942 | 7.62378 | 2.225 up | 0.864 | -1.186 |
| Defb38 | Mus musculus defensin beta 38 (Defb38), mRNA | 6.07616 | 11.34458 | 38.543 up | 0.991 | -2.886 |

FIG. 2G

| SYMBOL | DEFINITION | Mean WAT2 Control | Mean WAT2 KOKO | Fold change | P value | T value |
|---|---|---|---|---|---|---|
| Defb39 | Mus musculus defensin beta 39 (Defb39), mRNA. | 6.28345 | 9.97661 | 12.934 up | 0.946 | -2.58 |
| Defb40 | Mus musculus defensin beta 40 (Defb40), mRNA | 6.2331 | 9.31539 | 8.469 up | 0.89 | -2.185 |
| Defb42 | Mus musculus defensin beta 42 (Defb42), mRNA. | 6.51155 | 12.24583 | 53.234 up | 1 | -3.666 |
| Defb9 | Mus musculus defensin beta 9 (Defb9), mRNA. | 6.253 | 7.91815 | 3.171 | 0.837 | -1.661 |
| Defcr-rs10 | Mus musculus defensin related cryptdin, related sequence 10 (Defcr-rs10), mRNA | 6.11346 | 7.7446 | 3.097 up | 0.921 | -2.326 |
| DKFZp434J1813 | | 7.08971 | 9.01293 | 3.792 up | 0.911 | -2.275 |
| Dnase2a | | 6.50383 | 7.74923 | 2.370 up | 0.944 | -2.44 |
| Dusp5 | PREDICTED: Mus musculus dual specificity phosphatase 5 (Dusp5), mRNA. | 7.38524 | 8.47802 | 2.132 up | 0.964 | -2.705 |
| E430021N18Rik | | 7.80701 | 9.24777 | 2.714 up | 0.865 | -1.175 |

| SYMBOL | DEFINITION | Mean WAT2 Control | Mean WAT2 KOKO | Fold change | P value | T value |
|---|---|---|---|---|---|---|
| EG245440 | PREDICTED: Mus musculus predicted gene, EG245440 (EG245440), mRNA. | 6.01333 | 8.50468 | 5.623 up | 0.908 | -2.274 |
| EG432867 | Mus musculus predicted gene, EG432867 (EG432867), mRNA. | 6.68853 | 10.52517 | 14.287 up | 0.89 | -2.211 |
| EG433365 | Mus musculus predicted gene, EG433365 (EG433365), mRNA | 6.31696 | 7.31723 | 2.000 up | 0.858 | -1.266 |
| EG433865 | PREDICTED: Mus musculus predicted gene, EG433865 (EG433865), mRNA. | 8.85138 | 10.12417 | 2.416 up | 0.919 | -2.312 |
| EG546038 | Mus musculus predicted gene, EG546038 (EG546038), transcript variant h, mRNA. | 6.72254 | 9.86541 | 8.832 up | 0.837 | -1.659 |
| EG574083 | Mus musculus predicted gene, EG574083 (EG574083), mRNA. | 6.63781 | 9.03825 | 5.279 up | 0.936 | -2.41 |
| EG620839 | PREDICTED: Mus musculus predicted gene, EG620839 (EG620839), mRNA. | 6.47479 | 7.94119 | 2.763 up | 0.883 | -2.165 |

FIG. 2H

| SYMBOL | DEFINITION | Mean WAT2 Control | Mean WAT2 KOKO | Fold change | P value | T value |
|---|---|---|---|---|---|---|
| EG629114 | Mus musculus predicted gene, EG629114 (EG629114), mRNA. | 6.66875 | 10.91178 | 18.935 up | 0.997 | -2.93 |
| EG654457 | Mus musculus predicted gene, EG654457 (EG654457), mRNA. | 6.85442 | 8.81272 | 3.886 up | 0.852 | -1.912 |
| EG654458 | Mus musculus predicted gene, EG654458 (EG654458), mRNA. | 6.71524 | 10.04957 | 10.086 up | 0.887 | -2.172 |
| EG654460 | Mus musculus predicted gene, EG654460 (EG654460), mRNA. | 6.5481 | 9.70311 | 8.907 up | 0.843 | -1.551 |
| EG654465 | Mus musculus predicted gene, EG654465 (EG654465), mRNA. | 7.02202 | 9.34259 | 4.995 up | 0.86 | -1.218 |
| Egr2 | Mus musculus early growth response 2 (Egr2), mRNA. | 6.60172 | 8.57419 | 3.924 up | 0.872 | -2.129 |
| Emb | | 7.084 | 8.19261 | 2.156 up | 0.921 | -2.326 |
| Enpp1 | Mus musculus ectonucleotide pyrophosphatase/phosphodiesterase 1 (Enpp1), mRNA. | 6.51578 | 8.22222 | 3.263 up | 0.843 | -1.871 |

| SYMBOL | DEFINITION | Mean WAT2 Control | Mean WAT2 KOKO | Fold change | P value | T value |
|---|---|---|---|---|---|---|
| Epb4.114b | PREDICTED: Mus musculus erythrocyte protein band 4.1-like 4b, transcript variant 2 (Epb4.114b), mRNA. | 6.64529 | 7.74412 | 2.141 up | 0.87 | -2.093 |
| Fate1 | Mus musculus fetal and adult testis expressed 1 (Fate 1) on chromosome X. | 6.09166 | 7.09519 | 2.004 up | 0.861 | -2.007 |
| Fbxo10 | PREDICTED: Mus musculus F-box protein 10 (Fbxo 10), mRNA. | 9.15029 | 10.6083 | 2.747 up | 0.9 | -2.25 |
| Fdps | | 9.55309 | 10.6998 | 2.214 up | 1 | -4.48 |
| Fga | Mus musculus fibrinogen, alpha polypeptide (Fga), mRNA. | 6.38082 | 7.56928 | 2.279 up | 0.925 | -2.353 |
| Frag1 | Mus musculus FGF receptor activating protein 1 (Frag1), mRNA | 7.44123 | 9.09932 | 3.155 up | 0.947 | -2.487 |
| Fxyd3 | Mus musculus FXYD domain-containing ion transport regulator 3 (Fxyd3), mRNA | 7.06652 | 8.6064 | 2.907 up | 0.947 | -2.433 |

FIG. 2I

| SYMBOL | DEFINITION | Mean WAT2 Control | Mean WAT2 KOKO | Fold change | P value | T value |
|---|---|---|---|---|---|---|
| Gal3st4 | Mus musculus galactose-3-O-sulfotransferase 4 (Gal3st4), mRNA. XM_925485 XM_925486 XM_925488 | 6.28832 | 7.36836 | 2.114 up | 0.852 | -1.348 |
| Gata3 | Mus musculus GATA binding protein 3 (Gata3), mRNA. | 6.32692 | 7.64922 | 2.500 up | 0.934 | -2.398 |
| Gbp1 | Mus musculus guanylate nucleotide binding protein 1 (Gbp1), mRNA | 7.58136 | 6.32276 | 2.392 down | 0.837 | 1.739 |
| Gcap27 | | 8.68168 | 9.92921 | 2.374 up | 0.844 | -1.847 |
| Gfra1 | Mus musculus glial cell line derived neurotrophic factor family receptor alpha 1 (Gfra1), mRNA | 6.39862 | 8.14992 | 3.366 up | 0.843 | -1.839 |
| Gldc | Mus musculus glycine decarboxylase (Gldc), mRNA. | 6.28802 | 7.95009 | 3.164 up | 0.917 | -2.308 |
| Gm1679 | Mus musculus gene model 1679, (NCBI) (Gm1679), mRNA. | 6.6051 | 8.49451 | 3.704 up | 0.841 | -1.528 |

| SYMBOL | DEFINITION | Mean WAT2 Control | Mean WAT2 KOKO | Fold change | P value | T value |
|---|---|---|---|---|---|---|
| Gm46 | PREDICTED: Mus musculus gene model 46, (NCBI) (Gm46), mRNA | 6.27384 | 9.83135 | 11.773 up | 0.95 | -2.51 |
| Gm566 | PREDICTED: Mus musculus gene model 566, (NCBI), transcript variant 2 (Gm566), misc RNA. | 6.15917 | 9.15473 | 7.975 up | 0.923 | -2.34 |
| Gm749 | Mus musculus gene model 749, (NCBI) (Gm749), mRNA. | 6.11355 | 8.77378 | 6.321 up | 0.85 | -1.389 |
| Gm767 | Mus musculus gene model 767, (NCBI) (Gm767), mRNA | 6.20506 | 7.8569 | 3.142 up | 0.859 | -1.247 |
| Gm846 | Mus musculus gene model 846, (NCBI) (Gm846), mRNA. | 6.12423 | 9.50204 | 10.394 up | 0.948 | -2.534 |
| Got2 | Mus musculus glutamate oxaloacetate transaminase 2, mitochondrial (Got2), mRNA. | 9.62577 | 10.94748 | 2.499 up | 0.862 | -2.017 |
| Gpx5 | Mus musculus glutathione peroxidase 5 (Gpx5), mRNA. | 6.14975 | 9.75989 | 12.211 up | 0.839 | -1.725 |

FIG. 2J

| SYMBOL | DEFINITION | Mean WAT2 Control | Mean WAT2 KOKO | Fold change | P value | T value |
|---|---|---|---|---|---|---|
| Grb7 | Mus musculus growth factor receptor bound protein 7 (Grb7), mRNA. | 7.8494 | 9.75466 | 3.745 up | 0.842 | -1.828 |
| Grhl2 | Mus musculus grainyhead-like 2 (Drosophila) (Grhl2), mRNA. | 6.14296 | 7.26179 | 2.171 up | 0.92 | -2.324 |
| Gstm7 | Mus musculus glutathione S-transferase, mu 7 (Gstm7), mRNA. XM_922862 XM_922867 XM_988105 XM_988145 XM_988175 XM_988211 XM_988243 XM_993607 | 7.79814 | 10.4194 | 6.152 up | 0.867 | -2.057 |
| Hgfac | Mus musculus hepatocyte growth factor activator (Hgfac), mRNA | 6.18151 | 7.25143 | 2.099 up | 0.866 | -1.164 |
| Hip1r | Mus musculus huntingtin interacting protein 1 related (Hip1r), mRNA. | 8.20211 | 9.31486 | 2.162 up | 0.837 | -1.74 |

| SYMBOL | DEFINITION | Mean WAT2 Control | Mean WAT2 KOKO | Fold change | P value | T value |
|---|---|---|---|---|---|---|
| Hoxb2 | Mus musculus homeo box B2 (Hoxb2), mRNA | 7.99125 | 9.1005 | 2.157 up | 0.939 | -2.412 |
| Hoxb7 | Mus musculus homeo box B7 (Hoxb7), mRNA | 8.60811 | 9.97947 | 2.587 up | 0.837 | -1.746 |
| Hoxd9 | Mus musculus homeo box D9 (Hoxd9), mRNA. | 7.53313 | 8.59944 | 2.094 up | 0.847 | -1.894 |
| Hpdl | Mus musculus 4-hydroxyphenylpyruvate dioxygenase-like (Hpdl), mRNA. | 6.55947 | 8.92123 | 5.139 up | 1 | -3.057 |
| Indo | Mus musculus indoleamine-pyrrole 2,3 dioxygenase (Indo), mRNA | 6.36599 | 9.64594 | 9.713 up | 0.873 | -2.1 |
| Isg20 | Mus musculus interferon-stimulated protein (Isg20), mRNA | 7.38569 | 8.88525 | 2.827 up | 0.868 | -2.078 |
| Isoc2a | PREDICTED: Mus musculus isochorismatase domain containing 2a (Isoc2a), mRNA. | 9.5861 | 8.5387 | 2.066 down | 1 | 4.911 |

FIG. 2K

| SYMBOL | DEFINITION | Mean WAT2 Control | Mean WAT2 KOKO | Fold change | P value | T value |
|---|---|---|---|---|---|---|
| Jakmip1 | Mus musculus janus kinase and microtubule interacting protein 1 (Jakmip1), nRNA | 6.68397 | 7.76651 | 2.117 up | 0.867 | -2.078 |
| Kcnc4 | Mus musculus potassium voltage gated channel, Shaw-related subfamily, member 4 (Kcnc4), mRNA. | 6.33419 | 8.2111 | 3.672 up | 0.946 | -2.562 |
| Kcnk1 | | 7.23535 | 9.59461 | 5.131 up | 0.898 | -2.244 |
| Krt14 | Mus musculus keratin 14 (Krt14), mRNA. | 6.48244 | 8.82045 | 5.056 up | 1 | -3.564 |
| Krt18 | Mus musculus keratin 18 (Krt18), mRNA. | 7.74566 | 9.57615 | 3.556 up | 0.863 | -2.018 |
| Krt23 | Mus musculus keratin 23 (Krt23), mRNA. | 6.216 | 7.37391 | 2.231 up | 0.858 | -1.237 |
| Krt8 | Mus musculus keratin 8 (Krt8), mRNA. | 8.33981 | 10.43081 | 4.260 up | 0.855 | -1.951 |
| Lcn10 | Mus musculus lipocalin 10 (Lcn10), mRNA | 6.20842 | 8.7206 | 5.704 up | 0.854 | -1.314 |

| SYMBOL | DEFINITION | Mean WAT2 Control | Mean WAT2 KOKO | Fold change | P value | T value |
|---|---|---|---|---|---|---|
| Lcn12 | Mus musculus lipocalin 12 (Lcn12), mRNA | 6.34733 | 10.44348 | 17.102 up | 0.964 | -2.68 |
| Lcn13 | Mus musculus lipocalin 13 (Lcn13), mRNA | 6.12547 | 7.18689 | 2.086 up | 0.858 | -1.263 |
| Lcn2 | Mus musculus lipocalin 2 (Lcn2), mRNA. | 10.17873 | 11.62008 | 2.715 up | 0.895 | -0.924 |
| Lcn5 | Mus musculus lipocalin 5 (Lcn5), transcript variant 1, mRNA. | 6.5147 | 9.2767 | 6.783 up | 0.862 | -2.005 |
| Lcn8 | Mus musculus lipocalin 8 (Lcn8), mRNA. | 6.18092 | 10.52233 | 20.272 up | 0.891 | -2.219 |
| Lcn9 | Mus musculus lipocalin 9 (Lcn9), mRNA. | 6.49194 | 9.07529 | 5.993 up | 0.846 | -1.425 |
| LOC100041932 | PREDICTED: Mus musculus hypothetical protein LOC100041932 (LOC100041932), mRNA. | 6.79402 | 8.45071 | 3.152 up | 0.838 | -1.764 |

FIG. 2L

| SYMBOL | DEFINITION | Mean WAT2 Control | Mean WAT2 KOKO | Fold change | P value | T value |
|---|---|---|---|---|---|---|
| LOC100044177 | PREDICTED: Mus musculus hypothetical protein LOC 100044177 (LOC 100044177), mRNA. | 9.54143 | 10.55303 | 2.016 up | 0.846 | -1.487 |
| LOC100044908 | PREDICTED: Mus musculus similar to CUG-BP and ETR-3 like factor 4 (LOC100044908), mRNA. | 7.18239 | 8.36827 | 2.275 up | 0.992 | -2.904 |
| LOC100045716 | PREDICTED: Mus musculus similar to 22 kDa neuronal tissue-enriched acidic protein (LOC100045716), mRNA | 10.65626 | 12.53714 | 3.682 up | 0.985 | -2.841 |
| LOC100045934 | PREDICTED: Mus musculus similar to WAP8C (LOC100045934), mRNA. | 6.2071 | 7.50819 | 2.464 up | 0.84 | -1.819 |
| LOC100046120 | PREDICTED: Mus musculus similar to clusterin (LOC100046120), mRNA. | 10.62613 | 12.19243 | 2.961 up | 0.843 | -1.543 |

| SYMBOL | DEFINITION | Mean WAT2 Control | Mean WAT2 KOKO | Fold change | P value | T value |
|---|---|---|---|---|---|---|
| LOC100046278 | PREDICTED: Mus musculus similar to CRS4C-6 (LOC100046278), mRNA. | 6.68066 | 11.60432 | 30.350 up | 1 | -2.973 |
| LOC100047619 | PREDICTED: Mus musculus similar to solute carrier family 7 (cationic amino acid transporter, y+ system), member 5 (LOC100047619), misc RNA | 8.42133 | 9.70706 | 2.438 up | 0.875 | -1.085 |
| LOC100047810 | PREDICTED: Mus musculus similar to transmembrane emp24 protein transport domain containing 6 (LOC1000478 10), mRNA | 7.25135 | 10.53032 | 9.706 up | 0.871 | -2.132 |
| LOC331089 | | 6.24677 | 10.41902 | 18.028 up | 0.975 | -2.736 |
| LOC381957 | | 6.10907 | 9.98018 | 14.632 up | 0.959 | -2.631 |
| LOC384348 | | 7.25375 | 8.37369 | 2.173 up | 0.891 | -2.193 |
| LOC385068 | | 11.57851 | 10.36375 | 2.321 down | 0.91 | 6.99 |

FIG. 2M

| SYMBOL | DEFINITION | Mean WAT2 Control | Mean WAT2 KOKO | Fold change | P value | T value |
|---|---|---|---|---|---|---|
| LOC546006 | PREDICTED: Mus musculus similar to deleted in malignant brain tumors 1 (LOC546006), mRNA. | 6.18494 | 7.42188 | 2.356 up | 0.926 | -2.364 |
| LOC624610 | PREDICTED: Mus musculus hypothetical protein LOC624610 (LOC624610), mRNA | 6.99163 | 8.82438 | 3.562 up | 0.89 | -2.222 |
| LOC640195 | PREDICTED: Mus musculus similar to mucin 5, subtype B, tracheobronchial (LOC640195), misc RNA. | 6.09468 | 7.92956 | 3.567 up | 0.855 | 1.318 |
| LOC666403 | PREDICTED: Mus musculus similar to ribosomal protein S2 (LOC666403), misc RNA | 11.16581 | 8.81252 | 5.109 down | 0.865 | 2.055 |
| LOC669168 | PREDICTED: Mus musculus similar to Histone deacetylase 6 (HD6) (Histone deacetylase mHDA2) (LOC669168), mRNA. | 7.19308 | 8.52366 | 2.515 up | 0.844 | -1.849 |

| SYMBOL | DEFINITION | Mean WAT2 Control | Mean WAT2 KOKO | Fold change | P value | T value |
|---|---|---|---|---|---|---|
| LOC673501 | PREDICTED: Mus musculus hypothetical protein LOC673501 (LOC673501), mRNA. | 13.93133 | 12.86872 | 2.088 down | 0.987 | 6.756 |
| Ltf | Mus musculus lactotransferrin (Ltf), mRNA | 6.32062 | 9.28949 | 7.829 up | 0.873 | -2.116 |
| Ly6f | Mus musculus lymphocyte antigen 6 complex, locus F (Ly6f), mRNA. | 6.13936 | 8.91566 | 6.850 up | 0.87 | -2.093 |
| Ly6g5b | Mus musculus lymphocyte antigen 6 complex, locus G5B (Ly6g5b), mRNA | 6.18722 | 8.73615 | 5.851 up | 0.853 | -1.344 |
| Ly6g5c | Mus musculus lymphocyte antigen 6 complex, locus G5C (Ly6g5c), mRNA. | 6.22722 | 9.15483 | 7.608 up | 0.847 | -1.483 |
| Mboat1 | Mus musculus membrane bound O-acyltransferase domain containing 1 (Mboat1), mRNA | 7.25737 | 8.69697 | 2.712 up | 0.844 | -1.885 |

FIG. 2N

| SYMBOL | DEFINITION | Mean WAT2 Control | Mean WAT2 KOKO | Fold change | P value | T value |
|---|---|---|---|---|---|---|
| Mboat2 | Mus musculus membrane bound O-acyltransferase domain containing 2 (Mboat2), transcript variant 2, mRNA. | 6.35118 | 7.36691 | 2.021 up | 0.945 | -2.562 |
| Mfsd2 | Mus musculus major facilitator superfamily domain containing 2 (Mfsd2), mRNA. | 6.31244 | 8.1347 | 3.536 up | 0.847 | -1.454 |
| Mia1 | | 7.44466 | 8.8645 | 2.675 up | 0.862 | -1.204 |
| Mid1ip1 | Mus musculus Mid1 interacting protein 1 (gastrulation specific G12-like (zebrafish)) (Mid1ip1), mRNA. | 10.24577 | 11.55081 | 2.470 up | 1 | -5.283 |
| Mrp137 | Mus musculus mitochondrial ribosomal protein L37 (Mrp137), mRNA | 10.02052 | 11.09845 | 2.111 up | 0.872 | -1.118 |

| SYMBOL | DEFINITION | Mean WAT2 Control | Mean WAT2 KOKO | Fold change | P value | T value |
|---|---|---|---|---|---|---|
| Mthfd11 | Mus musculus methylene-tetrahydrofolate dehydrogenase (NADP+ dependent) 1-like (Mthfd11), mRNA. | 7.34232 | 8.78396 | 2.716 up | 0.89 | -2.198 |
| Mthfd2 | | 8.23372 | 10.21642 | 3.952 up | 1 | -3.253 |
| Myo5b | Mus musculus myosin Vb (Myo5b), mRNA. | 7.21562 | 8.32645 | 2.159 up | 0.842 | -1.582 |
| Myom2 | | 6.2559 | 7.69356 | 2.708 up | 0.867 | -2.076 |
| Ncam1 | Mus musculus neural cell adhesion molecule 1 (Ncam1, transcript variant 2, mRNA. | 6.60789 | 7.91401 | 2.472 up | 0.89 | -2.213 |
| Ngfrap1 | Mus musculus nerve growth factor receptor (TNFRSF16) associated protein 1 (Ngfrap1), mRNA | 8.64824 | 9.8362 | 2.278 up | 0.837 | -1.676 |
| Nnat | | 10.46356 | 9.20927 | 2.385 down | 0.894 | 2.228 |

FIG. 2O

| SYMBOL | DEFINITION | Mean WAT2 Control | Mean WAT2 KOKO | Fold change | P value | T value |
|---|---|---|---|---|---|---|
| Npy | Mus musculus neuropeptide Y (Npy), mRNA | 6.25445 | 9.94433 | 12.905 up | 0.944 | -2.46 |
| Ntsr2 | Mus musculus neurotensin receptor 2 (Ntsr2), mRNA. | 7.38955 | 9.04811 | 3.157 up | 0.858 | -1.288 |
| Nup210 | Mus musculus nucleoporin 210 (Nup210), mRNA. | 6.83772 | 8.45543 | 3.068 up | 1 | -3.343 |
| Oaz3 | Mus musculus ornithine decarboxylase antizyme 3 (Oaz3), mRNA | 8.03553 | 9.69108 | 3.150 up | 0.903 | -0.857 |
| Ociad2 | Mus musculus OCIA domain containing 2 (Ociad2), mRNA. | 6.98596 | 8.16152 | 2.258 up | 0.848 | -1.458 |
| Odf1 | Mus musculus outer dense fiber of sperm tails 1 (Odf1), mRNA. | 7.5697 | 9.4374 | 3.649 up | 0.882 | -1.036 |
| Opn1mw | Mus musculus opsin 1 (cone pigments), medium-wave-sensitive (color blindness, deutan) (Opn1mw), mRNA. | 6.17182 | 7.1803 | 2.011 up | 0.861 | -2.007 |

| SYMBOL | DEFINITION | Mean WAT2 Control | Mean WAT2 KOKO | Fold change | P value | T value |
|---|---|---|---|---|---|---|
| Osr2 | Mus musculus odd-skipped related 2 (Drosophila) (Osr2), mRNA. | 7.8921 | 9.47843 | 3.002 up | 0.841 | -1.823 |
| OTTMUSG 00000015285 | Mus musculus predicted gene, OTTMUS000000015852 (OTTMUSG00000015852), mRNA. | 7.55052 | 13.09296 | 46.605 up | 1 | -3.68 |
| OTTMUSG 00000015859 | Mus musculus predicted gene, OTTMUSG00000015859 (OTTMUSG00000015859), mRNA | 6.96681 | 9.17715 | 4.627 up | 0.862 | -1.207 |
| OTTMUSG 00000015862 | Mus musculus predicted gene, OTTMUSG00000015862 (OTTMUSG00000015862), mRNA. | 6.86927 | 9.62553 | 6.756 up | 0.852 | -1.371 |
| Ovch2 | Mus musculus ovochymase 2 (Ovch2), mRNA. | 6.34335 | 8.48753 | 4.420 up | 0.858 | -1.237 |
| Pdzk1 | | 7.46816 | 9.11905 | 3.140 up | 0.875 | -1.088 |

FIG. 2P

| SYMBOL | DEFINITION | Mean WAT2 Control | Mean WAT2 KOKO | Fold change | P value | T value |
|---|---|---|---|---|---|---|
| Pdzk1ip1 | Mus musculus PDZK1 interacting protein 1 (Pdzk1ip1), mRNA. | 6.984 | 8.90856 | 3.796 up | 0.843 | -1.876 |
| Pebp1 | Mus musculus phosphatidyl-ethanolamine binding protein 1 (Pebp1), mRNA. | 9.3806 | 10.54229 | 2.237 up | 0.866 | -2.071 |
| Plac8 | Mus musculus placenta-specific 8 (Plac8), mRNA. | 7.6606 | 9.09571 | 2.704 up | 0.847 | -1.413 |
| Podn | Mus musculus podocan (Podn), mRNA. | 8.9809 | 7.96806 | 2.017 down | 0.798 | 7.674 |
| Ppp1r3c | Mus musculus protein phosphatase 1, regulatory (inhibitor) subunit 3C (Ppp1r3c), mRNA. | 11.50166 | 10.06966 | 2.698 down | 0.99 | 2.843 |
| Prm1 | Mus musculus protamine 1 (Prm1), mRNA. | 8.99935 | 10.91828 | 3.781 up | 0.908 | -0.798 |
| Prm2 | Mus musculus protamine 2 (Prm2), mRNA. | 8.28028 | 9.64693 | 2.578 up | 0.924 | -0.679 |
| Prom | | 6.31788 | 8.12266 | 3.493 up | 0.92 | -2.318 |
| Prom1 | | 7.7927 | 10.83644 | 8.246 up | 0.925 | -2.366 |

| SYMBOL | DEFINITION | Mean WAT2 Control | Mean WAT2 KOKO | Fold change | P value | T value |
|---|---|---|---|---|---|---|
| Prom2 | Mus musculus prominin 2 (Prom2), transcript variant 1, mRNA. | 6.7525 | 9.70256 | 7.727 up | 0.947 | -2.435 |
| Prr15 | Mus musculus proline rich 15 (Prr15), mRNA. | 8.19995 | 9.37425 | 2.256 up | 0.842 | -1.87 |
| Prss8 | Mus musculus protease, serine, 8 (prostasin) (Prss8), mRNA. | 6.55149 | 7.97648 | 2.685 up | 0.931 | -2.391 |
| Ptgds | Mus musculus prostaglandin D2 synthase (brain) (Ptgds), mRNA. | 7.46916 | 11.13211 | 12.666 up | 0.94 | -2.414 |
| Rab11fip4 | | 6.83435 | 8.17467 | 2.532 up | 0.837 | -1.689 |
| Rab25 | Mus musculus RAB25, member RAS oncogene family (Rab25), mRNA. | 6.81396 | 8.93307 | 4.344 up | 0.912 | -2.287 |
| Rab26 | PREDICTED: Mus musculus RAB26, member RAS oncogene family, transcript variant 1 (Rab26), mRNA | 6.27935 | 7.74322 | 2.758 up | 0.855 | -1.306 |

FIG. 2Q

| SYMBOL | DEFINITION | Mean WAT2 Control | Mean WAT2 KOKO | Fold change | P value | T value |
|---|---|---|---|---|---|---|
| Rab6b | Mus musculus RAB6B, member RAS oncogene family (Rab6b), mRNA | 6.99864 | 8.21272 | 2.319 up | 0.918 | -8.305 |
| Ramp1 | Mus musculus receptor (calcitonin) activity modifying protein 1 (Ramp 1), mRNA. | 7.76273 | 9.38981 | 3.088 up | 0.843 | -1.859 |
| Ramp3 | Mus musculus receptor (calcitonin) activity modifying protein 3 (Ramp3), mRNA. | 6.76744 | 8.76191 | 3.984 up | 0.912 | -2.287 |
| Rbm11 | Mus musculus RNA binding motif protein 11 (Rbm11), mRNA. | 6.64606 | 8.00101 | 2.557 up | 0.858 | -1.253 |
| Rbm35a | Mus musculus RNA binding motif protein 35A (Rbm35a), mRNA. | 6.53392 | 8.10331 | 2.967 up | 0.884 | -2.17 |
| Rbp7 | Mus musculus retinol binding protein 7, cellular (Rbp7), mRNA. | 9.60514 | 8.56321 | 2.058 down | 0.842 | 1.563 |

| SYMBOL | DEFINITION | Mean WAT2 Control | Mean WAT2 KOKO | Fold change | P value | T value |
|---|---|---|---|---|---|---|
| Rhcg | Mus musculus Rhesus blood group-associated C glycoprotein (Rhcg), mRNA | 6.38985 | 7.45917 | 2.098 up | 0.857 | -1.269 |
| Rn18s | Mus musculus 18S RNA (Rnl8s). | 14.60629 | 13.52637 | 2.113 down | 0.0518 | 20.339 |
| Rnase10 | Mus musculus ribonuclease, RNase A family, 10 (non-active) (Rnase10), mRNA. | 6.79724 | 8.13012 | 2.519 up | 0.88 | -1.049 |
| Rnase12 | Mus musculus ribonuclease, RNase A family, 12 (non-active) (Rnase12), mRNA. | 6.6423 | 10.69457 | 16.590 up | 0.946 | -2.577 |
| Rnase9 | Mus musculus ribonuclease, RNase A family, 9 (non-active) (Rnase9), mRNA. | 6.09092 | 9.24294 | 8.888 up | 0.999 | -2.969 |
| Rnfl 86 | Mus musculus ring finger protein 186 (Rnfl 86), mRNA. | 7.10037 | 8.30266 | 2.301 up | 0.855 | -1.319 |
| Rpl3l | Mus musculus ribosomal protein L3-like (Rpl3l), mRNA | 6.50561 | 9.44321 | 7.661 up | 0.947 | -2.58 |

FIG. 2R

| SYMBOL | DEFINITION | Mean WAT2 Control | Mean WAT2 KOKO | Fold change | P value | T value |
|---|---|---|---|---|---|---|
| Rprm | Mus musculus reprimo, TP53 dependent G2 arrest mediator candidate (Rprm), mRNA | 6.21248 | 8.26651 | 4.152 up | 0.948 | -2.501 |
| Serpina1f | Mus musculus serine (or cysteine) peptidase inhibitor, clade A, member 1f (Serpina1 f), mRNA. | 6.2119 | 10.59888 | 20.922 up | 1 | -2.935 |
| Sgpp1 | Mus musculus sphingosine-1-phosphate phosphatase 1 (Sgpp1), mRNA. | 8.72538 | 9.80464 | 2.112 up | 0.857 | -1.984 |
| Sh3g12 | Mus musculus SH3-domain GRB2-like 2 (Sh3g12), mRNA | 6.80347 | 8.11797 | 2.487 up | 0.837 | -1.691 |
| Sh3yl1 | Mus musculus Sh3 domain YSC-like 1 (Sh3yl1), mRNA. | 8.09485 | 9.33133 | 2.356 up | 0.872 | -2.1 |
| Shh | Mus musculus sonic hedgehog (Shh), mRNA. | 6.11101 | 7.12388 | 2.017 up | 0.944 | -2.425 |

| SYMBOL | DEFINITION | Mean WAT2 Control | Mean WAT2 KOKO | Fold change | P value | T value |
|---|---|---|---|---|---|---|
| Skap1 | Mus musculus src family associated phosphoprotein 1 (Skap1), mRNA. | 6.43956 | 7.87119 | 2.697 up | 0.925 | -2.354 |
| Slc1a1 | Mus musculus solute carrier family 1 (neuronal/epithelial high affinity glutamate transporter, system Xag), member 1 (Slc1a1), mRNA. XM_001002173 XM_001002184 XM_001002198 XM_001002207 | 6.69198 | 8.59524 | 3.740 up | 0.911 | -2.286 |
| Slc1a3 | Mus musculus solute carrier family 1 (glial high affinity glutamate transporter), member 3 (Slc1a3), mRNA | 11.49264 | 10.45417 | 2.054 down | 1 | 4.381 |
| Slc30a2 | | 7.16922 | 8.381 | 2.316 up | 0.879 | -1.058 |
| Slc38a5 | Mus musculus solute carrier family 38, member 5 (Slc38a5), mRNA | 8.0935 | 10.97435 | 7.365 up | 0.836 | -1.681 |

FIG. 2S

| SYMBOL | DEFINITION | Mean WAT2 Control | Mean WAT2 KOKO | Fold change | P value | T value |
|---|---|---|---|---|---|---|
| Slc44a4 | Mus musculus solute carrier family 44, member 4 (Slc44a4), mRNA. | 7.4756 | 9.05792 | 2.994 up | 0.845 | -1.889 |
| Slc7a4 | | 6.60755 | 8.47218 | 3.641 up | 0.91 | -2.286 |
| Smarca1 | Mus musculus SWI/SNF related, matrix associated, actin dependent regulator of chromatin, subfamily a, member 1 (Smarca1), mRNA | 7.36602 | 8.60736 | 2.364 up | 0.844 | -1.88 |
| Smarcd3 | Mus musculus SWI/SNF related, matrix associated, actin dependent regulator of chromatin, subfamily d, member 3 (Smarcd3), mRNA. | 8.06365 | 9.51466 | 2.733 up | 0.854 | -1.95 |
| Smcp | Mus musculus sperm mitochondria-associated cysteine-rich protein (Smcp), mRNA. | 6.98568 | 8.22476 | 2.360 up | 0.895 | -0.926 |

| SYMBOL | DEFINITION | Mean WAT2 Control | Mean WAT2 KOKO | Fold change | P value | T value |
|---|---|---|---|---|---|---|
| Snapc4 | Mus musculus small nuclear RNA activating complex, polypeptide 4 (Snapc4), mRNA. | 7.80836 | 9.0216 | 2.318 up | 0.852 | -1.934 |
| Spag11 | Mus musculus sperm associated antigen 11 (Spag11), mRNA. | 6.1772 | 10.75805 | 23.931 up | 1 | -3.061 |
| Spin2 | Mus musculus spindlin family, member 2 (Spin2), mRNA. | 6.28153 | 7.3627 | 2.115 up | 0.847 | -1.434 |
| Spink10 | Mus musculus serine peptidase inhibitor, Kazal type 10 (Spink10), mRNA. | 6.1256 | 10.45151 | 20.055 up | 0.95 | -2.504 |
| Spink12 | Mus musculus serine peptidase inhibitor, Kazal type 11 (Spink12), mRNA. | 6.21378 | 8.04076 | 3.547 up | 0.843 | -1.601 |
| Spink2 | Mus musculus serine peptidase inhibitor, Kazal type 2 (Spink2), mRNA. | 7.7001 | 9.50116 | 3.484 up | 0.858 | -1.283 |

FIG. 2T

| SYMBOL | DEFINITION | Mean WAT2 Control | Mean WAT2 KOKO | Fold change | P value | T value |
|---|---|---|---|---|---|---|
| Spink5 | Mus musculus serine peptidase inhibitor, Kazal type 5 (Spink5), mRNA. | 6.1453 | 7.54546 | 2.639 up | 0.849 | -1.399 |
| Spink8 | Mus musculus serine peptidase inhibitor, Kazal type 8 (Spink8), mRNA. | 6.30438 | 12.48887 | 72.730 up | 1 | -4.465 |
| Spin1w1 | Mus musculus serine protease inhibitor-like, with Kunitz and WAP domains 1 (eppin) (Spin1w1), mRNA | 6.17749 | 9.62511 | 10.910 up | 0.954 | -2.61 |
| Spint1 | Mus musculus serine protease inhibitor, Kunitz type 1 (Spint1), mRNA | 7.21449 | 8.39013 | 2.258 up | 0.836 | -1.681 |
| Spint4 | Mus musculus serine protease inhibitor, Kunitz type 4 (Spint4), mRNA. | 5.99951 | 11.97772 | 63.040 up | 1 | -4.247 |
| Srd5a2 | Mus musculus steroid 5 alpha-reductase 2 (Srd5a2), mRNA. | 6.89171 | 8.3231 | 2.697 up | 0.838 | -1.72 |

| SYMBOL | DEFINITION | Mean WAT2 Control | Mean WAT2 KOKO | Fold change | P value | T value |
|---|---|---|---|---|---|---|
| Ss18l1 | Mus musculus synovial sarcoma translocation gene on chromosome 18-like 1 (Ss18l1), mRNA. | 7.21153 | 8.26837 | 2.080 up | 0.912 | -2.288 |
| St6gal1 | Mus musculus beta galactoside alpha 2,6 sialyltransferase 1 (St6gal1), mRNA. | 8.94026 | 10.24671 | 2.473 up | 0.857 | -1.27 |
| Stard10 | Mus musculus START domain containing 10 (Stard10), mRNA. | 8.10349 | 9.13452 | 2.043 up | 0.843 | -1.54 |
| Suox | Mus musculus sulfite oxidase (Suox), mRNA. | 9.42528 | 10.87182 | 2.725 up | 0.839 | -1.815 |
| Sytl4 | Mus musculus synaptotagmin-like 4 (Sytl4), mRNA. | 7.42531 | 8.90221 | 2.783 up | 0.837 | -1.684 |
| Tacstd2 | Mus musculus tumor-associated calcium signal transducer 2 (Tacstd2), mRNA. | 6.20602 | 7.7977 | 3.014 up | 0.896 | -2.24 |

FIG. 2U

| SYMBOL | DEFINITION | Mean WAT2 Control | Mean WAT2 KOKO | Fold change | P value | T value |
|---|---|---|---|---|---|---|
| Tcfap2b | Mus musculus transcription factor AP-2 beta (Tcfap2b), transcript variant 2, mRNA. | 6.36609 | 7.60684 | 2.363 up | 0.944 | -2.448 |
| Tcfcp2l1 | Mus musculus transcription factor CP2-like 1 (Tcfcp2l1), mRNA. | 7.57385 | 8.75676 | 2.270 up | 0.864 | -2.028 |
| Teddm1 | Mus musculus transmembrane epididymal protein 1 (Teddm1), mRNA. | 6.17654 | 7.49976 | 2.502 up | 0.868 | -1.143 |
| Tes | Mus musculus testis derived transcript (Tes), transcript variant 1, mRNA. | 7.7871 | 8.84981 | 2.088 up | 0.945 | -2.426 |
| Tm7sf2 | Mus musculus transmembrane 7 superfamily member 2 (Tm7sf2), mRNA. | 7.16036 | 8.22425 | 2.090 up | 1 | -3.632 |
| Tmc5 | Mus musculus transmembrane channel-like gene family 5 (Tmc5), mRNA. | 6.67227 | 7.97233 | 2.462 up | 0.947 | -2.533 |

| SYMBOL | DEFINITION | Mean WAT2 Control | Mean WAT2 KOKO | Fold change | P value | T value |
|---|---|---|---|---|---|---|
| Tmem51 | Mus musculus transmembrane protein 51 (Tmem51), mRNA. | 8.32021 | 10.05829 | 3.335 up | 0.904 | -2.267 |
| Tnk1 | Mus musculus tyrosine kinase, non-receptor, 1 (Tnk1), mRNA | 7.72643 | 8.92853 | 2.300 up | 0.981 | -2.746 |
| Tnnt2 | Mus musculus troponin T2, cardiac (Tnnt2), mRNA. | 6.962 | 8.24023 | 2.425 up | 0.854 | -1.967 |
| Tox3 | Mus musculus TOX high mobility group box family member 3 (Tox3), mRNA | 6.27283 | 7.40034 | 2.184 up | 0.981 | -2.76 |
| Tpd52l1 | Mus musculus tumor protein D52-like 1 (Tpd52l1), mRNA. | 6.61927 | 7.66002 | 2.057 up | 0.846 | -1.479 |
| Tppp | Mus musculus tubulin polymerization promoting protein (Tppp), mRNA. | 8.42689 | 7.40661 | 2.028 down | 1 | 3.357 |
| Ucp1 | Mus musculus uncoupling protein 1 (mitochondrial, proton carrier) (Ucp1), mRNA. | 6.26081 | 7.34124 | 2.114 up | 0.9 | -2.251 |

FIG. 2V

| SYMBOL | DEFINITION | Mean WAT2 Control | Mean WAT2 KOKO | Fold change | P value | T value |
|---|---|---|---|---|---|---|
| Vash2 | Mus musculus vasohibin 2 (Vash2), mRNA. | 7.14086 | 8.65038 | 2.847 up | 0.866 | -2.069 |
| Wars | Mus musculus tryptophanyl-tRNA synthetase (Wars), mRNA. | 8.43389 | 9.73627 | 2.466 up | 0.898 | -2.244 |
| Wfdc10 | Mus musculus WAP four-disulfide core domain 10 (Wfdc10), mRNA. | 6.34075 | 12.47709 | 70.343 up | 1 | -3.58 |
| Wfdc13 | Mus musculus WAP four-disulfide core domain 13 (Wfdc13), mRNA. | 6.69979 | 10.141 | 10.861 up | 0.948 | -2.474 |
| Wfdc15b | Mus musculus WAP four-disulfide core domain 15B (Wfdc15b), transcript variant 1, mRNA. | 6.73288 | 10.8595 | 17.467 up | 0.95 | -2.589 |
| Wfdc6b | Mus musculus WAP four-disulfide core domain 6B (Wfdc6b), mRNA. | 6.45231 | 11.35331 | 29.877 up | 1 | -3.012 |

| SYMBOL | DEFINITION | Mean WAT2 Control | Mean WAT2 KOKO | Fold change | P value | T value |
|---|---|---|---|---|---|---|
| Zfp185 | Mus musculus zinc finger protein 185 (Zfp185), mRNA | 8.40967 | 9.61935 | 2.312 up | 0.888 | -2.175 |

FIG. 2W

| SYMBOL | DEFINITION | Mean WAT16 Control | Mean WAT16 KOKO | Fold change | P value | T value |
|---|---|---|---|---|---|---|
| 1190007I07Rik | PREDICTED: Mus musculus RIKEN cDNA 1190007O7 gene (1190007I07Rik), mRNA. | 7.93506 | 6.82343 | 2.160 down | 1 | 5.928 |
| A630077B13Rik | Mus musculus RIKEN cDNA A630077B13 gene (A630077B13Rik), mRNA. | 8.64026 | 7.57658 | 2.090 down | 1 | 1.61 |
| Atp10d | Mus musculus ATPase, Class V, type 10D (Atp10d), mRNA. | 8.31684 | 9.60704 | 2.445 up | 1 | -3.07 |
| Ccl24 | Mus musculus chemokine (C-C motif) ligand 24 (Ccl24), mRNA. | 8.14371 | 9.18718 | 2.061 up | 1 | -2.02 |
| Ccl4 | Mus musculus chemokine (C-C motif) ligand 4 (Ccl4), mRNA | 8.35172 | 7.32866 | 2.032 down | 1 | 2.042 |

| SYMBOL | DEFINITION | Mean WAT16 Control | Mean WAT16 KOKO | Fold change | P value | T value |
|---|---|---|---|---|---|---|
| Ccl5 | Mus musculus chemokine (C-C motif) ligand 5 Ccl5), mRNA. | 9.68289 | 8.45187 | 2.347 down | 1 | 1.697 |
| Cd209b | Mus musculus CD209b antigen (Cd209b), transcript variant 2, mRNA. | 7.80016 | 9.25368 | 2.738 up | 1 | -2.133 |
| Cd209d | Mus musculus CD209d antigen (Cd209d), mRNA. | 7.70678 | 9.18469 | 2.785 up | 1 | -2.161 |
| Cpa3 | Mus musculus carboxypeptidase A3, mast cell (Cpa3), mRNA | 9.57783 | 8.4918 | 2.122 down | 1 | 4.179 |
| Cyp2f2 | Mus musculus cytochrome P450, family 2, subfamily f, polypeptide 2 (Cyp2f2), mRNA. | 6.99875 | 8.04715 | 2.068 up | 1 | -2.123 |

FIG. 3A

| SYMBOL | DEFINITION | Mean WAT16 Control | Mean WAT16 KOKO | Fold change | P value | T value |
|---|---|---|---|---|---|---|
| Ear1 1 | Mus musculus eosinophil-associated, ribonuclease A family member 11 (Ear1 1), mRNA. | 7.5643 | 9.34912 | 3.445 up | 1 | -1.787 |
| Fabp3 | Mus musculus fatty acid binding protein 3, muscle and heart (Fabp3), mRNA. | 7.36145 | 8.73453 | 2.590 up | 1 | -7.971 |
| Fbxw5 | Mus musculus F-box and WD-40 domain protein 5 (Fbxw5), mRNA. | 8.6354 | 6.46091 | 4.514 down | 1 | 2.501 |
| Fcgr4 | Mus musculus Fc receptor, IgG, low affinity IV (Fcgr4), mRNA | 10.43407 | 9.19401 | 2.362 down | 1 | 1.357 |
| Hal | Mus musculus histidine ammonia lyase (Hal), mRNA. | 7.80153 | 11.10678 | 9.885 up | 0.159 | -14.533 |

| SYMBOL | DEFINITION | Mean WAT16 Control | Mean WAT16 KOKO | Fold change | P value | T value |
|---|---|---|---|---|---|---|
| Hbb-b2 | Mus musculus hemoglobin, beta adult minor chain (Hbb-b2), mRNA. | 8.01322 | 9.05344 | 2.056 up | 1 | -1.083 |
| Hspb7 | Mus musculus heat shock protein family, member 7 (cardiovascular) (Hspb7), mRNA. | 7.79921 | 8.90703 | 2.155 up | 1 | -6.342 |
| Igh-6 | | 13.20294 | 12.05877 | 2.210 down | 1 | 1.978 |
| IGHV1S120_ AF025443_Ig_ heavy_variable 1S120_8 | | 7.69711 | 6.42558 | 2.414 down | 1 | 1.752 |
| IGHV1S35_ M12376_Ig_ heavy_variable_ 1S35_13 | | 8.03404 | 6.51897 | 2.858 down | 1 | 1.811 |

FIG. 3B

| SYMBOL | DEFINITION | Mean WAT16 Control | Mean WAT16 KOKO | Fold change | P value | T value |
|---|---|---|---|---|---|---|
| IGHV1S36_M13788_Ig_heavy_variable_IS36_40 | | 7.15369 | 6.09972 | 2.076 down | 1 | 1.887 |
| IGHV1S4_J00534_Ig_heavy_variable_IS4_10 | | 7.42587 | 6.37569 | 2.070 down | 1 | 1.569 |
| IGHV1S6_J00536_Ig_heavy_variable_IS6_10 | | 7.47585 | 6.17225 | 2.468 down | 1 | 1.952 |
| Igh-VJ558 | PREDICTED: Mus musculus immunoglobulin heavy chain (J558 family) (Igh-VJ558), mRNA. | 10.03092 | 8.71519 | 2.489 down | 1 | 1.336 |

| SYMBOL | DEFINITION | Mean WAT16 Control | Mean WAT16 KOKO | Fold change | P value | T value |
|---|---|---|---|---|---|---|
| IGKV1-99_AJ231207_Ig_kappa_variable_1-99_1 | | 8.18447 | 6.82303 | 2.569 down | 1 | 2.277 |
| IGKV3-2_X16954_Ig_kappa_variable_3-2_18 | | 10.35398 | 8.49428 | 3.629 down | 1 | 0.98 |
| Igk-V38 | | 7.4376 | 6.3587 | 2.112 down | 1 | 1.406 |
| IGKV4-73_AJ231216_Ig_kappa_variable_4-73_18 | | 8.14829 | 7.08545 | 2.089 down | 1 | 1.762 |
| IGKV9-120_V00804$J00566_Ig_kappa_variable_9-120_12 | | 8.61857 | 6.17032 | 5.457 down | 1 | 9.263 |
| Igl-V1 | | 10.61743 | 9.41265 | 2.305 down | 1 | 1.452 |

FIG. 3C

| SYMBOL | DEFINITION | Mean WAT16 Control | Mean WAT16 KOKO | Fold change | P value | T value |
|---|---|---|---|---|---|---|
| LOC100046552 | PREDICTED: Mus musculus similar to Unknown (protein for MGC:103328) (LOC100046552), mRNA | 7.75137 | 6.32051 | 2.696 down | 1 | 2.286 |
| LOC100046793 | PREDICTED: Mus musculus similar to light chain of the monoclonal antibody MST2 (LOC100046793), mRNA | 9.51718 | 8.18892 | 2.511 down | 1 | 1.543 |
| LOC100047070 | PREDICTED: Mus musculus similar to [Human Ig rearranged gamma chain mRNA, V-J-C region and complete cds.], gene product (LOC100047070), mRNA. | 9.36242 | 6.75524 | 6.093 down | 1 | 2.735 |

| SYMBOL | DEFINITION | Mean WAT16 Control | Mean WAT16 KOKO | Fold change | P value | T value |
|---|---|---|---|---|---|---|
| LOC100047162 | PREDICTED: Mus musculus similar to immunoglobulin kappa-chain (LOC100047162), mRNA. | 10.04244 | 8.53579 | 2.841 down | 1 | 1.694 |
| LOC100047788 | PREDICTED: Mus musculus similar to gamma-2a immuno-globulin heavy chain (LOC100047788), misc RNA. | 8.82233 | 7.5965 | 2.338 down | 1 | 1.408 |
| LOC213684 | | 8.17375 | 7.13687 | 2.051 down | 1 | 1.772 |
| LOC232060 | | 7.85299 | 6.4274 | 2.686 down | 1 | 1.496 |
| LOC243431 | PREDICTED: Mus musculus similar to Ig kappa chain V-V region MOPC 41 precursor (LOC243431), mRNA | 8.82063 | 7.81979 | 2.001 down | 1 | 1.768 |

FIG. 3D

| SYMBOL | DEFINITION | Mean WAT16 Control | Mean WAT16 KOKO | Fold change | P value | T value |
|---|---|---|---|---|---|---|
| LOC384413 | | 8.89026 | 7.62809 | 2.398 down | 1 | 1.351 |
| LOC385291 | | 8.34942 | 6.94963 | 2.638 down | 1 | 2.006 |
| LOC546905 | PREDICTED: Mus musculus similar to Ig kappa chain V-IV region precursor (LOC546905), mRNA. | 8.2583 | 7.0291 | 2.344 down | 1 | 1.67 |
| LOC626583 | PREDICTED: Mus musculus similar to Ig kappa chain V-III region PC 7132 (LOC626583), mRNA. | 9.23851 | 7.51252 | 3.308 down | 1 | 1.068 |
| LOC636752 | PREDICTED: Mus musculus similar to Ig kappa chain V-VI region NQ2-6.1 (LOC636752), mRNA. | 8.85842 | 7.79226 | 2.093 down | 1 | 1.249 |

| SYMBOL | DEFINITION | Mean WAT16 Control | Mean WAT16 KOKO | Fold change | P value | T value |
|---|---|---|---|---|---|---|
| LOC636944 | PREDICTED: Mus musculus similar to Ig kappa chain V-V region K2 precursor (LOC636944), mRNA. | 9.79257 | 8.33555 | 2.745 down | 1 | 1.438 |
| LOC637227 | PREDICTED: Mus musculus similar to Ig kappa chain V-V region MPC11 precursor (LOC637227), mRNA. | 9.81025 | 8.35834 | 2.735 down | 1 | 1.844 |
| LOC637785 | PREDICTED: Mus musculus similar to Ig heavy chain V region 3 precursor (LOC637785), mRNA. | 7.90401 | 6.38126 | 2.873 down | 1 | 1.898 |

FIG. 3E

| SYMBOL | DEFINITION | Mean WAT16 Control | Mean WAT16 KOKO | Fold change | P value | T value |
|---|---|---|---|---|---|---|
| LOC669053 | PREDICTED: Mus musculus similar to Ig kappa chain V-V region MPC11 precursor (LOC669053), mRNA. | 8.75773 | 7.70692 | 2.071 down | 1 | 1.383 |
| LOC672339 | PREDICTED: Mus musculus similar to Ig kappa chain V-IV region S107B precursor (LOC672339), mRNA. | 7.36543 | 6.32982 | 2.049 down | 1 | 1.983 |
| LOC672342 | PREDICTED: Mus musculus similar to Ig kappa chain V-IV region S107B precursor (LOC672342), mRNA. | 8.88777 | 7.44854 | 2.711 down | 1 | 1.801 |

| SYMBOL | DEFINITION | Mean WAT16 Control | Mean WAT16 KOKO | Fold change | P value | T value |
|---|---|---|---|---|---|---|
| LOC672427 | PREDICTED: Mus musculus similar to Ig kappa chain V-IV region precursor (LOC672427), mRNA. | 9.52332 | 6.96724 | 5.881 down | 1 | 2.764 |
| LOC676136 | PREDICTED: Mus musculus similar to Ig kappa chain V-V region MPC11 precursor (LOC676136), mRNA. | 8.4352 | 7.30662 | 2.186 down | 1 | 1.599 |
| LOC676222 | PREDICTED: Mus musculus similar to Ig kappa chain V-III region PC 7043 (LOC676222), mRNA. | 9.88436 | 7.87653 | 4.021 down | 1 | 1.443 |

FIG. 3F

| SYMBOL | DEFINITION | Mean WAT16 Control | Mean WAT16 KOKO | Fold change | P value | T value |
|---|---|---|---|---|---|---|
| LOC677643 | PREDICTED: Mus musculus similar to monoclonal antibody BBK-2 heavy chain (LOC677643), misc RNA | 8.26474 | 6.47333 | 3.461 down | 1 | 1.857 |
| Lyve1 | Mus musculus lymphatic vessel endothelial hyaluronan receptor 1 (Lyve1), mRNA. | 9.27139 | 10.53226 | 2.396 up | 1 | -1.836 |
| Mcpt4 | Mus musculus mast cell protease 4 (Mcpt4), mRNA. | 9.83256 | 8.74891 | 2.119 down | 1 | 3.423 |
| Mmp3 | Mus musculus matrix metallopeptidase 3 (Mmp3), mRNA. | 8.33184 | 7.00739 | 2.504 down | 1 | 2.689 |
| Pdk4 | | 8.3495 | 9.35963 | 2.014 up | 1 | -4.373 |

| SYMBOL | DEFINITION | Mean WAT16 Control | Mean WAT16 KOKO | Fold change | P value | T value |
|---|---|---|---|---|---|---|
| Picalm | Mus musculus phosphatidylinositol binding clathrin assembly protein (Picalm), mRNA. | 9.90058 | 8.8886 | 2.016 down | 1 | 2.195 |
| Prm1 | Mus musculus protamine 1 (Prm1), mRNA | 6.49514 | 7.56824 | 2.103 up | 1 | -1.966 |
| Prps1 | Mus musculus phosphoribosyl pyrophosphate synthetase 1 (Prps1), mRNA | 12.13229 | 11.13167 | 2.000 down | 1 | 2.814 |
| Psmc1 | Mus musculus protease (prosome, macropain) 26S subunit, ATPase 1 (Psmc1), mRNA. | 7.84929 | 6.82646 | 2.031 down | 1 | 1.79 |

FIG. 3G

| SYMBOL | DEFINITION | Mean WAT16 Control | Mean WAT16 KOKO | Fold change | P value | T value |
|---|---|---|---|---|---|---|
| Serpina3g | Mus musculus serine (or cysteine) peptidase inhibitor, clade A, member 3G (Serpina3g), mRNA. | 8.90332 | 7.87141 | 2.044 down | 1 | 1.313 |
| Spp1 | Mus musculus secreted phosphoprotein 1 (Spp1), mRNA. | 9.28061 | 8.06861 | 2.316 down | 1 | 1.349 |
| Wisp2 | Mus musculus WNT1 inducible signaling pathway protein 2 (Wisp2), mRNA. | 9.79282 | 11.21909 | 2.687 up | 1 | -1.68 |

NOTE: The protein information displayed is the one corresponding to the Gene Name shown.
n.a. means data is not available.

| SYMBOL | DEFINITION | Mean Liver Control | Mean Liver KOKO | Fold change | P value | T value |
|---|---|---|---|---|---|---|
| 1110030E23Rik | | 8.23393 | 7.16845 | 2.092 down | 1 | 2.835 |
| 1190007I07Rik | PREDICTED: Mus musculus RIKEN cDNA1190007I07 gene (1190007I07Rik), mRNA. | 6.8827 | 8.16354 | 2.429 up | 1 | -5.668 |
| 1700080G11Rik | | 8.91586 | 7.85442 | 2.087 down | 1 | 2.933 |
| 1810023F06Rik | Mus musculus RIKEN cDNA 1810023F06 gene (1810023F06Rik), mRNA. | 8.39048 | 6.48467 | 3.747 down | 1 | 2.168 |
| 2010109N18Rik | | 10.11315 | 8.68352 | 2.693 down | 0.219 | 11.558 |
| 5033411D12Rik | Mus musculus RIKEN cDNA 5033411D12 gene (5033411 D 12Rik), mRNA. | 7.42659 | 8.59524 | 2.248 up | 1 | -1.38 |
| 9030619P08Rik | Mus musculus RIKEN cDNA 9030619P08 gene (9030619P08Rik), tRNA. | 8.56409 | 7.0242 | 2.907 down | 1 | 3.824 |
| 9626965_344 | | 6.22356 | 7.41918 | 2.290 up | 1 | -2.206 |

| SYMBOL | DEFINITION | Mean Liver Control | Mean Liver KOKO | Fold change | P value | T value |
|---|---|---|---|---|---|---|
| Aacs | Mus musculus acetoacetyl-CoA synthetase (Aacs), mRNA. | 9.96758 | 11.05129 | 2.119 up | 1 | -3.107 |
| Aatk | Mus musculus apoptosis-associated tyrosine kinase (Aatk), mRNA. | 9.98967 | 8.53276 | 2.745 down | 1 | 2.514 |
| Adh7 | Mus musculus alcohol dehydrogenase 7 (class IV), mu or sigma polypeptide (Adh7), mRNA. | 6.84709 | 8.24468 | 2.634 up | 1 | -3.041 |
| Agxt2l1 | Mus musculus alanine-glyoxylate aminotransferase2-like 1 (Agxt2ll), mRNA. | 8.78432 | 10.19931 | 2.666 up | 1 | -2.517 |
| Ang1 | | 11.11595 | 12.18591 | 2.099 up | 1 | -1.1 |
| Asns | Mus musculus asparagine synthetase (Asns), mRNA. | 7.66068 | 8.80018 | 2.203 up | 1 | -3.212 |

FIG. 4A

| SYMBOL | DEFINITION | Mean Liver Control | Mean Liver KOKO | Fold change | P value | T value |
|---|---|---|---|---|---|---|
| B3galt1 | Mus musculus UDP-Gal:betaGlcNAc beta 1,3-galactosyltransferase, polypeptide 1 (B3galt1), mRNA. | 8.73549 | 7.5326 | 2.302 down | 1 | 3.338 |
| Bat5 | Mus musculus HLA-B associated transcript 5 (Bat5), mRNA. | 9.72779 | 8.6304 | 2.139 down | 1 | 1.479 |
| Bcl6 | Mus musculus B-cell leukemia/ lymphoma 6 (Bcl6), mRNA. | 10.0696 | 8.47989 | 3.009 down | 1 | 3.779 |
| C730036D15Rik | Mus musculus RIKEN cDNA C730036D15 gene (C730036D15Rik), mRNA. | 8.93078 | 7.68218 | 2.376 down | 1 | 1.908 |

| SYMBOL | DEFINITION | Mean Liver Control | Mean Liver KOKO | Fold change | P value | T value |
|---|---|---|---|---|---|---|
| Cd74 | Mus musculus CD74 antigen (invariant polypeptide of major histocompatibility complex, class II antigen-associated) (Cd74), transcript variant 1, mRNA. | 10.57412 | 9.52276 | 2.072 down | 1 | 1.609 |
| Chi3l1 | Mus musculus chitinase 3-like 1 (Chi3l1), mRNA. | 8.23721 | 6.80649 | 2.695 down | 1 | 1.817 |
| Cish | Mus musculus cytokine inducible SH2-containing protein (Cish), mRNA. | 9.16556 | 10.18372 | 2.025 up | 1 | -1.235 |
| Cml4 | Mus musculus camello-like 4 (Cml4), mRNA | 10.62652 | 9.196 | 2.695 down | 1 | 5.071 |
| Crygn | | 8.40171 | 7.00743 | 2.628 down | 1 | 4.283 |
| Crym | Mus musculus crystallin, mu (Crym), mRNA. | 8.14695 | 7.05598 | 2.130 down | 1 | 2.301 |

FIG. 4B

| SYMBOL | DEFINITION | Mean Liver Control | Mean Liver KOKO | Fold change | P value | T value |
|---|---|---|---|---|---|---|
| Cxcl1 | Mus musculus chemokine (C-X-C motif) ligand 1 (Cxcl1), mRNA. | 11.87173 | 10.09446 | 3.427 down | 1 | 3.543 |
| Cyp2b9 | Mus musculus cytochrome P450, family 2, subfamily b, polypeptide 9 (Cyp2b9), mRNA | 6.90022 | 8.28365 | 2.608 up | 1 | -1.319 |
| Cyp2c29 | Mus musculus cytochrome P450, family 2, subfamily c, polypeptide 29 (Cyp2c29), mRNA. | 8.59463 | 9.73876 | 2.210 up | 1 | -3.169 |
| D17H6S56E-5 | Mus musculus DNA segment, Chr 17, human D6856E 5 (D17H6856E-5), mRNA. | 8.09796 | 7.00864 | 2.127 down | 1 | 1.473 |
| Dct | Mus musculus dopachrome tautomerase (Dct), mRNA. | 8.45427 | 6.77009 | 3.213 down | 1 | 1.499 |

| SYMBOL | DEFINITION | Mean Liver Control | Mean Liver KOKO | Fold change | P value | T value |
|---|---|---|---|---|---|---|
| Dio1 | Mus musculus deiodinase, iodothyronine, type 1 (Dio1), mRNA. | 10.68808 | 9.22481 | 2.757 down | 1 | 4.989 |
| Dnaic1 | Mus musculus dynein, axonemal, intermediate chain 1 (Dnaic 1), mRNA. | 6.418 | 7.47935 | 2.086 up | 1 | -2.222 |
| Eif4e3 | Mus musculus eukaryotic translation initiation factor 4E member 3 (Eif4e3), mRNA | 8.96201 | 7.56863 | 2.626 down | 1 | 4.207 |
| Fcer1g | Mus musculus Fc receptor, IgE, high affinity I, gamma polypeptide (Fcer1g), mRNA. | 9.64215 | 7.22341 | 5.347 down | 1 | 2.317 |
| Gbp1 | Mus musculus guanylate nucleotide binding protein 1 (Gbp1), mRNA. | 9.16202 | 7.10076 | 4.173 down | 1 | 3.46 |

FIG. 4C

| SYMBOL | DEFINITION | Mean Liver Control | Mean Liver KOKO | Fold change | P value | T value |
|---|---|---|---|---|---|---|
| Gdpd3 | Mus musculus glycero-phosphodiester phosphodiesterase domain containing 3 (Gdpd3), mRNA. | 6.76194 | 10.44065 | 12.805 up | 0.197 | -10.16 |
| Gna14 | Mus musculus guanine nucleotide binding protein, alpha 14 (Gna14), mRNA. | 8.40966 | 7.09945 | 2.479 down | 1 | 4.926 |
| Guca2a | Mus musculus guanylate cyclase activator 2a (guanylin) (Guca2a), mRNA. | 7.72389 | 6.12155 | 3.036 down | 1 | 1.391 |
| Guca2b | Mus musculus guanylate cyclase activator 2b (retina) (Guca2b), mRNA. | 7.5937 | 6.10386 | 2.808 down | 1 | 1.359 |
| H2-Aa | Mus musculus histocompatibility 2, class II antigen A, alpha (H2-Aa), mRNA. | 9.73023 | 8.01227 | 3.289 down | 1 | 1.948 |

| SYMBOL | DEFINITION | Mean Liver Control | Mean Liver KOKO | Fold change | P value | T value |
|---|---|---|---|---|---|---|
| H2-Ab1 | Mus musculus histocompatibility 2, class II antigen A, beta 1 (H2-Ab1), mRNA. | 10.33234 | 9.03565 | 2.456 down | 1 | 1.955 |
| H2-Eb1 | Mus musculus histocompatibility 2, class II antigen E beta (H2-Eb1), mRNA. | 9.95376 | 8.88602 | 2.096 down | 1 | 1.889 |
| H2-K1 | Mus musculus histocompatibility 2, K1, K region (H2-K1), transcript variant 1, mRNA | 10.6928 | 8.93512 | 3.381 down | 1 | 1.943 |
| Hsd17b6 | Mus musculus hydroxysteroid (17-beta) dehydrogenase 6 (Hsd17b6), mRNA. | 9.63973 | 10.81119 | 2.252 up | 1 | -2.308 |
| Hsd3b5 | Mus musculus hydroxy-delta-5-steroid dehydrogenase, 3 beta- and steroid delta-isomerase 5 (Hsd3b5), mRNA. | 8.43517 | 9.47896 | 2.061 up | 1 | -1.037 |

FIG. 4D

| SYMBOL | DEFINITION | Mean Liver Control | Mean Liver KOKO | Fold change | P value | T value |
|---|---|---|---|---|---|---|
| Ifi47 | Mus musculus interferon gamma inducible protein 47 (Ifi47), mRNA. | 9.63782 | 8.62744 | 2.014 down | 1 | 1.967 |
| Igfbp2 | Mus musculus insulin-like growth factor binding protein 2 (Igfbp2), mRNA. | 10.16846 | 11.58321 | 2.666 up | 1 | -3.298 |
| Lcn13 | Mus musculus lipocalin 13 (Lcn13), mRNA. | 9.19861 | 6.72936 | 5.537 down | 1 | 3.18 |
| Lcn2 | Mus musculus lipocalin 2 (Lcn2), mRNA | 13.20497 | 11.41781 | 3.451 down | 1 | 1.749 |
| Lgals1 | Mus musculus lectin, galactose binding, soluble 1 (Lgals1), mRNA. | 9.33145 | 8.32047 | 2.015 down | 1 | 1.926 |
| LOC 100048733 | PREDICTED: Mus musculus similar to WAP four-disulfide core domain 2 (LOC100048733), mRNA. | 8.96504 | 7.07356 | 3.710 down | 1 | 3.083 |

| SYMBOL | DEFINITION | Mean Liver Control | Mean Liver KOKO | Fold change | P value | T value |
|---|---|---|---|---|---|---|
| LOC239727 | | 8.55837 | 7.10013 | 2.747 down | 1 | 3.148 |
| LOC383483 | | 7.62396 | 6.37369 | 2.378 down | 1 | 2.544 |
| LOC668631 | PREDICTED: Mus musculus hypothetical protein LOC668631 (LOC668631), mRNA. | 9.4466 | 12.91397 | 11.060 up | 0.151 | -11.504 |
| Ly6d | Mus musculus lymphocyte antigen 6 complex, locus D (Ly6d), mRNA. | 8.02623 | 6.68571 | 2.532 down | 1 | 2.181 |
| Marco | Mus musculus macrophage receptor with collagenous structure (Marco), mRNA. | 7.00234 | 9.27273 | 4.824 up | 1 | -3.238 |
| Mgst1 | Mus musculus microsomal glutathione S-transferase 1 (Mgst1), mRNA. | 14.5636 | 13.06069 | 2.834 down | 1 | 1.616 |
| Myom2 | | 7.70892 | 9.82397 | 4.332 up | 1 | -6.299 |

FIG. 4E

| SYMBOL | DEFINITION | Mean Liver Control | Mean Liver KOKO | Fold change | P value | T value |
|---|---|---|---|---|---|---|
| Nlrp12 | PREDICTED: Mus musculus NLR family, pyrin domain containing 12, transcript variant 2 (Nlrp12), mRNA. | 6.18305 | 8.49798 | 4.975 up | 0.0683 | -15.46 |
| Plscr1 | Mus musculus phospholipid scramblase 1 (Plscr1), mRNA. | 9.41802 | 8.39689 | 2.029 down | 1 | 2.285 |
| Psmb9 | Mus musculus proteasome (prosome, macropain) subunit, beta type 9 (large multifunctional peptidase 2) (Psmb9), mRNA. | 10.01348 | 8.44519 | 2.965 down | 1 | 3.848 |
| Rarres1 | PREDICTED: Mus musculus retinoic acid receptor responder (tazarotene induced) 1 (Rarres1), mRNA | 10.46063 | 9.23203 | 2.343 down | 1 | 2.603 |

| SYMBOL | DEFINITION | Mean Liver Control | Mean Liver KOKO | Fold change | P value | T value |
|---|---|---|---|---|---|---|
| Rpl29 | Mus musculus ribosomal protein L29 (Rpl29), mRNA. | 6.72825 | 7.84738 | 2.172 up | 1 | -1.634 |
| Rsad2 | Mus musculus radical S-adenosyl methionine domain containing 2 (Rsad2), mRNA. | 9.3529 | 8.23893 | 2.164 down | 1 | 4.273 |
| S100a8 | Mus musculus S100 calcium binding protein A8 (calgranulin A) (S100a8), mRNA. | 9.78326 | 7.93574 | 3.598 down | 1 | 2.96 |
| S100a9 | Mus musculus S100 calcium binding protein A9 (calgran-ulin B) (S100a9), mRNA. | 8.65534 | 7.15993 | 2.819 down | 1 | 3.334 |
| Saa2 | Mus musculus serum amyloid A 2 (Saa2), mRNA. | 11.95262 | 10.40564 | 2.922 down | 1 | 2.024 |

FIG. 4F

| SYMBOL | DEFINITION | Mean Liver Control | Mean Liver KOKO | Fold change | P value | T value |
|---|---|---|---|---|---|---|
| Saa3 | Mus musculus serum amyloid A 3 (Saa3), mRNA. | 11.77073 | 10.39814 | 2.589 down | 1 | 1.472 |
| Scd1 | Mus musculus stearoyl-Coenzyme A desaturase 1 (Scd1), mRNA. | 12.63164 | 13.77321 | 2.206 up | 1 | -1.142 |
| Serpina12 | Mus musculus serine (or cysteine) peptidase inhibitor, clade A (alpha-1 antiproteinase, antitrypsin), member 12 (Serpina12), mRNA. | 9.53586 | 6.76683 | 6.816 down | 1 | 3.279 |
| Slco1a1 | Mus musculus solute carrier organic anion transporter family, member 1a1 (Slco1a1), mRNA | 7.9883 | 9.03161 | 2.060 up | 1 | -1.6 |
| Smpd3 | Mus musculus sphingomyelin phosphodiesterase 3, neutral (Smpd3), mRNA. | 7.38871 | 6.33427 | 2.076 down | 1 | 2.708 |

| SYMBOL | DEFINITION | Mean Liver Control | Mean Liver KOKO | Fold change | P value | T value |
|---|---|---|---|---|---|---|
| Spink3 | Mus musculus serine peptidase inhibitor, Kazal type 3 (Spink3), mRNA. | 8.08731 | 6.57677 | 2.849 down | 1 | 1.822 |
| Them4 | Mus musculus thioesterase superfamily member 4 (Them4), mRNA. XM_918865 XM_972946 XM_972982 XM_973023 XM_993608 | 7.49515 | 8.78197 | 2.439 up | 1 | -2.798 |
| Tlr2 | Mus musculus toll-like receptor 2 (Tlr2), mRNA | 8.85665 | 7.83416 | 2.031 down | 1 | 1.281 |
| Tm7sf3 | | 8.04052 | 6.9185 | 2.176 down | 1 | 3.151 |
| Ubd | Mus musculus ubiquitin D (Ubd), mRNA. | 10.11391 | 7.56332 | 5.858 down | 1 | 1.677 |
| Wfdc2 | Mus musculus WAP four-disulfide core domain 2 (Wfdc2), mRNA. | 11.21058 | 9.00013 | 4.628 down | 1 | 3.506 |

FIG. 4G

| ID | Molecules in Network | Score | Focus Molecules | Top Functions |
|----|----------------------|-------|-----------------|---------------|
| 1 | Akt, ANGPTLI, CCU, CCL27, CD74, CISH, CXCL1, FCERIG, heparin, HRH1, IGFBP2, IGM, INSRR, LCN2, NFkB, P38 MAPK, PPP1R13L, RAGE, RPL29, RSAD2, S100A8, S100A9, SAA2, SOCS6, STAP2, STAT5a/b, THEM4, TLR2, TLR5, TLR6, TLR7, TLR10, TOLLIP, ULBP1, VPREB1 (includes EG:7441) | 27 | 13 | Immune Response, Cellular Movement, Hematological System Development and Function |
| 2 | ADH7, BATS, BCL6, C19ORF10, CCL24, CCRN4L (includes EG:25819), CD58, CHI3L1, CRIP1, DIOI, EMP 1, ERBB2, GBP 1 (includes EG: 14468), GBP 1 (includes EG:2633), GDPD3, GUCA2A,1FI203, IL4, IL1B, IL1F5, IL1RN, ISG20, JUN, LGALSI, MAP3K14, MARCO, MBD3 (includes EG:53615), NLRP12, NNMT, PLSCR1, PTBP2, SAA4, TREM2, UBD, USP2 | 27 | 13 | Skeletal and Muscular Disorders, Cell-To-Cell Signaling and Interaction, Hematological System Development and Function |
| 3 | AACS, AATK, ACADS, ACSS2, ADIPOR2, ASNS, B3GALT1, CRYM, cyclic AMP, CYP4A14, DCT, FADS1, fatty acid, GK, HSD17B11, KCNK10, LY6D, MC1R, MEF2C, MGLL, MLYCD, MYOM2, P2RY1 1, PLS3, PPARA, PSMB9, RARRESI, retinoic acid, RN5S, SERPINA12, SKIP, SLC27A, SLC2A4, SMPD3, SREBFI | 24 | 12 | Lipid Metabolism, Small Molecule Biochemistry, Amino Acid Metabolism |
| 4 | 3-alpha,17-beta-androstanediol, 3-beta,l7-beta-androstanediol, androsterone, beta-estradiol, CCR1, CCR2, CRHRI, CSF3R, DDR1, EFNA1, EPOR, GNA14, GST, GSTM3 (includes EG:14864), GSTM3 (includes EG:2947), GSTT1, HAS2, HSD17B6, IFNGR2,1L24, KPNA4, LEPR, MGST1, MUC1, OPRD1, PIAS3, SERPINA3, SERPINB5, SLC6A4, SOCS2, STAT3, TACRI, VAV3, WFDC2, ZNF148 | 6 | 4 | Cellular Movement, Gene Expression, Cellular Development |
| 5 | NFYB, TM7SF3 | 2 | 1 | Gene Expression |
| 6 | GUCA, GUCA2B, GUCY2C | 2 | 1 | Nucleic Acid Metabolism, Small Molecule Biochemistry, Cell Signaling |

| Gene Name | Description | Refseq RNA | Entrez Gene | En-sembl Chr | WAT2 Control | WAT2 SirT1 koko | Fold change (WAT2SirT1 koko/Wat2 Control) |
|---|---|---|---|---|---|---|---|
| Gad2 | Glutamic acid decarboxylase 2 | | 14417 | 2 | 4572.296948 | 121988.3476 | 26.679883 |
| Igfbp1 | Insulin-like growth factor binding protein 1 | NM_008341.3 | 16006 | 11 | 1174.856133 | 97713.67237 | 83.17075566 |
| Htr2c | 5-hydroxytryptamine (serotonin) receptor 2C | NM_008312.3 | 15560 | X | 2995.276324 | 21310.70679 | 7.114771555 |
| Bdnf | Brain derived neurotrophic factor | NM_001048139.1 NM_001048141.1 NM_001048142.1 NM_007540.4 | 12064 | 2 | 90.75513612 | 384.7842191 | 4.239806534 |
| Hnf4a | Hepatic nuclear factor 4, alpha | NM_008261.2 | 15378 | 2 | 183.5928911 | 21785.9261 | 118.6643228 |
| Gnb3 | Guanine nucleotide binding protein, beta 3 | NM_013530.1 | 14695 | 6 | 759.2106327 | 1650.68008 | 2.174205693 |
| Rrad | Ras-related associated with diabetes | NM_019662.2 | 56437 | 8 | 20.11935831 | 45.35597843 | 2.25434518 |
| Pon1 | Paraoxonase 1 | NM_011134.2 | 18979 | 6 | 462.1801173 | 139.9247948 | 0.30274949 |

| Gene Name | Description | Refseq RNA | Entrez Gene | En-sembl Chr | WAT2 Control | WAT2 SirT1 koko | Fold change (WAT2SirT1 koko/Wat2 Control) |
|---|---|---|---|---|---|---|---|
| Iapp | Islet amyloid of polypeptide | NM_010491.1 | 15874 | 6 | 215066.5138 | 663.53595 | 0.003085259 |
| Ren1 | Renin 1 structural | NM_031192.2 NM_031193.2 | 19701 | 1 | n.a. | n.a. | n.a. |
| Ucp2 | Uncoupling protein 2 (mitochondrial, proton carrier) | NM_011671.3 | 22228 | 7 | 140.4419757 | 69.80579107 | 0.497043642 |
| Prkaa2 | Protein kinase, AMP-activated, alpha 2 catalytic subunit | NM_178143.1 | 108079 | 4 | 54.50589581 | 37.53628121 | 0.688664605 |
| Cd68 | CD68 antigen | NM_009853.1 | 12514 | 11 | 22.81379244 | 16.62873851 | 0.728889708 |
| Atp2a3 | ATPase, Ca++ transporting, ubiquitous | NM_016745.2 | 53313 | 11 | 51.74710999 | 86.04126447 | 1.662725986 |
| Cyp2e1 | Cytochrome P450, family 2, subfamily e, polypeptide 1 | NM_021282.2 | 13106 | 7 | 0.182975626 | 0.093834731 | 0.512826397 |
| Drd2 | Dopamine receptor 2 | NM_010077.2 | 13489 | 9 | 15959.34019 | 2711.600303 | 0.169906793 |

FIG. 6A

| Gene Name | Description | Refseq RNA | Entrez Gene | En-sembl Chr | WAT2 Control | WAT2 SirT1 koko | Fold change (WAT2SirT1 koko/Wat2 Control) |
|---|---|---|---|---|---|---|---|
| Sim1 | Single-minded homolog (Drosophila) | NM_011376.3 | 20464 | 10 | n.a | n.a | n.a |
| Retnlg | Resistin like gamma | NM_181596.3 | 245195 | 16 | 372.4521776 | 549.5541457 | 1.475502571 |
| Kcnb1 | Potassium voltage gated channel, Shab-related subfamily, member 1 | NM_008420.3 | 16500 | 2 | 2.555584664 | 5.086322085 | 1.990277277 |
| Fbp2 | Fructose bisphosphatase 2 | NM_007994.3 | 14120 | 13 | 74.7197844 | 329.498211 | 4.409785355 |
| Dgat2 | Diacylglycerol O-acyltransferase 2 | NM_026384.3 | 67800 | 7 | 0.034342488 | 0.066228997 | 1.9284857 |
| Bbs2 | Bardet-Biedl syndrome 2 homolog (human) | NM_026116.2 | 67378 | 8 | 146.1330193 | 75.00239822 | 0.513247441 |
| Htr2a | 5-hydroxytryptamine (serotonin) receptor 2A | NM_172812.2 | 15558 | 14 | 494.7721163 | 870.2468169 | 1.758884117 |
| Prkcm | Protein kinase C, mu | NM_008858.3 | 18760 | 12 | 12.71595038 | 23.93878161 | 1.882579036 |

| Gene Name | Description | Refseq RNA | Entrez Gene | En-sembl Chr | WAT2 Control | WAT2 SirT1 koko | Fold change (WAT2SirT1 koko/Wat2 Control) |
|---|---|---|---|---|---|---|---|
| Tcf7l2 | Transcription factor 7-like 2, T-cell specific, HMG-box | NM_009333.2 | 21416 | 19 | 35.09827902 | 24.68180197 | 0.703219721 |
| Lepr | Leptin receptor | NM_010704.1 NM_146146.1 | 16847 | 4 | 151.4878615 | 79.30219105 | 0.523488749 |
| Pbef1 | Pre-B-cell colony-enhancing factor 1 | NM_021524.1 | 59027 | 12 | 1.899030909 | 1.82132303 | 0.959080245 |
| Cblb | Casitas B-lineage lymphoma b | NM_001033238.1 | 208650 | 16 | 6.445549633 | 4.108497309 | 0.637416131 |
| a | Nonagouti | NM_015770.3 | 50518 | 2 | 3175.819905 | 448.9319055 | 0.141359371 |
| Calm4 | Calmodulin 4 | NM_020036.4 | 80796 | 13 | 979.8909457 | 3619.879159 | 3.69416533 |
| Lpin3 | Lipin 3 | NM_022883.2 | 64899 | 2 | 62.35124175 | 40.2799733 | 0.646017179 |
| Npy2r | Neuropeptide Y receptor Y2 | NM_008731.3 | 18167 | 3 | 7058.751841 | 8754.195101 | 1.240190235 |
| Kif3a | Kinesin family member 3A | NM_008443.3 | 16568 | 11 | 17.16914613 | 22.75273108 | 1.325210404 |

FIG. 6B

| Gene Name | Description | Refseq RNA | Entrez Gene | Ensembl Chr | WAT2 Control | WAT2 SirT1 koko | Fold change (WAT2SirT1 koko/Wat2 Control) |
|---|---|---|---|---|---|---|---|
| Ptpn6 | Protein tyrosine phosphatase, non-receptor type 6 | NM_001077705.1 NM_013545.2 | 15170 | 6 | 172.6566854 | 99.89169428 | 0.57855677 |
| Clock | Circadian locomoter output cycles kaput | NM_007715.5 | 12753 | 5 | 17.04602428 | 28.32468137 | 1.6616591 |
| Calm1 | Calmodulin 1 | NM_009790.4 | 12313 | 12 | 52.14949536 | 11.99621868 | 0.230035182 |
| Pcsk1 | Proprotein convertase subtilisin/kexin type 1 | NM_013628.2 | 18548 | 13 | 547.8352877 | 291.0539571 | 0.531280046 |
| Pltp | Phospholipid transfer protein | NM_011125.2 | 18830 | 2 | 7.120375806 | 5.397337196 | 0.758012968 |
| Prkcz | Protein kinase C, zeta | NM_001039079.1 NM_008860.2 | 18762 | 4 | 225.8340771 | 345.8315838 | 1.531352523 |
| Serpine2 | Serine (or cysteine) peptidase inhibitor, clade E, member 2 | | 20720 | | 8.4489402 | 8.309535435 | 0.983500325 |
| Itgb3 | Integrin beta 3 | NM_016780.1 | 16416 | 11 | 256.3870151 | 438.2951249 | 1.709505939 |

| Gene Name | Description | Refseq RNA | Entrez Gene | Ensembl Chr | WAT2 Control | WAT2 SirT1 koko | Fold change (WAT2SirT1 koko/Wat2 Control) |
|---|---|---|---|---|---|---|---|
| Acacb | Acetyl-Coenzyme A carboxylase beta | NM_133904.2 | 100705 | 5 | 12.2370117 | 9.513398568 | 0.777428248 |
| Igfbp3 | Insulin-like growth factor binding protein 3 | NM_008343.2 | 16009 | 11 | 4.676815083 | 11.47723186 | 2.454070058 |
| Syk | Spleen tyrosine kinase | NM_011518.2 | 20963 | 13 | 20.67666191 | 22.62700642 | 1.094325889 |
| Apoa4 | Apolipoprotein A-IV | NM_007468.2 | 11808 | 9 | 4231.558473 | 1254.729641 | 0.296517146 |
| Ereg | Epiregulin | NM_007950.2 | 13874 | 5 | 1436.385607 | 2802.261396 | 1.950911637 |
| Phka1 | Phosphorylase kinase alpha 1 | NM_008832.2 NM_173021.3 | 18679 | X | 45.33085247 | 64.27001134 | 1.417798427 |
| Ucp3 | Uncoupling protein 3 (mitochondrial, proton carrier) | NM_009464.3 | 22229 | 7 | 8.750208458 | 11.88660508 | 1.358436789 |
| Hsd11b1 | Hydroxysteroid 11-beta Dehydrogenase 1 | | 15483 | | 3.054294947 | 2.420227761 | 0.792401455 |
| Apoa1 | Apolipoprotein A-1 | NM_009692.2 | 11806 | 9 | 76.12552603 | 48.14168796 | 0.632398756 |

FIG. 6C

| Gene Name | Description | Refseq RNA | Entrez Gene | En-sembl Chr | WAT2 Control | WAT2 SirT1 koko | Fold change (WAT2SirT1 koko/Wat2 Control) |
|---|---|---|---|---|---|---|---|
| Cacna1e | Calcium channel, voltage-dependent, R type, alpha 1 E subunit | NM_009782.3 | 12290 | 1 | 145.1489562 | 1180.43331 | 8.132564924 |
| Esr2 | Estrogen receptor 2 (beta) | NM_010157.3 NM_207707.1 | 13983 | 12 | 1213.123225 | 174.4542364 | 0.143805866 |
| Cckar | Cholecystokinin A receptor | NM_009827.1 | 12425 | 5 | 1743.27975 | 3170.744298 | 1.818838484 |
| 4932417H02Rik | RIKEN cDNA 4932417H02 gene | NM_028898.2 | 74370 | 11 | 620.673348 | 786.0829902 | 1.266500314 |
| Rps6ka3 | Ribosomal protein S6 kinase polypeptide 3 | NM_148945.1 | 110651 | X | 2.282924878 | 4.626761785 | 2.026681574 |
| Slc27a1 | Solute carrier family 27 (fatty acid trans-porter), member 1 | NM_011977.3 | 26457 | 8 | 1.205773884 | 0.652661943 | 0.541280543 |
| Igf1r | Insulin-like growth factor I receptor | NM_010513.2 | 16001 | 7 | 21.4342107 | 15.20144773 | 0.709214253 |
| Trip10 | Thyroid hormone receptor interactor 10 | NM_134125.3 | 106628 | 17 | 5.748618882 | 5.133834619 | 0.89305531 |

| Gene Name | Description | Refseq RNA | Entrez Gene | En-sembl Chr | WAT2 Control | WAT2 SirT1 koko | Fold change (WAT2SirT1 koko/Wat2 Control) |
|---|---|---|---|---|---|---|---|
| Mknk1 | MAP kinase-interacting serine/threonine kinase 1 | NM_021461.4 | 17346 | 4 | 25.81286528 | 35.89713554 | 1.39066838 |
| Ace | Angiotensin I converting enzyme (peptidyl-dipeptidase A) 1 | NM_009598.1 NM_207624.4 | 11421 | 11 | 20.38711019 | 19.94917005 | 0.978518773 |
| Crk1 | V-crk sarcoma virus CT10 oncogene homolog (avian)-like | NM_007764.4 | 12929 | 16 | 20.48345802 | 19.99858224 | 0.976328422 |
| Angptl4 | Angiopoietin-like 4 | NM_020581.1 | 57875 | 17 | 1.010196807 | 0.459246561 | 0.454610981 |
| Stxbp4 | Syntaxin binding protein 4 | | 20913 | 11 | 32.35292817 | 48.11219855 | 1.487104917 |
| Gck | Glucokinase | NM_010292.4 | 103988 | 11 | 335.5266121 | 752.9069789 | 2.243956073 |
| Cp | Ceruloplasmin | NM_001042611.1 NM_007752.2 | 12870 | 3 | 9.301861036 | 7.988346 | 0.858790082 |
| Atp2a2 | ATPase, Ca++ transporting, cardiac muscle, slow twitch 2 | NM_001110140.1 NM_009722.2 | 11938 | 5 | 3.026558815 | 5.032425194 | 1.662754799 |

FIG. 6D

| Gene Name | Description | Refseq RNA | Entrez Gene | En-sembl Chr | WAT2 Control | WAT2 SirT1 koko | Fold change (WAT2SirT1 koko/Wat2 Control) |
|---|---|---|---|---|---|---|---|
| Ikbkb | Inhibitor of kappaB kinase beta | NM_010546.1 | 16150 | 8 | 8.327996066 | 6.963443068 | 0.836148698 |
| Pfkp | Phosphofructokinase, platelet | NM_019703.3 | 56421 | 13 | 3.447358621 | 7.211487248 | 2.091887744 |
| Cav3 | Caveolin 3 | NM_007617.2 | 12391 | 6 | 1179.899599 | 1436.93872 | 1.217848299 |
| Trpv1 | Transient receptor potential cation channel, subfamily V, member 1 | NM_001001445.1 | 193034 | 11 | 46.14116058 | 45.2316532 | 0.980288589 |
| Pik3r1 | Phosphatidylinositol 3-kinase, regulatory subunit, polypeptide 1 (p85 alpha) | NM_001024955.1 NM_001077495.1 | 18708 | 13 | 0.772179087 | 0.727476133 | 0.942108049 |
| Tsc1 | Tuberous sclerosis 1 | NM_022887.3 | 64930 | 2 | 54.86622408 | 54.01577228 | 0.984499538 |
| Tnfrsf 11a | Tumor necrosis factor receptor superfamily, member 11 a | NM_009399.3 | 21934 | 1 | 54.34247569 | 34.45393413 | 0.634014805 |

| Gene Name | Description | Refseq RNA | Entrez Gene | En-sembl Chr | WAT2 Control | WAT2 SirT1 koko | Fold change (WAT2SirT1 koko/Wat2 Control) |
|---|---|---|---|---|---|---|---|
| Alox5ap | Arachidonate 5-lipoxygenase activating protein | | 11690 | | 9.410884913 | 9.310836721 | 0.989368886 |
| Nos3 | Nitric oxide synthase 3, endothelial cell | NM_008713.3 | 18127 | 5 | 2.777676116 | 3.039630211 | 1.094306926 |
| Irs3 | Insulin receptor substrate 3 | NM_010571.3 | 16369 | 5 | 18.19024901 | 22.96948845 | 1.26273634 |
| Vip | Vasoactive intestinal polypeptide | | 22353 | | 912.3391313 | 759.8889675 | 0.832901869 |
| Grb2 | Growth factor receptor bound protein 2 | NM_008163.3 | 14784 | 11 | 18.76159253 | 22.022782 | 1.173822636 |
| Pck2 | Phosphoenolpyruvate carboxykinase 2 (mitochondrial) | NM_028994.2 | 74551 | 14 | 22.55850237 | 15.57122802 | 0.69025983 |
| Socs2 | Suppressor of cytokine signaling 2 | NM_007706.3 | 216233 | 10 | 20.30974734 | 15.98968732 | 0.787291297 |
| Sh2b2 | SH2B adaptor protein 2 | NM_018825.3 | 23921 | 5 | 8.248795023 | 10.20316489 | 1.236927922 |

FIG. 6E

| Gene Name | Description | Refseq RNA | Entrez Gene | Ensembl Chr | WAT2 Control | WAT2 SirT1 koko | Fold change (WAT2SirT1 koko/Wat2 Control) |
|---|---|---|---|---|---|---|---|
| Pik3cd | Phosphatidylinositol 3-kinase catalytic delta polypepide | NM_001029837.1 NM_008840.2 | 18707 | 4 | 86.46194509 | 55.72295348 | 0.644479527 |
| Braf | Braf transforming gene | NM_139294.5 | 109880 | 6 | 8.27364116 | 9.349912228 | 1.13008433 |
| Ccr2 | Chemokine (C-C motif) receptor 2 | NM_009915.1 | 12772 | 9 | 5.51551036 | 4.18590283 | 0.758933001 |
| Akt3 | Thymoma viral proto-oncogene 3 | NM_011785.2 | 23797 | 1 | 21.6922739 | 17.72521009 | 0.817120887 |
| Phkg1 | Phosphorylase kinase gamma 1 | NM_011079.2 | 18682 | 5 | 15.17379858 | 12.5393514 | 0.826381827 |
| Ppara | Peroxisome proliferator activated receptor alpha | NM_011144.5 | 19013 | 15 | 11.30612296 | 11.09548497 | 0.981369565 |
| Prkaca | Protein kinase, cAMP dependent, catalytic, alpha | NM_008854.3 | 18747 | 8 | 0.888569414 | 1.444971284 | 1.626177158 |
| Bbs4 | Bardet-Biedl syndrome 4 homolog (human) | | 102774 | | 23.96910919 | 27.08640125 | 1.130054565 |

| Gene Name | Description | Refseq RNA | Entrez Gene | Ensembl Chr | WAT2 Control | WAT2 SirT1 koko | Fold change (WAT2SirT1 koko/Wat2 Control) |
|---|---|---|---|---|---|---|---|
| Cebpb | CCAAT/enhancer binding protein (C/EBP), beta | NM_009883.3 | 12608 | 2 | 1.759137663 | 1.070749365 | 0.608678552 |
| Mc3r | Melanocortin 3 receptor | NM_008561.3 | 17201 | 2 | 2875.665963 | 698.4290816 | 0.242875595 |
| Sdc3 | Syndecan 3 | NM_011520.3 | 20970 | 4 | 31.55995815 | 17.69579683 | 0.560704065 |
| Trpm4 | Transient receptor potential cation channel, subfamily M, member 4 | NM_175130.4 | 68667 | 7 | 41.14021382 | 36.7330764 | 0.892875194 |
| Ptgds | Prostaglandin D2 synthase (brain) | | 19215 | | 278.040144 | 782.5433271 | 2.814497633 |
| Ifng | Interferon gamma | | 15978 | | 409.1753392 | 691.3707805 | 1.689668742 |
| Ldlr | Low density lipoprotein receptor | NM_010700.2 | 16835 | 9 | 9.635539105 | 33.78082886 | 3.505857689 |
| Kcnj 11 | Potassium inwardly rectifying channel, subfamily J, member 11 | NM_010602.2 | 16514 | 7 | 1302.541287 | 1317.361723 | 1.011378093 |
| Insr | Insulin receptor | NM_010568.2 | 16337 | 8 | 8.419563186 | 6.932260273 | 0.823351535 |
| Lipc | Lipase, hepatic | NM_008280.2 | 15450 | 9 | 500.5690864 | 681.447556 | 1.361345665 |

FIG. 6F

| Gene Name | Description | Refseq RNA | Entrez Gene | En-sembl Chr | WAT2 Control | WAT2 SirT1 koko | Fold change (WAT2SirT1 koko/Wat2 Control |
|---|---|---|---|---|---|---|---|
| Prkcd | Protein kinase C, delta | NM_011103.2 | 18753 | 14 | 19.5672131 | 21.84579679 | 1.116449066 |
| Lep | Leptin | NM_008493.3 | 16846 | 6 | 0.213495473 | 0.513181412 | 2.403710977 |
| Glp1 | GATA-like 1 | NM_001103168.1 | 100009600 | 9 | 423.8198612 | 433.4286837 | 1.02267195 |
| Tnf | Tumor necrosis factor | NM_013693.2 | 21926 | 17 | 140.4270824 | 116.261033 | 0.827910336 |
| Apoe | Apolipoprotein E | NM_009696.2 | 11816 | 7 | 0.039256827 | 0.027991329 | 0.713030857 |
| Angptl6 | Angiopoietin-like 6 | NM_145154.2 | 70726 | 9 | 279.608302 | 533.301591 | 1.907316726 |
| Elk1 | ELK1, member of ETS oncogene family | NM_007922.4 | 13712 | X | 9.488620699 | 15.0966948 | 1.59103154 |
| Akt2 | Thymoma viral roto-oncogene 2 | | 11652 | | 0.598220969 | 0.707602388 | 1.182844508 |
| Fbp1 | Fructose bisphosphatase 1 | NM_019395.2 | 14121 | 13 | n.a. | n.a. | n.a. |
| Alb | Albumin | NM_009654.2 | 11657 | 5 | 62.9389143 | 174.0812272 | 2.765875915 |
| Kif5b | Kinesin family member 5B | NM_008448.2 | 16573 | 18 | 1.302237318 | 1.714430976 | 1.316527297 |
| Capn10 | Calpain 10 | NM_011796.2 | 23830 | 1 | 422.5248512 | 207.0438905 | 0.490015889 |
| Pax6 | Paired box gene 6 | | 18508 | | 569.5285628 | 384.9232012 | 0.675862856 |

| Gene Name | Description | Refseq RNA | Entrez Gene | En-sembl Chr | WAT2 Control | WAT2 SirT1 koko | Fold change (WAT2SirT1 koko/Wat2 Control |
|---|---|---|---|---|---|---|---|
| Obsp | Oxysterol binding protein | NM_001033174.1 | 76303 | 19 | 7.90332309 | 7.671830371 | 0.970709445 |
| Sstr2 | Somatostatin receptor 2 | NM_001042606.1 NM_009217.3 | 20606 | 11 | 380.7165265 | 823.8356925 | 2.163908407 |
| Foxc2 | Forkhead box C2 | NM_013519.2 | 14234 | 8 | 112.3339645 | 96.78354121 | 0.86156971 |
| Pomc1 | | | | | 181.819533 | 172.1933744 | 0.947056521 |
| Rbp4 | Retinol binding protein 4, plasma | NM_011255.2 | 19662 | 19 | 0.109437523 | 0.191035918 | 1.745616245 |
| Pygl | Liver glycogen phosphorylase | NM_133198.1 | 110095 | 12 | 1.861319072 | 2.590976305 | 1.392010829 |
| Adipor1 | Adiponectin receptor 1 | NM_028320.3 | 72674 | 1 | 1.611520328 | 1.648178871 | 1.022747801 |
| Agt | Angiotensinogen (serpin peptidase inhibitor, clade A, member 8) | NM_007428.3 | 11606 | 8 | 2.32387809 | 2.596681055 | 1.117391255 |
| Fasn | Fatty acid synthase | NM_007988.3 | 14104 | 11 | 0.158076124 | 0.396987592 | 2.511369725 |
| Hras1 | Harvey rat sarcoma virus oncogene 1 | NM_008284.1 | 15461 | 7 | 1.547508557 | 2.461880648 | 1.590867228 |

FIG. 6G

| Gene Name | Description | Refseq RNA | Entrez Gene | En-sembl Chr | WAT2 Control | WAT2 SirT1 koko | Fold change (WAT2SirT1 koko/Wat2 Control) |
|---|---|---|---|---|---|---|---|
| Shc1 | Src homology 2 domain-containing transforming protein C1 | NM_011368.4 | 20416 | 3 | 1.794219488 | 1.873973851 | 1.044450728 |
| Rapgef1 | Rap guanine nucleotide exchange factor (GEF) 1 | NM_001039086.1 NM_001039087.1 NM_054050.2 | 107746 | 2 | 3.960949718 | 4.876617512 | 1.231173799 |
| Calm3 | Calmodulin 3 | NM_009790.4 NM_007590.3 NM_007589.4 | 12315 | 17 | 2.055539915 | 2.794140994 | 1.359322178 |
| Cpe | Carboxypeptidase E | NM_013494.3 | 12876 | 8 | 9.583239253 | 10.1790204 | 1.062169078 |
| Glud1 | Glutamate dehydrogenase 1 | NM_008133.3 | 14661 | 14 | 1.567180538 | 1.63998523 | 1.046455842 |
| Stk11 | Serine/threonine kinase 11 | NM_011492.3 | 20869 | 10 | 3.004528042 | 2.446232995 | 0.814182115 |
| Hfe | Hemochromatosis | NM_010424.4 | 15216 | 13 | 1.209783917 | 1.843316521 | 1.523674183 |
| Pik3ca | Phosphatidylinositol3-kinase, catalytic, alpha polypeptide | NM_008839.1 | 18706 | 3 | 4.349614031 | 4.555848656 | 1.047414466 |

| Gene Name | Description | Refseq RNA | Entrez Gene | En-sembl Chr | WAT2 Control | WAT2 SirT1 koko | Fold change (WAT2SirT1 koko/Wat2 Control) |
|---|---|---|---|---|---|---|---|
| Ppp1r13b | Protein phosphatase 1, regulatory (inhibitor) subunit 13B | NM_011625.1 | 21981 | 12 | 18.28194153 | 19.40556888 | 1.061461052 |
| Lpl | Lipoprotein lipase | NM_008509.2 | 16956 | 8 | 0.074884575 | 0.05497223 | 0.734092836 |
| H6pd | Hexose-6-phosphate dehydrogenase (glucose 1-dehydrogenase) | NM_173371.3 | 100198 | 4 | 2.017038172 | 1.904920543 | 0.944414721 |
| Pcsk2 | Proprotein convertase subtilisin/kexin type 2 | NM_008792.3 | 18549 | 2 | 7304.568756 | 16775.99623 | 2.296644304 |
| Pfkm | Phosphofructokinase, muscle | NM_021514.3 | 18642 | 15 | 134.4942223 | 152.373776 | 1.132939195 |
| Sos2 | Son of sevenless homolog 2 (Drosophila) | | 20663 | 12 | 7.426041548 | 8.488224547 | 1.143034885 |
| Flot2 | Flotillin 2 | NM_001040403.1 NM_008028.2 | 14252 | 11 | 3.908045833 | 5.507993366 | 409398354 |

FIG. 6H

| Gene Name | Description | Refseq RNA | Entrez Gene | En-sembl Chr | WAT2 Control | WAT2 SirT1 koko | Fold change (WAT2SirT1 koko/Wat2 Control) |
|---|---|---|---|---|---|---|---|
| Srebf1 | Sterol regulatory element binding factor 1 | NM_011480.3 | 20787 | 11 | 1.388063325 | 1.848987949 | 1.33206311 |
| Dgat1 | Diacylglycerol O-acyltransferase 1 | NM_010046.2 | 13350 | 15 | 0.68338069 | 0.573372581 | 0.839023679 |
| Akt1 | Thyoma viral proto-oncogene 1 | NM_009652.2 | 11651 | 12 | 2.556365969 | 2.138122959 | 0.836391575 |
| Myo1c | Myosin IC | NM_001080774.1 NM_001080775.1 NM_008659.3 | 17913 | 11 | 1.828449 | 2.77776552 | 1.519192233 |
| Mchr1 | Melanin-concentrating hormone receptor 1 | NM_145132.1 | 207911 | 15 | 2109.874377 | 1292.761857 | 0.612719824 |
| Cd36 | CD36 antigen | NM_007643.3 | 12491 | 5 | 0.039557591 | 0.061702888 | 1.559824207 |
| Rab4a | RAB4A, member RAS oncogene family | NM_009003.2 | 19341 | 8 | 15.9426924 | 18.15859685 | 1.138991859 |
| Raf1 | V-raf-leukemia viral oncogene 1 | NM_029780.3 | 110157 | 6 | 1.462141957 | 2.587132282 | 1.769412518 |
| Edn1 | Endothelin 1 | NM_010104.2 | 13614 | 13 | 43.49652939 | 39.04237257 | 0.89759742 |

| Gene Name | Description | Refseq RNA | Entrez Gene | En-sembl Chr | WAT2 Control | WAT2 SirT1 koko | Fold change (WAT2SirT1 koko/Wat2 Control) |
|---|---|---|---|---|---|---|---|
| Gys2 | Glycogen synthase 2 | NM_145572.1 | 232493 | 6 | 16.69114924 | 43.50196975 | 2.606289664 |
| Nr1h4 | Nuclear receptor subfamily 1, group H, member 4 | NM_009108.1 | 20186 | 10 | 24.16657952 | 50.55944851 | 2.092122655 |
| Ghr | Growth hormone receptor | NM_001048147.1 NM_001048178.1 NM_010284.2 | 14600 | 15 | 0.180696866 | 0.266491389 | 1.474798069 |
| Ppp1cb | Protein phosphatase 1, catalytic subunit, beta isoform | NM_172707.2 | 19046 | 5 | 0.561105277 | 0.602119114 | 1.073094727 |
| Araf | V-raf murine sarcoma 3611 viral oncogene homolog | NM_009703.1 | 11836 | X | 3.04242856 | 3.097683661 | 1.018161511 |
| Prkca | Protein kinase C, alpha | NM_011101.2 | 18750 | 11 | 19.16255977 | 22.59741469 | 1.17924823 |
| Pde3b | Phosphodiesterase 3B, cGMP-inhibited | NM_011055.2 | 18576 | 7 | 0.761660713 | 0.717785071 | 0.942394768 |
| Plin | Perilipin | NM_175640.1 | 103968 | 7 | 0.564355597 | 0.929675294 | 1.647321829 |
| Tsc2 | Tuberous sclerosis 2 | | 22084 | | 11.14131322 | 12.10680114 | 1.086658359 |

FIG. 6I

| Gene Name | Description | Refseq RNA | Entrez Gene | En-sembl Chr | WAT2 Control | WAT2 SirT1 koko | Fold change (WAT2SirT1 koko/Wat2 Control) |
|---|---|---|---|---|---|---|---|
| Flot1 | Flotillin 1 | NM_008027.2 | 14251 | 17 | 1.725898219 | 1..959297973 | 1.135233788 |
| Wnk1 | WNK lysine deficient protein kinase 1 | NM_198703.1 | 232341 | 6 | 4.21291377 | 4.390979569 | 1.042266661 |
| Ptprn | Protein tyrosine phosphatase, receptor type, N | NM_008985.2 | 19275 | 1 | 330.6207329 | 244.7201052 | 0.740183784 |
| Ptpn1 | Protein tyrosine phosphatase, non-receptor type 1 | NM_011201.3 | 19246 | 2 | 25.67731393 | 31.26231742 | 1.21750731 |
| Mlxipl | MLX interacting protein-like | NM_021455.3 | 58805 | 5 | 3.681978971 | 4.2050671 | 1.142067115 |
| Fto | Fat mass and obesity associated | | 26383 | | 3.133337962 | 3.563055169 | 1.137143587 |
| Inppl1 | Inositol polyphosphate phosphatase-like 1 | NM_010567.1 | 16332 | 7 | 6.230411219 | 7.049523878 | 1.13147008 |
| Pck1 | Phosphoenolpyruvate carboxykinase 1, cytosolic | | 18534 | | 0.87582673 | 0.499125605 | 0.56989081 |

| Gene Name | Description | Refseq RNA | Entrez Gene | En-sembl Chr | WAT2 Control | WAT2 SirT1 koko | Fold change (WAT2SirT1 koko/Wat2 Control) |
|---|---|---|---|---|---|---|---|
| Eif4e2 | Eukaryotic translation initiation factor 4E member 2 | NM_001039169.1 NM_001039170.1 NM_023314.3 | 26987 | 1 | 2.89593734 | 3.978983239 | 1.373988029 |
| Crk | V-crk sarcoma virus CT10 oncogene homolog (avian) | NM_133656.3 | 12928 | 11 | 1.163929267 | 1.192855941 | 1.024852605 |
| Jak2 | Janus kinase 2 | NM_001048177.1 NM_008413.2 | 16452 | 19 | 10.90483766 | 11.52035941 | 1.056444834 |
| Rac1 | RAS-related C3 botulinum substrate 1 | NM_009007.2 | 19353 | 5 | 0.516399456 | 0.560545669 | 1.085488496 |
| Angptl3 | Angiopoietin-like 3 | | 30924 | | 20.13293203 | 24.04933042 | 1..194526976 |
| Ghrh | Growth hormone releasing | NM_010285.2 | 14601 | 2 | 378.7991772 | 1077.693208 | 2.845025208 |
| Foxo1 | Forkhead box O1 | NM_019739.2 | 56458 | 3 | 1.453561776 | 2.11124034 | 1.452460002 |
| Gsk3b | Glycogen synthase kinase 3 beta | NM_019827.6 | 56637 | 16 | 4.776240182 | 5.339215655 | 1.117870009 |
| Hmga1 | High mobility group AT-hook 1 | NM_001025427.2 NM_001039356.1 NM_016660.2 | 15361 | 17 | 35.18214129 | 31.43968421 | 0.893626228 |

FIG. 6J

| Gene Name | Description | Refseq RNA | Entrez Gene | En-sembl Chr | WAT2 Control | WAT2 SirT1 koko | Fold change (WAT2SirT1 koko/Wat2 Control) |
|---|---|---|---|---|---|---|---|
| Sox6 | SRY-box containing gene 6 | NM_001025559.2 NM_001025560.1 NM_011445.3 | 20679 | 7 | 13.96154202 | 20.60493235 | 1.475834999 |
| Prkaa1 | Protein kinase, AMP-activated, alpha 1 catalytic subunit | NM_001013367.3 | 105787 | 15 | 4.686599092 | 5.283331089 | 1.127327298 |
| Socs7 | Suppressor of cytokine signaling 7 | NM_138657.3 | 192157 | 11 | 35.02097603 | 20.96130774 | 0.598535795 |
| Cebpd | CCAAT/enhancer binding protein (C/EBP), delta | | 12609 | | 7.279979496 | 6.001835684 | 0.824430301 |
| Tlr2 | Toll-like receptor 2 | NM_011905.3 | 24088 | 3 | n.a. | n.a. | n.a |
| Mknk2 | MAP kinase-interacting serine/threonine kinase 2 | NM_021462.3 | 17347 | 10 | 0.951528905 | 1.030904593 | 1.083419103 |
| Insig2 | Insulin induced gene 2 | NM_133748.1 NM_178082.2 | 72999 | 1 | 1.625480656 | 2.203032566 | 1.355311463 |
| Snap23 | Synaptosomal-associated protein 23 | NM_009222.3 | 20619 | 2 | 3.956616911 | 4.807279954 | 1.214997575 |

| Gene Name | Description | Refseq RNA | Entrez Gene | En-sembl Chr | WAT2 Control | WAT2 SirT1 koko | Fold change (WAT2SirT1 koko/Wat2 Control) |
|---|---|---|---|---|---|---|---|
| Serpine1 | Serine (or cysteine) peptidase inhibitor, clade E, member 1 | NM_008871.1 | 18787 | 5 | 160.5272475 | 188.2230916 | 1.172530486 |
| Map2k1 | Mitogen activated protein kinase kinase 1 | NM_008927.3 | 26395 | 9 | 11.50175723 | 13.3609883 | 1.161647567 |
| Nfkb1 | Nuclear factor of kappa light chain gene enhancer in B-cells 1, p105 | NM_008689.2 | 18033 | 3 | 3.749206755 | 4.02673581 | 1.074023406 |
| Trf | Transferrin | NM_133977.2 | 22041 | 9 | 0.25028494 | 0.203919383 | 0.814748914 |
| Stx1a | Syntaxin 1A (brain) | NM_016801.3 | 20907 | 5 | 47.25546855 | 48.66999839 | 1.029933675 |
| Prkag1 | Protein kinase, AMP-activated, gamma 1 non-catalytic subunit | NM_016781.2 | 19082 | 15 | 12.107536 | 13.96342377 | 1.153283688 |
| Prkx | Protein kinase, X-linked | NM_016979.1 | 19108 | X | 6.470393204 | 5.646460611 | 0.872661125 |
| Trib3 | Tribbles homolog 3 (Drosophila) | NM_175093.2 | 228775 | 2 | 55.76656047 | 61.30168488 | 1.099255259 |
| Cnr1 | Cannabinoid receptor 1 (brain) | NM_007726.3 | 12801 | 4 | 25.09309269 | 25.03982929 | 0.997877368 |

FIG. 6K

| Gene Name | Description | Refseq RNA | Entrez Gene | En-sembl Chr | WAT2 Control | WAT2 SirT1 koko | Fold change (WAT2SirT1 koko/Wat2 Control) |
|---|---|---|---|---|---|---|---|
| Pygm | Muscle glycogen phosphorylase | NM_011224.1 | 19309 | 19 | 40.08971864 | 80.09669569 | 1.99793609 |
| Pten | Phosphatase and tensin homolog | NM_008960.2 | 19211 | 19 | 0.703011594 | 0.86206456 | 1.226245154 |
| Rps6kb2 | Ribosomal protein S6 kinase, polypeptide 2 | NM_021485.2 | 58988 | 19 | 7.65430499 | 8.605558474 | 1.124276925 |
| Tlr4 | Toll-like receptor 4 | NM_021297.2 | 21898 | 4 | 19.18104461 | 23.00656706 | 1.199442863 |
| Prkar1a | Protein kinase, cAMP dependent regulatory, type I, alpha | NM_021880.2 | 19084 | 11 | 4.442184723 | 5.16064654 | 1.161736142 |
| Vdr | Vitamin D receptor | NM_009504.3 | 22337 | 15 | 579.7075187 | 463.1580639 | 0.79895128 |
| Ptpn2 | Protein tyrosine phosphatase, non-receptor type 2 | | 19255 | | 75.50285991 | 77.75097285 | 1.029775202 |
| Snap25 | Synaptosomal-associated protein 25 | NM_011428.3 | 20614 | 2 | 1184.901474 | 590.5288862 | 0.49837805 |
| Irsl1 | Insulin receptor substrate 1 | NM_010570.3 | 16367 | 1 | 12.95531678 | 11.07659706 | 0.854984656 |

| Gene Name | Description | Refseq RNA | Entrez Gene | En-sembl Chr | WAT2 Control | WAT2 SirT1 koko | Fold change (WAT2SirT1 koko/Wat2 Control) |
|---|---|---|---|---|---|---|---|
| Enpp1 | Ectonucleotide pyrophosphatase/ phosphodiesterase 1 | NM_008813.3 | 18605 | 10 | 80.06342271 | 154.7312537 | 1.93260853 |
| Eif4ebp2 | Eukaryotic translation initiation factor 4E binding protein 2 | NM_010124.2 | 13688 | 10 | 2.905614661 | 3.309983033 | 1.139167928 |
| Ptrf | Protein tyrosin phosphatase, receptor type, F | NM_011213.2 | 19268 | 4 | 33.69961927 | 37.75167684 | 1.120240455 |
| Osbp11a | Oxysterol binding protein-like 1 A | NM_207530.2 | 64291 | 18 | 68.60193606 | 73.94259764 | 1.077850013 |
| Akt1s | AKT1 substrate 1 (proline-rich) | | 67605 | | 4.680210397 | 4.650864221 | 0.993729731 |
| Cd4 | CD4 antigen | NM_013488.2 | 12504 | 6 | 469.8685471 | 192.6899906 | 0.410093401 |
| genomic3 | | | | | 2771.504024 | 4111.034665 | 1.48332264 |
| Kras | V-Ki-ras2 Kirsten rat sarcoma viral oncogene homolog | NM_021284.4 | 16653 | 6 | 3.881772013 | 4.898692799 | 1.261973342 |

FIG. 6L

| Gene Name | Description | Refseq RNA | Entrez Gene | En-sembl Chr | WAT2 Control | WAT2 SirT1 koko | Fold change (WAT2SirT1 koko/Wat2 Control) |
|---|---|---|---|---|---|---|---|
| Ghrl | Ghrelin | NM_021488.4 | 58991 | 6 | 61.05148097 | 45.00211252 | 0.737117459 |
| Aldh3a2 | Aldehyde dehydrogenase family 3, subfamily A2 | | 11671 | | 2.343262189 | 2.980259223 | 1.27184198 |
| Cav1 | Caveolin, caveolae protein 1 | NM_007616.3 | 12389 | 6 | 0.088633776 | 0.103367662 | 1.16623331 |
| Phkb | Phosphorylase kinase beta | NM_199446.1 | 102093 | 8 | 7.117341139 | 9.244343202 | 1.298847845 |
| Sirt4 | Sirtuin 4 (silent mating type information regulation 2 homolog) 4 (S. cerevisiae) | | 75387 | 5 | 57.12614956 | 44.2911583 | 0.775321961 |
| Agrp | Agouti related protein | | 11604 | | 156.1772373 | 147.4958775 | 0.944413412 |
| Sorbs1 | Sorbin and SH3 domain containing 1 | NM_001034962.1 NM_001034963.1 NM_001034964.1 NM_009166.3 NM_178362.1 | 20411 | 19 | 0.622283279 | 0.667974911 | 1.073425775 |

| Gene Name | Description | Refseq RNA | Entrez Gene | En-sembl Chr | WAT2 Control | WAT2 SirT1 koko | Fold change (WAT2SirT1 koko/Wat2 Control) |
|---|---|---|---|---|---|---|---|
| Hadha | Hydroxyacyl-Coenzyme A dehydrogenase/3-ketoacyl-Coenzyme A thiolase/enoyl-Coenzyme A hydratase (trifunctional protein), alpha subunit | NM_178878.2 | 97212 | 5 | 1.182756744 | 1.385785362 | 1.171657121 |
| Vtn | Vitronectin | NM_011707.1 | 22370 | 11 | 7.117873963 | 5.246370962 | 0.737069944 |
| Sos1 | Son of sevenless homolog 1 (Drosophila) | NM_009231.2 | 20662 | 17 | 5.337412031 | 4.896581244 | 0.917407391 |
| Nr3c1 | Nuclear receptor subfamily 3, group C, member 1 | NM_008173.3 | 14815 | 18 | 1.016321172 | 1.024732833 | 1.008276578 |
| Cntf | | | | | 113.3139277 | 109.7829211 | 0.968838724 |
| Prkar2a | Protein kinase, cAMP dependent regulatory, type II alpha | NM_008924.2 | 19087 | 9 | 6.086071939 | 8.288217264 | 1.361833601 |

FIG. 6M

| Gene Name | Description | Refseq RNA | Entrez Gene | En-sembl Chr | WAT2 Control | WAT2 SirT1 koko | Fold change (WAT2SirT1 koko/Wat2 Control) |
|---|---|---|---|---|---|---|---|
| Unc13b | Unc-13 homolog B (C. elegans) | | 22249 | | 89.32916597 | 87.00207001 | 0.973949203 |
| Pparg | Peroxisome proliferator activated receptor gamma | NM_011146.2 | 19016 | 6 | 1.064755651 | 1.788671958 | 1.679889613 |
| Ptpra | Protein tyrosine phosphatase, receptor type, A | NM_008980.1 | 19262 | 2 | 2.536547869 | 2.583061194 | 1.018337255 |
| Foxa2 | Forkhead box A2 | NM_010446.2 | 15376 | 2 | 2361.067198 | 43758.86875 | 18.53351264 |
| Adipor2 | Adiponectin receptor 2 | NM_197985.3 | 68465 | 6 | 0.467466014 | 0.47432829 | 1.014679732 |
| Mkks | McKusick-Kaufman syndrome protein | NM_021527.1 | 59030 | 2 | 16.90085569 | 33.31067819 | 1.970946253 |
| Ptpn9 | Protein tyrosine phosphatase, non-receptor type 9 | NM_019651.2 | 56294 | 9 | 11.48888103 | 14.12264905 | 1.229244955 |
| Gys1 | Glycogen synthase 1, muscle | NM_030678.3 | 14936 | 7 | 3.051262684 | 4.140433492 | 1.356957404 |

| Gene Name | Description | Refseq RNA | Entrez Gene | En-sembl Chr | WAT2 Control | WAT2 SirT1 koko | Fold change (WAT2SirT1 koko/Wat2 Control) |
|---|---|---|---|---|---|---|---|
| Fas | Fas (TNF receptor superfamily member 6) | NM_007987.1 | 14102 | 19 | 2.641624466 | 2.947283462 | 1.115708724 |
| Igf1 | Insulin-like growth factor 1 | NM_010512.3 NM_184052.2 | 16000 | 10 | 0.928869861 | 0.913345634 | 0.983286973 |
| Tub | Tubby candidate gene | NM_021885.4 | 22141 | 7 | 236.5777175 | 250.7969202 | 1.060103728 |
| Mapk1 | Mitogen activated protein kinase 1 | NM_001038663.1 NM_011949.3 | 26413 | 16 | 2.122290854 | 2.7566571 | 1.298906366 |
| Ppyr1 | Pancreatic polypeptide receptor 1 | NM_008919.4 | 19065 | 14 | 1317.244451 | 2475.803023 | 1.879531943 |
| Prkag2 | Protein kinase, AMP-activated, gamma 2 non-catalytic subunit | NM_145401.1 | 108099 | 5 | 3.996661498 | 5.133503689 | 1.284447955 |
| Ppp1ca | Protein phosphatase 1, catalytic subunit, alpha isoform | | 19045 | | 0.498399106 | 0.618472701 | 1.24091856 |
| Abca1 | ATP-binding cassette, sub-family A (ABC1), member 1 | NM_013454.3 | 11303 | 4 | 1.040681346 | 1.263558817 | 1.214164952 |

FIG. 6N

| Gene Name | Description | Refseq RNA | Entrez Gene | En-sembl Chr | WAT2 Control | WAT2 SirT1 koko | Fold change (WAT2SirT1 koko/Wat2 Control) |
|---|---|---|---|---|---|---|---|
| Cacna1c | Calcium channel, voltage- dependent, L type, alpha 1C subunit | NM_009781.2 | 12288 | 6 | 71.56981707 | 161.0345924 | 2.250034987 |
| Frap1 | FK506 binding protein 12- rapamycin associated protein 1 | NM_020009.1 | 56717 | 4 | 10.51385171 | 15.0495748 | 1.431404514 |
| Enpp2 | Ectonucleotide pyrophosphatase/ phosphodiesterase 2 | NM_015744.1 | 18606 | 15 | 0.994944797 | 1.058427772 | 1.063805525 |
| Pkm2 | Pyruvate kinase, muscle | | 18746 | | 0.819853128 | 1.801702514 | 2.197591803 |
| Inpp5d | Inositol polyphosphate-5-phosphatase D | NM_001110192.1 NM_001110193.1 NM_010566.2 | 16331 | 1 | 81.74697198 | 92.07073904 | 1.12628929 |
| Lrp5 | Low density lipoprotein receptor- related protein 5 | NM_008513.2 | 16973 | 19 | 5.596513679 | 4.578061431 | 0.818020234 |
| Adrbk1 | Adrenergic receptor kinase, beta 1 | | 110355 | | 21.64728798 | 21.24322388 | 0.981334193 |

| Gene Name | Description | Refseq RNA | Entrez Gene | En-sembl Chr | WAT2 Control | WAT2 SirT1 koko | Fold change (WAT2SirT1 koko/Wat2 Control) |
|---|---|---|---|---|---|---|---|
| Ppard | Peroxisome proliferator activator receptor delta | | 19015 | | 15.88392322 | 14.01330962 | 0.882232269 |
| Phka2 | Phosphorylase kinase alpha 2 | NM_172783.2 | 110094 | X | n.a. | n.a. | n.a. |
| Mapk8 | Mitogen activated protein kinase 8 | NM_016700.3 | 26419 | 14 | 23.1082065 | 23.50462603 | 1.017154924 |
| Adrb3 | Adrenergic receptor, beta 3 | NM_013462.3 | 11556 | 8 | 0.848191181 | 0.74079888 | 0.87338668 |
| Tnfrsf1b | Tumor necrosis factor receptor superfamily, member 1b | NM_011610.3 | 21938 | 4 | 37.1177251 | 44.14844815 | 1.189416863 |
| Prkcb1 | Protein kinase C, beta 1 | NM_008855.2 | 18751 | 7 | 97.08546306 | 155.5146649 | 1.601832653 |
| Socs3 | Suppressor of cytokine signaling 3 | NM_007707.2 | 12702 | 11 | 32.13009602 | 34.23456609 | 1.065498406 |
| Socs6 | Suppressor of cytokine signaling 6 | NM_018821.3 | 54607 | 18 | 21.0539991 | 32.33464401 | 1.535795829 |
| Wfs1 | Wolfram syndrome 1 homolog (human) | NM_011716.2 | 22393 | 5 | 17.207235 | 20.07539991 | 1.16668366 |

FIG. 6O

| Gene Name | Description | Refseq RNA | Entrez Gene | En-sembl Chr | WAT2 Control | WAT2 SirT1 koko | Fold change (WAT2SirT1 koko/Wat2 Control) |
|---|---|---|---|---|---|---|---|
| Gpam | Glycerol-3-phosphate acyltransferase, mitochondrial | NM_008149.3 | 14732 | 19 | 1.291218708 | 2.104480033 | 1.629840104 |
| Slc2a4 | Solute carrier family 2 (facilitated glucose transporter), member 4 | NM_009204.2 | 20528 | 11 | 0.50494963 | 0.510682604 | 1.011353556 |
| Calca | Calcitonin/calcitonin-related polypeptide, alpha | NM_001033954.2 NM_007587.1 | 12310 | 7 | 120.1685357 | 170.0541993 | 1.415130827 |
| Apln | Apelin | NM_013912.3 | 30878 | X | 33.14348463 | 28.49087099 | 0.859622074 |
| Mapk9 | Mitogen activated protein kinase 9 | NM_016961.2 NM_207692.1 | 26420 | 11 | 5.40880313 | 7.952898849 | 1.470362048 |
| Esr1 | Estrogen receptor 1 (alpha) | NM_007956.4 | 13982 | 10 | 12.48663978 | 11.56796207 | 0.926427147 |
| Calm2 | Calmodulin 2 | NM_009790.4 NM_007590.3 NM_007589.4 | 12314 | 17 | 0.715032334 | 0.806158165 | 1.127442951 |
| Gyg | Glycogenin | NM_013755.2 | 27357 | 3 | 1.877386105 | 2.384428995 | 1.270079175 |

| Gene Name | Description | Refseq RNA | Entrez Gene | En-sembl Chr | WAT2 Control | WAT2 SirT1 koko | Fold change (WAT2SirT1 koko/Wat2 Control) |
|---|---|---|---|---|---|---|---|
| Pdpk1 | 3-phosphoinositide dependent protein kinase-1 | NM_001080773.1 NM_011062.4 | 18607 | 17 | 6.795865911 | 6.118923328 | 0.900389061 |
| Ide | Insulin degrading enzyme | NM_031156.2 | 15925 | 19 | 2.853412626 | 3.792846069 | 1.329231543 |
| Bad | Bcl-associated death promoter | NM_007522.2 | 12015 | 19 | 3.380126845 | 3.842133962 | 1.136683367 |
| Cartpt | CART prepropeptide | NM_001081493.1 NM_013732.6 | 27220 | 13 | 2265.279555 | 960.4327719 | 0.4239798 |
| Osbpl3 | Oxysterol binding protein-like 3 | | 71720 | | 112.7223971 | 86.00954223 | 0.763020876 |
| Pfkl | Phosphofructokinase, liver, B-type | NM_008826.4 | 18641 | 10 | 5.84161544 | 5.425164269 | 0.928709588 |
| Grk4 | G protein-coupled receptor kinase 4 | NM_001080743.1 NM_019497.2 | 14772 | 5 | 167.1394388 | 146.5961924 | 0.877089174 |
| Osbpl5 | Oxysterol binding protein-like 5 | NM_024289.2 | 79196 | 7 | 9.019643342 | 8.59245161 | 0.952637625 |

FIG. 6P

| Gene Name | Description | Refseq RNA | Entrez Gene | En-sembl Chr | WAT2 Control | WAT2 SirT1 koko | Fold change (WAT2SirT1 koko/Wat2 Control) |
|---|---|---|---|---|---|---|---|
| Tgfb1 | Transforming growth factor, beta 1 | NM_011577.1 | 21803 | 7 | 9.765476134 | 8.585896739 | 0.879209229 |
| Nos2 | Nitric oxide synthase 2, inducible, macrophage | NM_010927.3 | 18126 | 11 | 42.12087166 | 30.19918733 | 0.716964919 |
| Sirt1 | Sirtuin 1 ((silent mating type information regulation 2, homolog) 1 (S. cerevisiae) | NM_019812.1 | 93759 | 10 | 12.98508351 | 13.78732646 | 1.061781886 |
| Map2k2 | Mitogen activated protein kinase kinase 2 | NM_023138.4 | 26396 | 10 | 6.431438189 | 7.973802221 | 1.23981635 |
| Mapk3 | Mitogen activated protein kinase 3 | NM_011952.2 | 26417 | 7 | 1.821172257 | 2.074030086 | 1.138843444 |
| Lipe | Lipase, hormone sensitive | NM_001039507.1 NM_010719.5 | 16890 | 7 | 0.176143896 | 0.241422296 | 1.370597003 |
| Rps6kb1 | Ribosomal protein S6 kinase, polypeptide 1 | NM_028259.3 | 72508 | 11 | 85.30103769 | 73.69719588 | 0.863965995 |
| Socs1 | Suppressor of cytokine signaling 1 | NM_009896.2 | 12703 | 16 | 89.88331241 | 37.7040298 | 0.419477529 |

| Gene Name | Description | Refseq RNA | Entrez Gene | En-sembl Chr | WAT2 Control | WAT2 SirT1 koko | Fold change (WAT2SirT1 koko/Wat2 Control) |
|---|---|---|---|---|---|---|---|
| Lpin1 | Lipin 1 | NM_015763.3 NM_172950.2 | 14245 | 12 | 0.693372915 | 0.897206403 | 1.293973825 |
| Ptges2 | Prostaglandin E synthase 2 | NM_133783.1 | 96979 | 2 | 6.916227796 | 9.644756544 | 1.394511116 |
| Itgav | Integrin alpha V | NM_008402.2 | 16410 | 2 | 12.93999708 | 22.79530523 | 1.761615949 |
| Igf2 | Insulin-like growth factor 2 | NM_010514.2 | 16002 | 7 | 19.21240721 | 23.18930733 | 1.206996452 |
| Eif4ebp1 | Eukaryotic translation initiation factor 4E binding protein 1 | NM_007918.3 | 13685 | 8 | 0.440674826 | 0.533417411 | 1..210455827 |
| Prkch | Protein kinase C, eta | | 18755 | | 9.687428934 | 0.925196886 | 10.47064483 |
| Cebpa | CCAAT/enhancer binding protein (C/EBP), alpha | NM_007678.3 | 12606 | 7 | 0.245567133 | 0.319819059 | 1.302369153 |
| Shc2 | Src homology 2 domain-containing transforming protein C2 | | 216148 | | 489.2399439 | 313.0828824 | 0.639937287 |

FIG. 6Q

| Gene Name | Description | Refseq RNA | Entrez Gene | En-sembl Chr | WAT2 Control | WAT2 SirT1 koko | Fold change (WAT2SirT1 koko/Wat2 Control) |
|---|---|---|---|---|---|---|---|
| Cdc42 | Cell division cycle 42 homolog (S. cerevisiae) | NM_009861.1 | 12540 | 4 | 0.460438823 | 0.4912546 | 1.066926974 |
| Shc4 | | | | | 167.6350931 | 152.7623091 | 0.911278816 |
| Glp1r | Glucagon-like peptide 1 receptor | NM_021332.2 | 14652 | 17 | 5233.888181 | 2961.743161 | 0.565878188 |
| Neu3 | Neuraminidase 3 | NM_016720.2 | 50877 | 7 | 157.8894962 | 174.2415426 | 1.103566398 |
| Gne | Glucosamine | NM_015828.2 | 50798 | 4 | 22.65760377 | 31.08439989 | 1.371919123 |
| Dusp9 | Dual specificity phosphatase 9 | NM_029352.3 | 75590 | X | 55.67579649 | 97.32488446 | 1.74806452 |
| Prkab1 | Protein kinase, AMP-activated, beta 1 non-catalytic subunit | NM_031869.2 | 19079 | 5 | 22.29724233 | 21.10640292 | 0.946592525 |
| Pik3r2 | Phosphatidylinositol 3-kinase, regulatory subunit, polypeptide 2 (p85 beta) | NM_008841.1 | 18709 | 8 | 10.57095188 | 7.166729098 | 0.677964405 |

| Gene Name | Description | Refseq RNA | Entrez Gene | En-sembl Chr | WAT2 Control | WAT2 SirT1 koko | Fold change (WAT2SirT1 koko/Wat2 Control) |
|---|---|---|---|---|---|---|---|
| Adipoq | Adiponectin, C1Q and collagen domain containing | NM_009605.4 | 11450 | 16 | 0.022972639 | 0.021364225 | 0.929985667 |
| Adrb2 | Adrenergic receptor, beta 2 | NM_007420.2 | 11555 | 18 | 28.65923881 | 41.60799377 | 1.451817826 |
| Ppargc1a | Peroxisome proliferative activated receptor, gamma, coactivator 1 alpha | NM_008904.1 | 19017 | 5 | 32.83281145 | 31.90381009 | 0.971705093 |
| Bbs1 | Bardet-Biedl syndrome 1 homolog (human) | NM_001033128.2 | 52028 | 19 | 354.5131635 | 190.1067334 | 0.536247319 |
| Thbd | Thrombomodulin | NM_009378.2 | 21824 | 2 | 2.082651414 | 3.199864516 | 1.536437876 |
| Adcyap1 | Adenylate cyclase activating polypeptide 1 | NM_009625.2 | 11516 | 17 | 5323.441061 | 2623.797786 | 0.492876272 |
| Pde3a | Phosphodiesterase 3A, cGMP inhibited | NM_018779.1 | 54611 | 6 | 48.80808987 | 54.20176107 | 1.11050773 |
| Klf11 | Kruppel-like factor 11 | NM_178357.2 | 194655 | 12 | 22.07984879 | 19.87249103 | 0.900028402 |

FIG. 6R

| Gene Name | Description | Refseq RNA | Entrez Gene | En-sembl Chr | WAT2 Control | WAT2 SirT1 koko | Fold change (WAT2SirT1 koko/Wat2 Control) |
|---|---|---|---|---|---|---|---|
| Nras | Neuroblastoma ras oncogene | NM_010937.2 | 18176 | 3 | 431.2735377 | 382.0415714 | 0.885845149 |
| Src | Rous sarcoma oncogene | NM_001025395.2 NM_009271.3 | 20779 | 2 | 53.29408027 | 52.32606343 | 0.981836316 |
| Retn | Resistin | NM_022984.3 | 57264 | 8 | 3.284476372 | 4.140089115 | 1.260502024 |
| Pik3cb | Phosphatidylinositol 3-kinase catalytic, beta polypeptide | NM_029094.2 | 74769 | 9 | 4.874199789 | 5.639576474 | 1.157026121 |
| Mif | Macrophage migration inhibitory factor | | 17319 | | 17.51962982 | 14.4560733 | 1.825135773 |
| Fabp2 | Fatty acid binding protein 2, intestinal | NM_007980.2 | 14079 | 3 | 2383.50244 | 12101.1524 | 5.077046365 |
| Aldh1a1 | Aldehyde dehydrogenase family 1, subfamily A1 | NM_013467.3 | 11668 | 19 | 0.640594087 | 0.960190669 | 1.498906544 |
| Rheb | RAS-homolog enriched in brain | NM_053075.3 | 19744 | 5 | 0.552891534 | 0.694403836 | 1.255949482 |
| Apob | Apolipoprotein B | NM_009693.1 | 238055 | 12 | 272.3283536 | 85.93350423 | 0.315551073 |

| Gene Name | Description | Refseq RNA | Entrez Gene | En-sembl Chr | WAT2 Control | WAT2 SirT1 koko | Fold change (WAT2SirT1 koko/Wat2 Control) |
|---|---|---|---|---|---|---|---|
| Rps6 | Ribosomal protein S6 | NM_009096.3 | 20104 | 4 | 6.24023079 | 5.529453202 | 0.886097548 |
| Ceacam1 | CEA-related cell adhesion molecule 1 | NM_001039185.1 NM_001039186.1 NM_011926.2 | 26365 | 7 | 6.763928395 | 10.71238508 | 1.583751994 |
| Prkar1b | Protein kinase, cAMP dependent regulatory, type I beta | NM_008923.2 | 19085 | 5 | 93.01982929 | 66.81160547 | 0.718251216 |
| Alms1 | Alstrom syndrome 1 homolog (human) | NM_145223.2 | 236266 | 6 | 35.99823798 | 26.20762696 | 0.728025271 |
| Lpin2 | Lipin 2 | NM_022882.3 | 64898 | 17 | 47.44678365 | 42.51502325 | 0.896057013 |
| Pik3r3 | Phosphatidylinositol 3 kinase, regulatory subunit, polypeptide 3 (p55) | NM_181585.5 | 18710 | 4 | 23.85659743 | 16.43789687 | 0.689029394 |
| Shc3 | Src homology 2 domain-containing transforming protein C3 | NM_009167.2 | 20418 | 13 | 391.5108249 | 1637.46553 | 4.182427217 |
| Exoc7 | Exocyst complex component 7 | NM_016857.1 | 53413 | 11 | 11.81032194 | 10.71500651 | 0.907257784 |

FIG. 6S

| Gene Name | Description | Refseq RNA | Entrez Gene | En-sembl Chr | WAT2 Control | WAT2 SirT1 koko | Fold change (WAT2SirT1 koko/Wat2 Control) |
|---|---|---|---|---|---|---|---|
| Ins2 | Insulin II | NM_008387.3 | 16334 | 7 | 836.1334367 | 521.0640176 | 0.623182849 |
| Eif4e | Eukaryotic translation initiation factor 4E | NM_007917.3 | 13684 | 3 | 138.2883092 | 128.7488577 | 0.931017658 |
| Cd38 | CD38 antigen | NM_007646.3 | 12494 | 5 | 2.805767349 | 2.704139956 | 0.963779109 |
| Il1b | Interleukin 1 beta | NM_008361.3 | 16176 | 2 | 894.4043453 | 289.5594602 | 0.323745587 |
| Rn18s | | | | | 6.60E-05 | 5.02E-05 | 0.761161705 |
| Cb1 | Casitas B-lineage lymphoma | NM_007619.2 | 12402 | 9 | 114.2344028 | 141.0989872 | 1.235170699 |
| Pdx1 | Pancreatic and duodenal homeobox 1 | NM_008814.3 | 18609 | 5 | 29811.95542 | 17850.23964 | 0.598761114 |
| Pklr | Pyruvate kinase liver and red blood cell | NM_001099779.1 NM_013631.2 | 18770 | 3 | 22.13461519 | 28.12045089 | 1.270428722 |
| Adm | Adrenomedullin | NM_009627.1 | 11535 | 7 | 25.08311098 | 18.42538452 | 0.734573336 |
| Prl | Prolactin | | 19109 | | 1155.861952 | 404.3289858 | 0.349807332 |
| Ptk2b | PTK2 protein tyrosine kinase 2 beta | NM_172498.2 | 19229 | 14 | 84.58924775 | 71.5630426 | 0.846006372 |
| Ccl2 | Chemokine (C-C motif) ligand 2 | NM_011333.3 | 20296 | 11 | 19.22824768 | 39.98920851 | 2.07971136 |

| Gene Name | Description | Refseq RNA | Entrez Gene | En-sembl Chr | WAT2 Control | WAT2 SirT1 koko | Fold change (WAT2SirT1 koko/Wat2 Control) |
|---|---|---|---|---|---|---|---|
| Il10 | Interleukin 10 | NM_010548.1 | 16153 | 1 | 385.0770644 | 227.087553 | 0.589719757 |
| Il18 | Interleukin 18 | NM_008360.1 | 16173 | 9 | 4.561057592 | 7.279921137 | 1.596103752 |
| Cckbr | Cholecystokinin B receptor | NM_007627.4 | 12426 | 7 | 228.2722039 | 564.0916697 | 2.471136039 |
| Acaca | Acetyl-Coenzyme A carboxylase alpha | NM_133360.2 | 107476 | 11 | 0.935567977 | 1.723556774 | 1.842257128 |
| Sct | Secretin | NM_011328.2 | 20287 | 7 | 1285.891665 | 1451.235384 | 1.128582931 |
| Rhoq | Ras homolog gene family, member Q | NM_145491.2 | 104215 | 17 | 1.364245597 | 1.741634416 | 1.276628211 |
| Nkx6-1 | NK6 transcription factor related, locus 1 (Drosophila) | NM_144955.2 | 18096 | 5 | 6218.941742 | 861.0247045 | 0.138451965 |
| Pygb | Brain glycogen phosphorylase | NM_153781.1 | 110078 | 2 | 2.120777673 | 2.691623872 | 1.269168337 |
| Prkcq | Protein kinase C, theta | NM_008859.2 | 18761 | 2 | 97.01509851 | 65.03380011 | 0.670347205 |
| Calml3 | Calmodulin-like 3 | NM_027416.2 | 70405 | 13 | 96.48397144 | 182.0405225 | 1.886743671 |
| Gh | Growth hormone | | 14599 | | 2011.4782 | 30818.96564 | 15.32155091 |

FIG. 6T

| Gene Name | Description | Refseq RNA | Entrez Gene | En-sembl Chr | WAT2 Control | WAT2 SirT1 koko | Fold change (WAT2SirT1 koko/Wat2 Control) |
|---|---|---|---|---|---|---|---|
| Gc | Group specific component | NM_008096.1 | 14473 | 5 | 1466.596603 | 2418.334043 | 1.648942891 |
| Cd44 | CD44 antigen | NM_001039150.1 NM_001039151.1 NM_009851.2 | 12505 | 2 | 132.0023119 | 80.50334483 | 0.609863143 |
| Prox1 | Prospero-related homeobox 1 | NM_008937.2 | 19130 | 1 | 127.0813391 | 206.4269927 | 1.624369039 |
| Retnlb | Resistin like beta | | 57263 | | 12.94979529 | 10.47098184 | 0.808582808 |
| Il1a | Interleukin 1 alpha | NM_010554.4 | 16175 | 2 | 141.719983 | 86.55155424 | 0.610722302 |
| Irs2 | Insulin receptor substrate 2 | NM_001081212.1 | 384783 | 8 | 38.42137878 | 35.89748389 | 0.934310143 |
| Ins1 | Insulin 1 | NM_008386.3 | 16333 | 19 | 610.7594146 | 442.0117227 | 0.723708407 |
| Fabp5 | Fatty acid binding protein 5, epidermal | NM_010634.2 | 16592 | 3 | 8.312298061 | 8.445195506 | 1.015988051 |
| Gip | Gastric inhibitory polypeptide | | 14607 | | 8708.951886 | 3975.315977 | 0.456463192 |
| Unc13a | Unc-13 homolog A (C. elegans) | NM_01029873.1 | 382018 | 8 | 330.6528181 | 516.8320838 | 1.563065716 |

| Gene Name | Description | Refseq RNA | Entrez Gene | En-sembl Chr | WAT2 Control | WAT2 SirT1 koko | Fold change (WAT2SirT1 koko/Wat2 Control) |
|---|---|---|---|---|---|---|---|
| Gipr | Gastric inhibitory polypeptide receptor | | 381853 | | 175.5092657 | 177.1584932 | 1.009396812 |
| Mthfr | 5,10-methylene-tetrahydrofolate reductase | NM_010840.2 | 17769 | 4 | 48.69039796 | 27.2639147 | 0.55994438 |
| Mapk10 | Mitogen activated protein kinase 10 | NM_001081567.1 NM_009158.2 | 26414 | 5 | 5676.832217 | 1002.33762 | 0.176566363 |
| Elovl6 | ELOVL family member 6, elongation of long chain fatty acids (yeast) | NM_130450.2 | 170439 | 3 | 18.96566939 | 31.79695749 | 1.6765534 |
| Pde1c | Phosphodiesterase 1C | NM_001025568.1 NM_011054.3 | 18575 | 6 | 298.3587727 | 328.3288746 | 1.100449877 |
| Npy1r | Neuropeptide Y receptor Y1 | NM_010934.3 | 18166 | 8 | 255.0404707 | 303.8203767 | 1.191263394 |
| Nr0b2 | Nuclear receptor subfamily 0, group B, member 2 | NM_011850.2 | 23957 | 4 | 9271.900616 | 10251.54563 | 1.105657411 |

FIG. 6U

| Gene Name | Description | Refseq RNA | Entrez Gene | En-sembl Chr | WAT2 Control | WAT2 SirT1 koko | Fold change (WAT2SirT1 koko/Wat2 Control) |
|---|---|---|---|---|---|---|---|
| Npy | Neuropeptide Y | NM_023456.2 | 109648 | 6 | 339.1654462 | 154.8043093 | 0.456427124 |
| Gast | Gastrin | NM_010257.3 | 14459 | 11 | 2577.601256 | 964.2248638 | 0.374078365 |
| Tcf1 | | | | | 5295.753982 | 1499.681917 | 0.283185722 |
| Sst | Somatostatin | | 20604 | | 3245.399548 | 1172.352594 | 0.361235212 |
| Il6 | Interleukin 6 | | 16193 | | 984.4665568 | 585.6085559 | 0.594848603 |
| Rem2 | Rad and gem related GTP binding protein 2 | NM_080726.3 | 140743 | 14 | 1895.864823 | 4649.844715 | 2.452624606 |
| Cck | Cholecystokinin | | 12424 | | 4787.289666 | 1031.641373 | 0.215495916 |
| Cblc | Casitas B-lineage lymphoma c | NM_023224.5 | 80794 | 7 | 2345.403433 | 226.60232 | 0.096615498 |
| G6pc | Glucose-6-phophatase, catalytic | NM_008061.3 | 14377 | 11 | 395.3263713 | 194.2571408 | 0.49138422 |
| Ucp1 | Uncoupling protein 1 (mitochondrial, proton carrier) | | 22227 | | 3041.660435 | 1803.5814 | 0.592959483 |
| Gal | Galanin | NM_010253.3 | 14419 | 19 | 3498.731861 | 352.4348602 | 0.100732172 |
| Sele | Selectin, endothelial cell | NM_011345.2 | 20339 | 1 | 2088.990747 | 382.8397501 | 0.183265412 |

| Gene Name | Description | Refseq RNA | Entrez Gene | En-sembl Chr | WAT2 Control | WAT2 SirT1 koko | Fold change (WAT2SirT1 koko/Wat2 Control) |
|---|---|---|---|---|---|---|---|
| Ppp1r3a | Protein phosphatase 1, regulatory (inhibitor) subunit 3A | NM_080464.2 | 140491 | 6 | 2723.287132 | 1324.182103 | 0.486244027 |
| Gcg | Glucagon | | 14526 | | 15908.12725 | 2400.286367 | 0.150884283 |
| Crh | Corticotropin releasing hormone | NM_205769.1 | 12918 | 3 | 28757.15606 | 518.0246078 | 0.018013763 |
| Foxa1 | Forkhead box A1 | NM_008259.3 | 15375 | 12 | 142238.1941 | 203226.7551 | 1.428777667 |
| Trh | Thyrotropin releasing hormone | NM_009426.2 | 22044 | 6 | 20465.67155 | 7853.248436 | 0.383727864 |
| Nmur2 | Neuromedin U receptor 2 | NM_153079.4 | 216749 | 11 | 52367.61886 | 110317.8578 | 2.106604428 |
| Mc4r | Melanocortin 4 receptor | NM_016977.3 | 17202 | 18 | 5030.375522 | 129512.4102 | 25.74607196 |
| Ucn | Urocortin | NM_021290.1 | 22226 | 5 | 131462.3712 | 15236.33002 | 0.115898792 |
| Serpina6 | Serine (or cysteine) peptidase inhibitor, clade A, member 6 | NM_007618.2 | 12401 | 12 | 50754.08724 | 1778.425497 | 0.035040045 |

FIG. 6V

| Gene Name | Description | Refseq RNA | Entrez Gene | En-sembl Chr | WAT2 Control | WAT2 SirT1 koko | Fold change (WAT2SirT1 koko/Wat2 Control) |
|---|---|---|---|---|---|---|---|
| Neurod1 | Neurogenic differentiation 1 | NM 010894.2 | 18012 | 2 | 4183.235164 | 4384.330443 | 1.048071713 |
| Cyp19a1 | Cytochrome P450, family 19, subfamily a, polypeptide 1 | NM_007810.3 | 13075 | 9 | 107278.7931 | 11872.8266 | 0.110672634 |
| Irs4 | Insulin receptor substrate 4 | NM_010572.2 | 16370 | X | 215066.5138 | 1530.506887 | 0.007116435 |
| Cel | Carboxyl ester lipase | NM_009885.1 | 12613 | 2 | 4087.376393 | 2651.404044 | 0.648681156 |
| Trpm2 | Transient receptor potential cation channel, subfamily M, member 2 | NM_138301.1 | 28240 | 10 | 95419.69054 | 1276.352246 | 0.013376194 |
| Nat1 | N-acetyltransferase 1 (arylamine N-acetyltransferase) | NM_008673.1 | 17960 | 8 | 215066.5138 | 609.6311545 | 0.002834617 |
| Nmu | Neuromedin U | NM_019515.1 | 56183 | 5 | 2863.995255 | 203226.7551 | 70.9591801 |

| Up-regulated gene | Fold change |
|---|---|
| Adipocyte | |
| Ldlr | 3.5 |
| Fasn | 2.5 |
| Lep | 2.4 |
| Bnpp1 | 1.9 |
| Brain | |
| Nmu | 71.0 |
| Gad2 | 26.7 |
| Mc4r | 25.7 |
| Gh | 15.3 |
| Htr2c | 7.1 |
| Bdnf | 4.2 |
| Shc3 | 4.2 |
| Glrh | 2.6 |
| Nmur2 | 2.1 |
| Multiple tissues | |
| Hnf4a | 118.7 |
| Igfbp-1 | 83.1 |
| FoxA2 | 18.5 |
| Cacna1e | 8.1 |
| Fabp2 | 5.1 |
| Fbp2 | 4.4 |
| Gys2 | 2.6 |
| Igfbp-3 | 2.5 |
| Rrad | 2.3 |
| Gnb3 | 2.2 |
| Gck | 2.2 |

FIG. 7 a
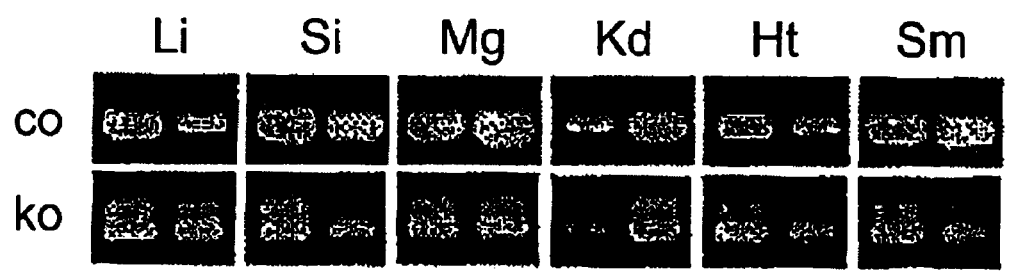
b
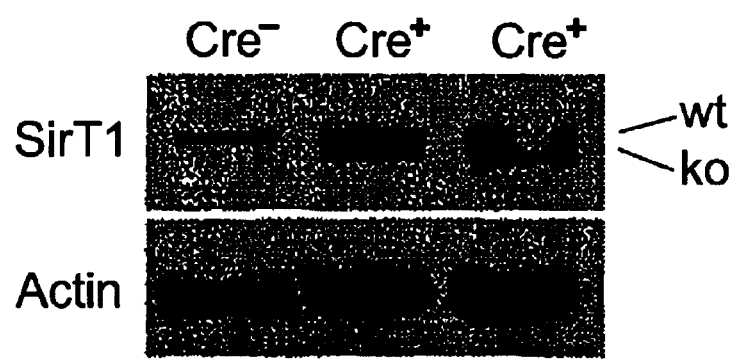
FIG. 10

METHODS FOR TREATING OBESITY

CROSS-REFERENCES TO RELATED APPLICATIONS

The present application is a continuation of U.S. patent application Ser. No. 13/123,703, filed Jul. 1, 2011, which claims the benefit of U.S. Provisional Application No. 61/104,526, filed Oct. 10, 2008, expressly incorporated herein by reference in its entirety.

STATEMENT OF GOVERNMENT LICENSE RIGHTS

Not applicable.

FIELD OF THE DISCLOSURE

The present disclosure provides methods for treating or preventing obesity by reducing the activity of SirT1 protein in a subject. Methods to identify inhibitors of weight gain are also disclosed.

BACKGROUND

Obesity is a growing health problem in many countries. Obesity increases the risk of health problems such as insulin resistance, type 2 diabetes, heart diseases, osteoarthritis, sleep apnea, and some forms of cancer. Reducing excessive body weight can significantly reduce the risk of these health problems. The primary treatment for obesity is dieting and physical exercise followed by weight-loss medication and surgery. Currently, there are only two FDA-approved weight-loss drugs on market: Orlistat (Alli®) and Sibutramine (Meridia®). Neither has achieved the weight-loss goals set by FDA. In addition, several weight-loss drug candidates, also known as appetite suppressants, have been either suspended or canceled at various stages of development due to their severe side effects.

Although there are many methods to reduce initial body weight, long-term maintenance of that lost weight is difficult. Many people who successfully achieve initial weight lost regain the weight subsequently. In addition, morbidly obese patients may need medications for a long-term maintenance of healthy body weight after a successful weight-loss surgery. Therefore, in 2004, NIH recognized that weight loss maintenance is critical in preventing the complications of overweight and obesity (see, Strategic Plan for NTH Obesity Research, 2004). However, there is currently no weight-loss maintenance drug on the market.

There exists a need for methods for inhibiting or reducing weight gain and methods for maintaining weight loss. The present disclosure seeks to fulfill these needs and provides further related advantages.

BRIEF SUMMARY

In one aspect, the present disclosure provides methods for treating or preventing obesity in a subject by reducing the activity of a sirtuin 1 (SirT1) deacetylase protein in the subject. In one embodiment, the step of reducing the activity of a SirT1 deacetylase protein comprises deleting at least partially the gene encoding the SirT1 deacetylase protein. The deletion may be an in-frame deletion affecting the highly conserved Sir2 deacetylase domain.

In another embodiment, the SirT1 deacetylase protein comprises a Sir2 deacetylase domain, and the step of reducing the activity of the SirT1 deacetylase protein comprises introducing at least one mutation into the sequence encoding the Sir2 deacetylase domain, such that the activity of the SirT1 deacetylate protein is reduced. In another embodiment, the step of reducing the activity of the SirT1 deacetylace protein comprises reducing the expression of the gene encoding the SirT1 deacetylase protein. The expression of the gene may be reduced by RNA interference using a SirT1 specific siRNA or miRNA. In a further embodiment, the step of reducing the activity of the SirT1 deacetylase protein comprises contacting an inhibitor with the protein, such that the activity of the protein is reduced. The inhibitor may be any type of sirtuin inhibitors.

In another aspect, the present disclosure provides a method for treating or preventing obesity in a subject by administering an inhibitor of a sirtuin 1 (SirT1) deacetylase protein to the subject. The SirT1 protein inhibitor can inhibit activity or expression of the SirT1 protein and can be, e.g., a siRNA molecule, a miRNA, a small molecule, an antisense molecule, or an antibody. In one embodiment, the inhibitor is a sirtuin inhibitor. In one embodiment, the inhibitor may be a siRNA or a miRNA that inhibits SirT1 expression. SiRNA molecules that inhibit SirT1 expression are known and can be used in the methods of the disclosure. In one embodiment, the SirT1 inhibitor is targeted to adipocytes and inhibits the growth of adipose tissue in the subject. In one embodiment, the subject ingests a high fat diet while taking the SirT1 inhibitor.

In another embodiment, the subject is a human. In a further embodiment, the subject is an adult human. In another embodiment, the subject is a companion animal or a zoo animal. Two or more SirT1 inhibitors may be administered to a subject simultaneously to prevent or reduce weight gain. In another embodiment, one or more SirT1 inhibitors may be administered to a subject together with one or more active compounds known to prevent/reduce weight gain or cause weight loss, including but not limited to, an appetite suppressant, an inhibitor of pancreatic lipases, a 5'AMP-activated protein kinase (AMPK) agonist, a modulator of peroxisome proliferators-activated receptors (e.g. a PPARgamma agonist), a dipeptidyl peptidase-4 (DPP-4) inhibitor, a glucagons-like peptide-1 (GLP-1) analog, an anti-ghrelin vaccine, and a cannabinoid receptor (CBI) antagonist/inverse agonist.

In another aspect, the present disclosure provides a method of identifying an inhibitor of weight gain in a subject by 1) assaying an in vitro activity of a sirtuin 1 (SirT1) deacetylase protein in the presence and absence of a test compound, where a reduction in activity in the presence of the test compound indicates that the test compound inhibits SirT1 deacetylase activity; and 2) administering the test compound to a test subject and measuring the weight of the test subject, wherein the test subject gains less weight compared to a control subject that does not receive the test compound, thus identifying an inhibitor of weight gain in a subject. The test compound can be e.g., an antibody, an antisense molecule, a siRNA molecule, or a small molecule. In one embodiment, the test compound is a sirtuin inhibitor. In another embodiment, the test compound is a siRNA or a miRNA that inhibits SirT1 expression. SiRNA molecules that inhibit SirT1 expression are known and can be used in the methods of the disclosure.

The weights of the test subject and control subject are measured over a period of time.

In one embodiment, the weight of the control subject is 5-50% more than the weight of the test subject at the end of the time period. In further embodiments, the weight of the control subject is 5%, 10%, 15%, 20%, 25%, 30%, 35%, 40%, 45%, or 50% more than the weight of the test subject at the end of the time period. In another embodiment, the weight gain of the control subject is 5-50% more than the weight gain of the test subject at the end of the time period. In another embodiment, the test subject and the control subject ingest a high fat diet while the SirT1 inhibitor is administered to them.

BRIEF DESCRIPTION OF THE DRAWINGS

FIG. 1A shows the WAT percentages of total body weight for inguinal (Ing) fat, epididymal (Epi) fat, and liver in AKOSIRT1 mice at 2 months of age (n 5, p<0.0001, p=0.0073 and 0.92, respectively); and FIG. 1B shows the weights of inguinal (Ing) fat, epididymal (Epi) fat, and liver in AKOSIRT1 mice at 16 months of age (n=5, p=0.19, 0.17, and 0.07, respectively). Asterisks, p<0.01 (two-tailed t-test). Error bars represent s.d.

FIG. 2 provides detailed information of 311 differentially expressed genes in WAT of young adult AKOSIRT1 mice.

FIG. 3 provides detailed information of 64 differentially expressed genes in WAT of mature adult AKOSIRT1 mice.

FIG. 4 provides detailed information of 77 differentially expressed genes in liver of adult SirT1$^{ko/ko}$ mice.

FIG. 5 provides IPA analyses of differentially expressed genes in WAT of AKOSIRT1 mice and liver of SirT1$^{ko/ko}$ mice.

FIG. 6 shows the quantitative real-time PCR analyses of a panel of 384 Diabesity genes in WAT of young adult AKOSIRT1 mice using the same RNA samples used for the microarray analysis.

FIG. 7 provides identification of differentially expressed genes in WAT using quantitative real-time PCR on a panel of 384 diabesity genes. The genes, whose expression as up-regulated in WAT2 of AKOSKIRT1 mice, are divided into three groups based on their normal expression patterns, i.e., 4 adipocyte genes, 8 brain-specific genes, and 12 others, e.g., liver specific genes.

FIG. 10 shows that injection of pI-pC at a pre-puberty age induces SirT1 exon4 deletion in Mx1-Cre$^+$, SirT1$^{co/co}$ mice. 10A shows DNA analysis of Mx-1Cre-mediated SirT1 exon 4 deletion in two Mx1-Cre$^+$, SirT1$^{co/co}$ mice in the following tissues: liver (Li); small intestine (Si); mammary gland (Mg); kidney (Kd); and skeletal muscle (Sm); and 10B shows that Western blot analysis detects the presence of SirT1 mutant protein in the liver of two adult Mx1-Cre$^+$, SirT1$^{co/co}$ mice.

DEFINITIONS

Figure 1:
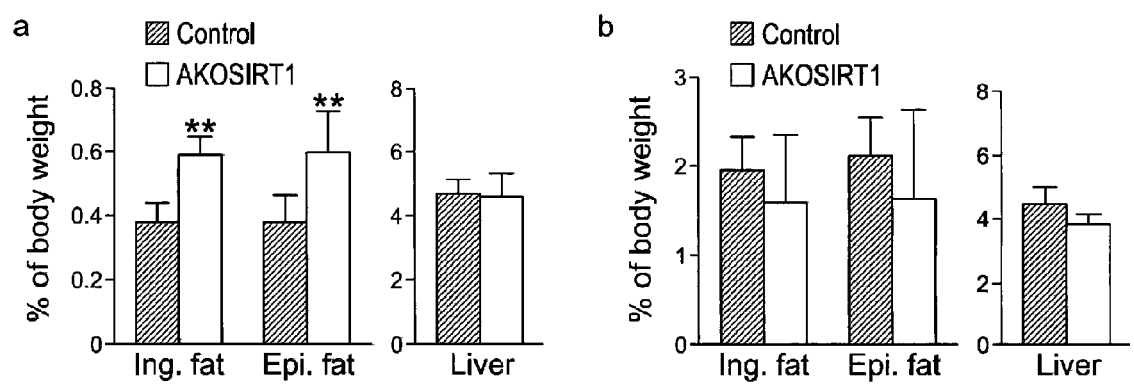
FIG. 1 shows that adipocyte SirT1 negatively modulates the postnatal growth of white adipose tissue (WAT).

The term "treating or preventing obesity," "treatment or prevention of obesity," or grammatical variants refers to weight control management including preventing weight gain, reducing weight gain, and reducing weight.

The term "sirtuin 1 (SirT1) deacetylase protein" or "SirT1" or grammatical variants, refers to a SirT1 protein and polypeptide polymorphic variants, alleles, mutants, and interspecies homologs that: (1) have an amino acid sequence that has at least 60% amino acid sequence identity, 65%, 70%, 75%, 80%, 85%, 90%, preferably 91%, 92%, 93%, 94%, 95%, 96%, 97%, 98% or 99% or greater amino acid sequence identity, preferably over a region of over a region of at least about 25, 50, 100, 200, 500, 1000, or more amino acids, to an amino acid sequence encoded by a SirT1 nucleic acid or to an amino acid sequence of a SirT1 protein (for exemplary SirT1 protein sequences, see, e.g., SEQ ID NO:1 or accession number CAI16036) and (2) bind to antibodies, e.g., polyclonal antibodies, raised against an immunogen comprising an amino acid sequence of a SirT1 protein, and conservatively modified variants thereof. The nucleic acids and proteins of the disclosure include both naturally occurring and recombinant molecules. A SirT1 protein typically has deacetylase activity in vitro, e.g., histone deacetylase activity. Histone deacetylase assays can be performed according to methods known to those of skill in the art, using substrates, as described herein and elsewhere. See, e.g., Vaquero et al., *Molec. Cell* 16:93-105 (2004), which is herein incorporated by reference in its entirety. Other proteins that are potential substrates for deacetylation by SirT1 protein are p53, FOXO3A, and the DNA repair factor ku70. See, e.g., Vaziri et al., Cell 107:149-159 (2001); Motta et al., Cell 116:551-563 (2004); and Cohen et al., Science 305:390-392 (2004); each of which is herein incorporated by reference for all purposes. In a preferred embodiment, sequence identity is measured over the full length of a reference SirT1 sequence, e.g., SEQ ID NO: 1.

"Subject" refers to an individual in need of treatment for a particular disease or condition. In a preferred embodiment, the subject is a human in need of treatment for obesity or is in need of treatment to prevent weight gain.

"High fat diet" refers to a diet that includes greater amounts of fat than typical for a subject. The components of a high fat diet will vary, depending on the species. For example, laboratory mice are typically fed a diet that includes 5% calories from fat, i.e., a normal fat diet. Diets that include higher fat amounts, e.g., 8%, 9%, 10%, 15%, 25%, or 50% fat calories are high fat diets for laboratory mice. For adult humans, the recommended fat intake is 20% to 35% of total calories. Fat intakes that exceed 35% of calories are considered high fat diets for adult humans. See, e.g., United States Department of Agriculture, Dietary Guidelines for Americans, 2005.

The phrase "double-stranded ribonucleic acid molecule" or "dsRNA" as used herein refers to any RNA molecule, fragment or segment containing two strands forming an RNA duplex, notwithstanding the presence of single stranded overhangs of unpaired nucleotides.

Further, as used herein, a double-stranded ribonucleic acid molecule includes single stranded RNA molecules forming functional stem-loop structures, such as small temporal RNAs, short hairpin RNAs and microRNAs, thereby forming the structural equivalent of an RNA duplex with single strand overhangs. The RNA molecule may be isolated, purified, native or recombinant, and may be modified by the addition, deletion, substitution and/or alteration of one or more nucleotides, including non-naturally occurring nucleotides, also including those added at 5' and/or 3' ends to increase nuclease resistance.

The double-stranded ribonucleic acid molecule may be any one of a number of non-coding RNAs (i.e., RNA which is not mRNA, tRNA or rRNA), including, preferably, a small interfering RNA, but may also comprise a small temporal RNA, small nuclear RNA, small nuclear RNA, short hairpin RNA or a microRNA having either a double-stranded structure or a stem loop configuration comprising an RNA duplex with or without single strand overhangs. The double-stranded RNA molecule may be very large, comprising thousands of nucleotides, or preferably in the case of siRNA protocols involving mammalian cells, may be small, in the range of about 15 to about 25 nucleotides, preferably in the range of about 15 to about 19 nucleotides.

The phrase "small interfering RNA" or "siRNA" as used herein, refers to a double stranded RNA duplex of any length, with or without single strand overhangs, wherein at least one strand, putatively the antisense strand, is homologous to the target mRNA to be degraded. The difference between antisense and double stranded small interfering molecules is that an antisense molecule is a single stranded oligonucleotide which is complementary to a section of the target RNA and must hybridize or bind to it in a 1:1 ratio in order to cause its degradation. In contrast, siRNA provides a substrate for the RNA-induced silencing complex (RISC), and unlike antisense, is inactive until incorporated into this macromolecular complex. This RISC complex is then guided by the unwound siRNA to its target gene. Once the target gene is located, it is destroyed by cleaving the target gene into small pieces, and thereby preventing its expression.

In a preferred embodiment, the siRNA comprises a double-stranded RNA duplex of at least about 15, or preferably at least about 19, nucleotides with no overhanging nucleotides. In another embodiment, the siRNA has nucleotide overhangs. For example, the siRNA may have two nucleotide overhangs, thus the siRNA will comprise a 21 nucleotide sense strand and a 21 nucleotide antisense strand paired so as to have a 19 nucleotide duplex region. The number of nucleotides in the overhang can be in the range of about 1 to about 6 homologous nucleotide overhangs at each of the 5' and 3' ends, preferably, about 2-4, more preferably, about 3 homologous nucleotide overhangs at each of the 5' and 3' ends. The nucleotides overhang can be modified, for example to increase nuclease resistance. For example, the 3' overhang can comprise 2' deoxynucleotides, e.g., TT, for improved nuclease resistance.

"Inhibitors", "activators", and "modulators" refer to activating, inhibitory, or modulating molecules identified using in vitro and in vivo assays of, e.g., SirT1 activity or expression, as disclosed herein. Inhibitors are compounds that, e.g., bind to, partially or totally block activity, decrease, prevent, delay activation, inactivate, desensitize, or down regulate the activity or expression of a protein, such as SirT1, or a cell pathway or function, e.g., transcription activation or apoptosis, disclosed herein, e.g., antagonists. "Activators" are compounds that increase, open, activate, facilitate, enhance activation, sensitize, agonize, or up regulate expression or activity of a protein, such as SirT1, or a cell pathway or function, e.g., cell proliferation, protein degradation or tumorigenesis s, disclosed herein, e.g., agonists. Inhibitors, activators, or modulators also include genetically modified versions of, e.g., SirT1, disclosed herein, e.g., versions with altered activity, as well as naturally occurring and synthetic ligands, antagonists, agonists, antibodies, peptides, cyclic peptides, nucleic acids, antisense molecules, ribozymes, small chemical molecules and the like. Such assays for inhibitors and activators include, e.g., expressing SirT1 protein disclosed herein in vitro, in cells, or cell membranes or in animals, applying putative modulator compounds, and then determining effects on activity.

Samples or assays comprising a SirT1 protein disclosed herein that are treated with a potential activator, inhibitor, or modulator are compared to control samples without the inhibitor, activator, or modulator to examine the extent of inhibition. Control samples (untreated with inhibitors) are assigned a relative protein activity or expression value of 100%. Inhibition is achieved when the activity or expression value relative to the control is about 80%, preferably 50%, more preferably 25-0%. Activation is achieved when the activity value relative to the control (untreated with activators) is 110%, more preferably 150%, more preferably 200-500% (i.e., two to five fold higher relative to the control), more preferably 1000-3000% higher.

The term "test compound" or "drug candidate" or "modulator" or grammatical equivalents as used herein describes any molecule, either naturally occurring or synthetic, e.g., protein, nucleic acid, including dsRNA or siRNA molecules, oligopeptide (e.g., from about 5 to about 25 amino acids in length, preferably from about 10 to 20 or 12 to 18 amino acids in length, preferably 12, 15, or 18 amino acids in length), small organic molecule, polysaccharide, lipid, fatty acid, polynucleotide, oligonucleotide, etc., to be tested for the capacity to directly or indirectly modulation tumor cell proliferation. The test compound can be in the form of a library of test compounds, such as a combinatorial or randomized library that provides a sufficient range of diversity. Test compounds are optionally linked to a fusion partner, e.g., targeting compounds, rescue compounds, dimerization compounds, stabilizing compounds, addressable compounds, and other functional moieties. Conventionally, new chemical entities with useful properties are generated by identifying a test compound (called a "lead compound") with some desirable property or activity, e.g., inhibiting activity, creating variants of the lead compound, and evaluating the property and activity of those variant compounds. Often, high throughput screening (HTS) methods are employed for such an analysis.

A "small organic molecule" refers to an organic molecule, either naturally occurring or synthetic, that has a molecular weight of more than about 50 daltons and less than about 2500 daltons, preferably less than about 2000 daltons, preferably between about 100 to about 1000 daltons, more preferably between about 200 to about 500 daltons.

"Biological sample" includes sections of tissues such as biopsy and autopsy samples, and frozen sections taken for histologic purposes. Such samples include blood, sputum, tissue, cultured cells, e.g., primary cultures, explants, and transformed cells, stool, urine, etc. A biological sample is typically obtained from a eukaryotic organism, most preferably a mammal such as a primate e.g., chimpanzee or human; cow; dog; cat; a rodent, e.g., guinea pig, rat, mouse; rabbit; or a bird; reptile; or fish.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the disclosure.

Those of skill recognize that many amino acids can be substituted for one another in a protein without affecting the function of the protein, i.e., a conservative substitution can be the basis of a conservatively modified variant of a protein such as a SirT1 protein and derivatives thereof. An incomplete list of conservative amino acid substitutions follows. The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V), Alanine (A); 6) Phenylalanine (F), Tyrosine (Y), Tryptophan (W); 7) Serine(S), Threonine (T), Cysteine (C); and 8) Cysteine (C), Methionine (M) (see, e.g., Creighton, Proteins (1984)).

The term "nucleic acid" refers to a deoxyribonucleotide or ribonucleotide polymer in either single- or double-stranded faun, and unless otherwise limited, encompasses known analogues of natural nucleotides that hybridize to nucleic acids in manner similar to naturally occurring nucleotides. Unless otherwise indicated, a particular nucleic acid sequence includes the complementary sequence thereof. The terms "nucleic acid", "nucleic acid sequence", and "polynucleotide" are used interchangeably herein.

The term "operably linked" refers to functional linkage between a nucleic acid expression control sequence (such as a promoter, signal sequence, or array of transcription factor binding sites) and a second nucleic acid sequence, wherein the expression control sequence affects transcription and/or translation of the nucleic acid corresponding to the second sequence.

The term "recombinant" when used with reference to a cell indicates that the cell replicates a heterologous nucleic acid, or expresses a peptide or protein encoded by a heterologous nucleic acid. Recombinant cells can contain genes that are not found within the native (non-recombinant) form of the cell. Recombinant cells can also contain genes found in the native form of the cell wherein the genes are modified and re-introduced into the cell by artificial means. The term also encompasses cells that contain a nucleic acid endogenous to the cell that has been modified without removing the nucleic acid from the cell; such modifications include those obtained by gene replacement, site-specific mutation, and related techniques.

A "recombinant nucleic acid" refers to a nucleic acid that was artificially constructed (e.g., formed by linking two naturally-occurring or synthetic nucleic acid fragments). This term also applies to nucleic acids that are produced by replication or transcription of a nucleic acid that was artificially constructed. A "recombinant polypeptide" is expressed by transcription of a recombinant nucleic acid (i.e., a nucleic acid that is not native to the cell or that has been modified from its naturally occurring form), followed by translation of the resulting transcript.

A "heterologous polynucleotide" or a "heterologous nucleic acid", as used herein, is one that originates from a source foreign to the particular host cell, or, if from the same source, is modified from its original form. Modification of the heterologous sequence may occur, e.g., by treating the DNA with a restriction enzyme to generate a DNA fragment that is capable of being operably linked to a promoter. Techniques such as site-directed mutagenesis are also useful for modifying a heterologous sequence.

A "subsequence" refers to a sequence of nucleic acids or amino acids that comprise a part of a longer sequence of nucleic acids or amino acids (e.g., polypeptide) respectively. A "recombinant expression cassette" or simply an "expression cassette" is a nucleic acid construct, generated recombinantly or synthetically, with nucleic acid elements that are capable of affecting expression of a structural gene in hosts compatible with such sequences. Expression cassettes include at least promoters and optionally, transcription termination signals. Typically, the recombinant expression cassette includes a nucleic acid to be transcribed (e.g., a nucleic acid encoding a desired polypeptide), and a promoter. Additional factors necessary or helpful in effecting expression may also be used as described herein. For example, an expression cassette can also include nucleotide sequences that encode a signal sequence that directs secretion of an expressed protein from the host cell. Transcription termination signals, enhancers, and other nucleic acid sequences that influence gene expression, can also be included in an expression cassette.

The term "isolated" refers to material that is substantially or essentially free from components which interfere with the activity of an enzyme. For cells, saccharides, nucleic acids, and polypeptides of the disclosure, the term "isolated" refers to material that is substantially or essentially free from components which normally accompany the material as found in its native state. Typically, isolated saccharides, proteins or nucleic acids of the disclosure are at least about 50%, 55%, 60%, 65%, 70%, 75%, 80% or 85% pure, usually at least about 90%, 91%, 92%, 93%, 94%, 95%, 96%, 97%, 98%, or 99% pure as measured by band intensity on a silver stained gel or other method for determining purity. Purity or homogeneity can be indicated by a number of means well known in the art, such as polyacrylamide gel electrophoresis of a protein or nucleic acid sample, followed by visualization upon staining. For certain purposes high resolution will be needed and HPLC or a similar means for purification utilized. For oligonucleotides, or other galactosylated products, purity can be determined using, e.g., thin layer chromatography, HPLC, or mass spectroscopy.

The terms "identical" or percent "identity," in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the following sequence comparison algorithms or by visual inspection.

The phrase "substantially identical," in the context of two nucleic acids or polypeptides, refers to two or more sequences or subsequences that have at least 60%, preferably 80% or 85%, most preferably at least 90%, 91%, 92%, 93%, 94%, 95%, 96%, 97%, 98%, or 99% nucleotide or amino acid residue identity, when compared and aligned for maximum correspondence, as measured using one of the following sequence comparison algorithms or by visual inspection. Preferably, the substantial identity exists over a region of the sequences that is at least about 50 residues in length, more preferably over a region of at least about 100 residues, and most preferably the sequences are substantially identical over at least about 150 residues. In a most preferred embodiment, the sequences are substantially identical over the entire length of the coding regions.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, *Current Protocols in Molecular Biology*, F. M. Ausubel et al., eds., Current Protocols, a joint venture between Greene Publishing Associates, Inc. and John Wiley & Sons, Inc., (1995 Supplement) (Ausubel)).

Examples of algorithms that are suitable for determining percent sequence identity and sequence similarity are the BLAST and BLAST 2.0 algorithms, which are described in Altschul et al. (1990) *J. Mol. Biol.* 215: 403-410 and Altschuel et al. (1977) *Nucleic Acids Res.* 25: 3389-3402, respectively. Software for performing BLAST analyses is publicly available through the National Center for Biotechnology Information (www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89:10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

The term "contacting" is used herein interchangeably with the following: combined with, added to, mixed with, passed over, incubated with, flowed over, etc. By "therapeutically effective dose" herein is meant a dose that produces effects for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); and Pickar, *Dosage Calculations* (1999)).

DETAILED DESCRIPTION

This disclosure discloses the surprising finding that inhibition of the activity or expression of the SirT1 protein results in reduced weight gain in a subject. In addition, inhibition in the activity or expression of the SirT1 protein results in treatment or prevention of obesity in an individual.

SIRT1 is one of seven mammalian sirtuins that are orthologs of yeast silencing information regulator 2 (ySir2). Sirtuins are the class III histone deacetylases (HDACs): these enzymes use nicotinamide adenine dinucleotide ($NAD^+$) as the cofactor to catalyze the deacetylation of acetyl-lysine residues of histones and non-histone proteins. The core domain of the Sirtuins, also known as the Sir2 domain, is highly conserved across the species. For example, the amino acid sequences for the core domain of human SIRT1 and murine SirT1 are identical.

SIRT1 is ubiquitously expressed in mammalian cells and tissues. Many of SIRT1's non-histone protein substrates are transcription factors, such as p53, FOXO, PPARγ, PGC-1α, and NF-κB. The change in the ratio of endogenous $NAD^+$ and nicotinamide affects the activity of SIRT1 in vivo. Activating SirT1 deacetylase has been reported to produce a desirable metabolic profile in mice (Cohen, H. Y. et al., *Science*, 305: 390-2 (2004); Bordone, L. et al., *Aging Cell* (2007). For example, resveratrol and its polyphenol analogues have been reported to activate the deacetylase activity of SIRT1 in an in vitro assay and to expand the lifespan of yeast and worms.

In one aspect, the present disclosure provides methods for treating or preventing obesity in a subject, the method comprising reducing the activity of a sirtuin 1 (SirT1) deacetylase protein in the subject. In one embodiment, the activity of a SirT1 deacetylase protein is reduced by the deletion of the exon 4 of the SirT1 gene that encodes NAD+ binding site of the Sir2 domain (Li, H. et al., *Breast Cancer Res*, 9:R1 (2007)). When such a deletion was introduced in mature adipocytes in adipocyte-specific SirT1 knockout (AKO-SIRT1) mice, the mice were resistant to fat diet-induced weight gain. The high fat-diet accelerated body growth in both AKOSIRT1 mice and littermate control mice after sexual maturity at 2 months of age. However, while control mice continued gaining weight and becoming overweight and obese, AKOSIRT1 mice maintained the normal maximum body weigh and body mass index for the rest of adulthood (Example 2). The results has revealed a previous undefined physiological switch that is similar to that in humans at 20 years of age for body growth and weight control after the sexual maturity. After this physiological switch and in response to fat diet, adipocyte SirT1 mediates fat storage and weight gain. Thus, reducing the activity adipocyte SirT1 in adult animals disconnects this association between fat diet and the gain of fat and body weight. In another embodiment, the activity of SirT1 deacetylase protein may be reduced by reducing the expression of the gene comprises RNA interference using a SirT1 specific siRNA or miRNA. Any known SirT1 specific siRNA or miRNA may be useful in the present disclosure. For example, double stranded RNA molecules, e.g., siRNA or RNAi, that inhibit cellular expression of SirT1 are disclosed in e.g., Vaquero et al., Mol Cell. 16:93-105 (2004); Ford et al., Cancer Res. 65:10457-10463 (2005); and Lan et al., *J Biol Chem*. Epub ahead of print Aug. 7, 2008; each of which is herein incorporated by reference for all purposes.

In a further embodiment, the activity of SirT1 deacetylase protein may be reduced by contacting an inhibitor with the protein, such that the activity of the protein is reduced. The inhibitor may be any sirtuin inhibitor. Representative sirtuin inhibitors useful in the present disclosure include, 1. 2-dihydro-3H-naphtho[2,1-b]pyran-3-one (Splitomicin, Bedalov, A., T. Gatbonton, et al. (2001). "Identification of a small molecule inhibitor of Sir2p." Proc Natl Acad Sci USA 98(26): 15113-8) and 8-Bromo-2-phenylsplitomicin (a Splitomicin derivative), and derivatives thereof.

2. 2-[[(2-hydroxy-1-naphthalenyl)methylene]amino]-N-(1-phenylethyl) benzamide (Sirtinol, Grozinger, C. M., E. D. Chao, et al. (2001). "Identification of a class of small molecule inhibitors of the sirtuin family of NAD-dependent deacetylases by phenotypic screening." J Biol Chem 276(42): 38837-43), and derivatives thereof.

3. 5-(2-hydroxynaphthalen-1-ylmethyl)-6-phenyl-2-thioxo-2,3-dihydro-1H-pyrimidin-4-one (Cambinol, tetrahydro-5-[(2-hydroxy-1-naphthalenyl)methyl]-6-phenyl-2-thioxo-4(1H)-pyrimidinone, or 5-[(2-hydroxy-1-naphthyl)methyl]-2-mercapto-6-phenyl-4(3H)-pyrimidin-one, Heltweg, B., T. Gatbonton, et al. (2006). "Antitumor activity of a small-molecule inhibitor of human silent information regulator 2 enzymes." Cancer Res 66(8): 4368-77), and 6-(4'-Bromophenyl)-5-[2"-hydroxynaphthyl-(1")-methyl]-2-thioxo-2,3-dihydro-1H-pyrimidin-4-one (a Cambinol derivative, Medda, F., R. J. Russell, et al. (2009). "Novel cambinol analogs as sirtuin inhibitors: synthesis, biological evaluation, and rationalization of activity." J Med Chem 52(9): 2673-82), and derivatives thereof 4. 6-Chloro-2,3,4,9-tetrahydro-1H-carbazole-1-carboxamide (EX 527) and indole derivatives (Napper, A. D., J. Hixon, et al. (2005). "Discovery of indoles as potent and selective inhibitors of the deacetylase SIRT1." J Med Chem 48(25): 8045-54), and derivatives thereof.

5. N-[[[4-(Acetylamino)phenyl]amino]thioxomethyl]-4-(1,1-dimethylethyl) benzamide (Tenovin-1),N-[[[4-[[5-(dimethylamino)-1-oxopentyl]amino]phenyl]amino]thioxomethyl]-4-(1,1-dimethylethyl)-benzamide (Tenovin-6), and Tenovin derivatives (Lain, S., J. J. Hollick, et al. (2008). "Discovery, in vivo activity, and mechanism of action of a small-molecule p53 activator." Cancer Cell 13(5): 454-63), and derivatives thereof 6. 3-[[3-(4-tert-butylphenyl)1,2,4-oxadiazole-5-carbonyl] amino]-1-[3-(trifluoro methyl) phenyl]thiourea (Oxadiazole-carbonylaminothioureas, Huhtiniemi, T., T. Suuronen, et al. (2008). "Oxadiazole-carbonylaminothioureas as SIRT1 and SIRT2 inhibitors." J Med Chem 51(15): 4377-80), and derivatives thereof.

7. 3,2',3',4'-tetrahydroxychalcone and Chalcone polyphenols (Kahyo, T., R. Mostoslaysky, et al. (2008). "Sirtuin-mediated deacetylation pathway stabilizes Werner syndrome protein." FEBS Lett 582(17): 2479-83), and derivatives thereof 8. 1-benzopyran-2-one and 3,4-dihydrocoumarin and Coumarin derivatives (Olaharski, A. J., J. Rine, et al. (2005). "The flavoring agent dihydrocoumarin reverses epigenetic silencing and inhibits sirtuin deacetylases." PLoS Genet 1(6): e77), and derivatives thereof.

9. N-(5-chinolyl)propenamide (AGK2, Outeiro, T. F., E. Kontopoulos, et al. (2007). "Sirtuin 2 inhibitors rescue alpha-synuclein-mediated toxicity in models of Parkinson's disease." Science 317(5837): 516-9), and a fragment thereof 10. Suramin (Trapp, J., R. Meier, et al. (2007). "Structure-activity studies on suramin analogues as inhibitors of NAD+-dependent histone deacetylases (sirtuins)." ChemMedChem 2(10): 1419-31), and derivatives thereof 11. Bis(indolyl)malcinimide (Trapp, J. and M. Jung (2006). "The role of NAD+dependent histone deacetylases (sirtuins) in ageing." Curr Drug Targets 7(11): 1553-60), and derivatives thereof.

12. Nicotinamide, Benzamide, 2-Anilinobenzamide, and derivatives thereof

13. N,N-bisbenzyliden-1,4-diamine (Kiviranta, P. H., J. Leppanen, et al. (2006). "N,N'-Bisbenzylidenebenzene-1,4-diamines and N,N'-Bisbenzylidenenaphthalene-1,4-diamines as Sirtuin Type 2 (SIRT2) Inhibitors." J Med Chem 49(26): 7907-11), and derivatives thereof.

14. Anthrachinone, and derivatives thereof

15. N-(3-phenylpropenoyl)-glycine tryptamide backbone (Kiviranta, P. H., H. S. Salo, et al. (2008). "Characterization of the binding properties of SIRT2 inhibitors with a N-(3-phenylpropenoyl)-glycine tryptamide backbone." Bioorg Med Chem 16(17): 8054-62), and derivatives thereof.

16. Aristoforin (Gartner, M., T. Muller, et al. (2005). "Aristoforin, a novel stable derivative of hyperforin, is a potent anticancer agent." Chembiochem 6(1): 171-7), and derivatives thereof.

17. Thiobarbiturates (Uciechowska, U., J. Schemies, et al. (2008). "Thiobarbiturates as sirtuin inhibitors: virtual screening, free-energy calculations, and biological testing." ChemMedChem 3(12): 1965-76), and derivatives thereof.

Each of the above references is herein incorporated by reference for all purposes. In practicing the methods of the disclosure, the activity of the SirT1 deacetylase protein may be specifically or selectively reduced in adipocytes of the subject without affecting the protein activity in other tissues or cells. In addition, reducing the activity of the SirT1 deacetylase protein may result in preventing weight gain, reducing weight gain, or reducing weight in the subject.

In another aspect, the present disclosure provides methods for treating or preventing obesity in a subject, the method comprising the step of administering an inhibitor of a sirtuin 1 (SirT1) deacetylase protein to the subject.

Weight gain is measured over time. Reduction of weight gain is an unexpected failure to gain weight from a baseline weight or an unexpectedly small weight gain from a baseline weight. Weight gain can result from, e.g., diet or aging of a subject. With regard to diet, weight gain can result from increases in caloric intake. In some cases, the type of calories ingested can result in weight gain, e.g., a fat diet or a high carbohydrate diet, especially refined carbohydrates. Thus, in some embodiments, a SirT1 inhibitor is administered to a subject while the subject ingests a diet that would typically lead to weight gain, e.g., a high fat or high carbohydrate diet. Weight gain is measured over time as long as the SirT1 inhibitor is administered to the subject and reduction in weight gain is based on comparison to a control subject or predicted value.

The inhibitor may be a siRNA molecule or a miRNA molecule interfering the expression of SirT1 protein, or a small molecule inhibiting the activity of SirT1 protein as a competitive or noncompetitive inhibitor. A comparison of SirT1 specific siRNA molecule and small molecule SirT1 inhibitors has been described in the literature (Kim et al., Mol. Cell 28(2):277-90, 2007). Other inhibitors of SirT1 activity useful in the disclosure are disclosed in Vergnes et al., Acta Trop. 94:107-115 (2005); and Neugebauer et al., *Curr Pharm Des.* 14:562-73 (2008). Each of above cited reference is herein incorporated by reference for all purposes.

In practicing the disclosure, the SirT1 inhibitor may be administered to the subject while the subject ingests a high fat diet. The subject may be a human, preferably an adult human. Alternatively, the subject may be a companion animal or a zoo animal. The SirT1 inhibitor may be administered to prevent weight gain, reduce weight gain, or reduce weight in the subject.

In another aspect, the present disclosure provides methods for identifying an inhibitor of weight gain in a subject. In one embodiment, the method comprises the steps of assaying an in vitro activity of a sirtuin 1 (SirT1) deacetylase protein in the presence and absence of a test compound, wherein a reduction in activity indicates that the test compound inhibits SirT1 deacetylase activity; and administering the test compound to a test subject and measuring the weight of the test subject, wherein the test subject gains less weight compared to a control subject that does not receive the test compound, thereby identifying an inhibitor of weight gain in a subject.

I. Methods for Identifying Inhibitors of SIRT1 Proteins that Inhibit Weight Gain A. Assays Modulation or inhibition of SirT1 activity disclosed herein, and corresponding modulation or reduction of weight gain by a subject can be assessed using a variety of in vitro and in vivo assays, including cell-based models. Such assays can be used to test for inhibitors of a SirT1 protein disclosed herein, and, consequently, agents that reduce weight gain in a subject. Modulators are tested using either recombinant or naturally occurring protein, preferably mammalian, more preferably a human SirT1 protein. Measurement of inhibition of SirT1 activity or expression using purified or partially purified protein or a cell expressing such a protein, either recombinant or naturally occurring, can be performed using a variety of assays, in vitro, in vivo, and ex vivo, as described herein.

A suitable physical, chemical or phenotypic change that affects activity, e.g., enzymatic activity, apoptosis, or ligand binding can be used to assess the influence of a test compound on the polypeptide of this disclosure. When the effects are determined using intact cells or animals, one can also measure a variety of effects, such as, ligand binding, transcriptional changes to both known and uncharacterized genetic markers (e.g., northern blots), changes in protein levels, e.g., SirT1 levels, changes in subcellular localization of a protein, e.g., SirT1, changes in cell metabolism, changes related to cellular proliferation, cell surface marker expression, and expression of SirT1 mRNA or protein.

In Vitro Assays

Assays to identify compounds with modulating activity can be performed in vitro. Such assays can used full length SirT1 protein or a variant thereof, or a fragment, such as an enzymatic domain. Purified recombinant or naturally occurring SirT1 protein can be used in the in vitro methods of the disclosure. In addition to purified protein, the recombinant or naturally occurring protein can be part of a cellular lysate or a cell membrane. As described below, the binding assay can be either solid state or soluble. Preferably, the SirT1 protein or membrane is bound to a solid support, either covalently or non-covalently. Often, the in vitro assays of the disclosure are ligand binding or ligand affinity assays, either non-competitive or competitive. Other in vitro assays include measuring changes in spectroscopic (e.g., fluorescence, absorbance, refractive index), hydrodynamic (e.g., shape), chromatographic, or solubility properties for the protein.

In one embodiment, a high throughput binding assay is performed in which the SirT1 protein or a fragment thereof is contacted with a potential modulator and incubated for a suitable amount of time. In one embodiment, the potential modulator is bound to a solid support, and the protein is added. In another embodiment, the protein is bound to a solid support. A wide variety of modulators can be used, as described below, including small organic molecules, peptides, antibodies, and ligand analogs. A wide variety of assays can be used to identify modulator binding, including labeled protein-protein binding assays, electrophoretic mobility shifts, immunoassays, enzymatic assays, and the like. In some cases, the binding of the candidate modulator is determined through the use of competitive binding assays, where interference with binding of a known ligand is measured in the presence of a potential modulator. Either the modulator or the known ligand is bound first, and then the competitor is added. After the protein is washed, interference with binding, either of the potential modulator or of the known ligand, is determined. Often, either the potential modulator or the known ligand is labeled. Fluorescent and fret-based SirT1 screening assay kits are commercially available, from, e.g., Cayman Chemical.

Cell-Based In Vivo Assays

In another embodiment, SirT1 protein is expressed in a cell, and functional changes are assayed to identify inhibitors of weight gain. Cells expressing the proteins of interest can also be used in binding assays and enzymatic assays. Any suitable functional effect can be measured, as described herein. For example, apoptosis assays can be used to determine the ability of SirT1 protein to deacetylate the p53 protein.

Cellular SirT1 polypeptide levels can be determined by measuring the level of protein or mRNA. The level of protein is measured using immunoassays such as western blotting, ELISA and the like with an antibody that selectively binds to the polypeptide or a fragment thereof. For measurement of mRNA, amplification, e.g., using PCR, LCR, or hybridization assays, e.g., northern hybridization, RNAse protection, dot blotting, are preferred. The level of protein or mRNA is detected using directly or indirectly labeled detection agents, e.g., fluorescently or radioactively labeled nucleic acids, radioactively or enzymatically labeled antibodies, and the like, as described herein.

Alternatively, protein expression can be measured using a reporter gene system. Such a system can be devised using a protein promoter operably linked to a reporter gene such as chloramphenicol acetyltransferase, firefly luciferase, bacterial luciferase, β-galactosidase and alkaline phosphatase. Furthermore, the protein of interest can be used as an indirect reporter via attachment to a second reporter such as red or green fluorescent protein (see, e.g., Mistili & Spector, *Nature Biotechnology* 15:961-964 (1997)). The reporter construct is typically transfected into a cell. After treatment with a potential modulator, the amount of reporter gene transcription, translation, or activity is measured according to standard techniques known to those of skill in the art. For testing the inhibitory activity of RNAi molecules SirT1 mRNA or protein levels are determined.

Animal Models

Animal models of obesity also find use in screening for modulators of obesity or weight gain. Similarly, transgenic animal technology including gene knockout technology, for example as a result of homologous recombination with an appropriate gene targeting vector, or gene overexpression, will result in the absence or increased expression of the protein. The same technology can also be applied to make knock-out cells. When desired, tissue-specific or age-specific expression or knockout of the protein may be necessary. Transgenic animals generated by such methods find use as animal models of cellular proliferation and are additionally useful in screening for modulators of cellular proliferation.

Knock-out cells and transgenic mice can be made by insertion of a marker gene or other heterologous gene into an endogenous gene site in the mouse genome via homologous recombination. Such mice can also be made by substituting an endogenous gene with a mutated version of the gene, or by mutating an endogenous gene, e.g., by exposure to carcinogens.

A DNA construct is introduced into the nuclei of embryonic stem cells. Cells containing the newly engineered genetic lesion are injected into a host mouse embryo, which is re-implanted into a recipient female. Some of these embryos develop into chimeric mice that possess germ cells partially derived from the mutant cell line. Therefore, by breeding the chimeric mice it is possible to obtain a new line of mice containing the introduced genetic lesion (see, e.g., Capecchi et al., *Science* 244:1288 (1989)). Chimeric targeted mice can be derived according to Hogan et al., *Manipulating the Mouse Embryo: A Laboratory Manual*, Cold Spring Harbor Laboratory (1988) and *Teratocarcinomas and Embryonic Stem Cells: A Practical Approach*, Robertson, ed., IRL Press, Washington, D.C., (1987).

Once an inhibitor of a SirT1 protein has been identified, transgenic or non-transgenic animals can be used to determine the specificity and toxicity of this inhibitor as a test compound in vivo, such as the effect on control of food intake and body weight as well as its utility for treating obesity or preventing weight gain. The specificity is referred to its specific inhibitory effect on SirT1 as compared to other sirtuins. Preferably laboratory animals, mice, rats, rabbits, hamsters, and primates, are used as test animals. A test compound is administered to the test animal. The food intake and body weight of the test animal are measured and compared to control animals that have not received the test compound. In a preferred embodiment, the test and control animals are adult animals. The experiment is carried out over a period of time, which can vary, depending on, e.g., the lifespan of the animal. Typically, weight and food intake are determined every week or bi-weekly. The type of food can also be varied. In a preferred embodiment, the test and control animals are fed a high fat diet. A reduced weight gain as compared to the control of at least 5%, 10%, 20%, 25%, 30%, 40%, 50%, 60%, 70%, 75%, 80%, 90% indicates that a test compound is an inhibitor of weight gain in a subject.

B. Modulators

The compounds tested as modulators of SirT1 activity can be any small organic molecule, or a biological entity, such as a protein, an antibody or peptide, a sugar, a nucleic acid, e.g., an siRNA molecule, an antisense oligonucleotide or a ribozyme, or a lipid.

Alternatively, modulators can be genetically altered versions of the protein. Typically, test compounds will be a dsRNA molecule, an siRNA molecule, small organic molecules, peptides, lipids, and lipid analogs.

Essentially any chemical compound can be used as a potential modulator or ligand in the assays of the disclosure, although most often compounds can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs Switzerland) and the like.

In one preferred embodiment, high throughput screening methods involve providing a combinatorial small organic molecule or peptide library containing a large number of potential therapeutic compounds (potential modulator or ligand compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks. Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487-493 (1991) and Houghton et al., Nature 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication No. WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909-6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217-9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology,* 14(3):309-314 (1996) and PCT/US. 96/10287), carbohydrate libraries (see, e.g., Liang et al., *Science,* 274:1520-1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525, 735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

C. Solid State and Soluble High Throughput Assays

In one embodiment the disclosure provides soluble assays using a SirT1 protein disclosed herein, or a cell or tissue expressing such a protein, either naturally occurring or recombinant. In another embodiment, the disclosure provides solid phase based in vitro assays in a high throughput format, where the SirT1 protein is attached to a solid phase substrate. Any one of the assays described herein can be adapted for high throughput screening.

In the high throughput assays of the disclosure, either soluble or solid state, it is possible to screen up to several thousand different modulators or ligands in a single day. This methodology can be used for proteins in vitro, or for cell-based or membrane-based assays comprising a protein of interest. In particular, each well of a microtiter plate can be used to run a separate assay against a selected potential modulator, or, if concentration or incubation time effects are to be observed, every 5-10 wells can test a single modulator. Thus, a single standard microtiter plate can assay about 100 (e.g., 96) modulators. If 1536 well plates are used, then a single plate can easily assay from about 100-about 1500 different compounds. It is possible to assay many plates per day; assay screens for up to about 6,000, 20,000, 50,000, or more than 100,000 different compounds are possible using the integrated systems of the disclosure.

For a solid state reaction, the protein of interest or a fragment thereof, e.g., an extracellular domain, or a cell or membrane comprising the protein of interest or a fragment thereof as part of a fusion protein can be bound to the solid state component, directly or indirectly, via covalent or non covalent linkage e.g., via a tag. The tag can be any of a variety of components. In general, a molecule which binds the tag (a tag binder) is fixed to a solid support, and the tagged molecule of interest is attached to the solid support by interaction of the tag and the tag binder.

A number of tags and tag binders can be used, based upon known molecular interactions well described in the literature. For example, where a tag has a natural binder, for example, biotin, protein A, or protein G, it can be used in conjunction with appropriate tag binders (avidin, streptavidin, neutravidin, the Fc region of an immunoglobulin, etc.) Antibodies to molecules with natural binders such as biotin are also widely available and appropriate tag binders; see, SIGMA Immunochemicals 1998 catalogue SIGMA, St. Louis Mo.).

Similarly, any haptenic or antigenic compound can be used in combination with an appropriate antibody to form a tag/tag binder pair. Thousands of specific antibodies are commercially available and many additional antibodies are described in the literature. For example, in one common configuration, the tag is a first antibody and the tag binder is a second antibody which recognizes the first antibody. In addition to antibody-antigen interactions, receptor-ligand interactions are also appropriate as tag and tag-binder pairs. For example, agonists and antagonists of cell membrane receptors (e.g., cell receptor-ligand interactions such as transferrin, c-kit, viral receptor ligands, cytokine receptors, chemokine receptors, interleukin receptors, immunoglobulin receptors and antibodies, the cadherein family, the integrin family, the selectin family, and the like; see, e.g., Pigott & Power, *The Adhesion Molecule Facts Book I* (1993). Similarly, toxins and venoms, viral epitopes, hoiniones (e.g., opiates, steroids, etc.), intracellular receptors (e.g. which mediate the effects of various small ligands, including steroids, thyroid hormone, retinoids and vitamin D; peptides), drugs, lectins, sugars, nucleic acids (both linear and cyclic polymer configurations), oligosaccharides, proteins, phospholipids and antibodies can all interact with various cell receptors.

Synthetic polymers, such as polyurethanes, polyesters, polycarbonates, polyureas, polyamides, polyethyleneimines, polyarylene sulfides, polysiloxanes, polyimides, and polyacetates can also form an appropriate tag or tag binder. Many other tag/tag binder pairs are also useful in assay systems described herein, as would be apparent to one of skill upon review of this disclosure.

Common linkers such as peptides, polyethers, and the like can also serve as tags, and include polypeptide sequences, such as poly gly sequences of between about 5 and 200 amino acids. Such flexible linkers are known to persons of skill in the art. For example, poly(ethelyne glycol) linkers are available from Shearwater Polymers, Inc. Huntsville, Ala. These linkers optionally have amide linkages, sulfhydryl linkages, or heterofunctional linkages.

Tag binders are fixed to solid substrates using any of a variety of methods currently available. Solid substrates are commonly derivatized or functionalized by exposing all or a portion of the substrate to a chemical reagent which fixes a chemical group to the surface which is reactive with a portion of the tag binder. For example, groups which are suitable for attachment to a longer chain portion would include amines, hydroxyl, thiol, and carboxyl groups. Aminoalkylsilanes and hydroxyalkylsilanes can be used to functionalize a variety of surfaces, such as glass surfaces. The construction of such solid phase biopolymer arrays is well described in the literature. See, e.g., Merrifield, *J. Am. Chem. Soc.* 85:2149-2154 (1963) (describing solid phase synthesis of, e.g., peptides); Geysen et al., *J. Immun. Meth.* 102:259-274 (1987) (describing synthesis of solid phase components on pins); Frank & Doring, *Tetrahedron* 44:60316040 (1988) (describing synthesis of various peptide sequences on cellulose disks); Fodor et al., *Science,* 251:767-777 (1991); Sheldon et al., *Clinical Chemistry* 39(4):718-719 (1993); and Kozal et al., *Nature Medicine* 2(7):753759 (1996)(all describing arrays of biopolymers fixed to solid substrates). Non-chemical approaches for fixing tag binders to substrates include other common methods, such as heat, cross-linking by UV radiation, and the like II. Molecular Biology and Biochemical Techniques A. Isolation of Nucleic Acids Encoding SirT1 Polypeptides Nucleic acids that encode SirT1 polypeptides include nucleic acids that encode the full-length, naturally occurring SirT1 polypeptides described above and enzymatically active truncations of those sequences. The SirT1 polypeptides of the disclosure deacetylate proteins, e.g., histone proteins, and assays to measure that activity are disclosed herein.

Nucleic acids that encode additional SirT1 polypeptides based on the information disclosed herein, and methods of obtaining such nucleic acids, are known to those of skill in the art. Suitable nucleic acids (e.g., cDNA, genomic, or subsequences (probes)) can be cloned, or amplified by in vitro methods such as the polymerase chain reaction (PCR), the ligase chain reaction (LCR), the transcription-based amplification system (TAS), or the self-sustained sequence replication system (SSR). A wide variety of cloning and in vitro amplification methodologies are well-known to persons of skill. Examples of these techniques and instructions sufficient to direct persons of skill through many cloning exercises are found in Berger and Kimmel, *Guide to Molecular Cloning Techniques, Methods in Enzymology* 152 Academic Press, Inc., San Diego, Calif. (Berger); Sambrook et al. (1989) *Molecular Cloning—A Laboratory Manual* (2nd ed.) Vol. 1-3, Cold Spring Harbor Laboratory, Cold Spring Harbor Press, N.Y., (Sambrook et al.); *Current Protocols in Molecular Biology,* F. M. Ausubel et al., eds., Current Protocols, a joint venture between Greene Publishing Associates, Inc. and John Wiley & Sons, Inc., (1994 Supplement) (Ausubel); Cashion et al., U.S. Pat. No. 5,017,478; and Carr, European Patent No. 0,246,864. Standard molecular biology methods, e.g., PCR, can be used to generate truncations of any known SirT1 sequence.

A DNA that encodes a SirT1 polypeptide, or a subsequence or truncation thereof, can be prepared by any suitable method described above, including, for example, cloning and restriction of appropriate sequences with restriction enzymes. In one embodiment, nucleic acids encoding SirT1 polypeptides are isolated by routine cloning methods. Nucleic acid sequences can be used to provide probes that specifically hybridize to a gene encoding a SirT1 polypeptide in a genomic DNA sample; or to an mRNA, encoding a SirT1 polypeptide in a total RNA sample (e.g., in a Southern or Northern blot). Once the target nucleic acid encoding a SirT1 polypeptide is identified, it can be isolated according to standard methods known to those of skill in the art (see, e.g., Sambrook et al. (1989) *Molecular Cloning: A Laboratory Manual,* 2nd Ed., Vols. 1-3, Cold Spring Harbor Laboratory; Berger and Kimmel (1987) *Methods in Enzymology, Vol.* 152: *Guide to Molecular Cloning Techniques,* San Diego: Academic Press, Inc.; or Ausubel et al. (1987) *Current Protocols in Molecular Biology,* Greene Publishing and Wiley-Interscience, New York). Further, the isolated nucleic acids can be cleaved with restriction enzymes to create nucleic acids encoding the full-length a SirT1 polypeptide, or subsequences or truncation variants thereof, e.g., truncations containing subsequences encoding at least a subsequence of a catalytic domain of a SirT1 polypeptide. These restriction enzyme fragments, encoding a SirT1 polypeptide or subsequences thereof, may then be ligated.

A nucleic acid encoding a SirT1 polypeptide, or a subsequence thereof, can be characterized by assaying for the expressed product. Assays based on the detection of the physical, chemical, or immunological properties of the expressed protein can be used. For example, one can identify a cloned SirT1 polypeptide, by the ability of a protein encoded by the nucleic acid to catalyze Also, a nucleic acid encoding SirT1 polypeptide, or a subsequence thereof, can be chemically synthesized. Suitable methods include the phosphotriester method of Narang et al. (1979) *Meth. Enzymol.* 68: 90-99; the phosphodiester method of Brown et al. (1979) *Meth. Enzymol.* 68: 109-151; the diethylphosphoramidite method of Beaucage et al. (1981) *Tetra. Lett.,* 22: 1859-1862; and the solid support method of U.S. Pat. No. 4,458,066. Chemical synthesis produces a single stranded oligonucleotide. This can be converted into double stranded DNA by hybridization with a complementary sequence, or by polymerization with a DNA polymerase using the single strand as a template. One of skill recognizes that while chemical synthesis of DNA is often limited to sequences of about 100 bases, longer sequences may be obtained by the ligation of shorter sequences. Nucleic acids encoding SirT1 polypeptides, or subsequences thereof, can be cloned using DNA amplification methods such as polymerase chain reaction (PCR). Thus, for example, the nucleic acid sequence or subsequence is PCR amplified, using a sense primer containing one restriction enzyme site (e.g., NdeI) and an antisense primer containing another restriction enzyme site (e.g., HindIII). This will produce a nucleic acid encoding the desired SirT1 polypeptide or a subsequence and having terminal restriction enzyme sites. This nucleic acid can then be easily ligated into an expression vector having the appropriate corresponding restriction enzyme sites. Suitable PCR primers can be determined by one of skill in the art using the sequence information provided in GenBank or other sources. Appropriate restriction enzyme sites can also be added to the nucleic acid encoding the SirT1 polypeptide or a protein subsequence thereof by site-directed mutagenesis. The plasmid containing the SirT1 polypeptide-encoding nucleotide sequence or subsequence is cleaved with the appropriate restriction endonuclease and then ligated into an appropriate vector for amplification and/or expression according to standard methods. Examples of techniques sufficient to direct persons of skill through in vitro amplification methods are found in Berger, Sambrook, and Ausubel, as well as Mullis et al., (1987) U.S. Pat. No. 4,683,202; *PCR Protocols A Guide to Methods and Applications* (Innis et al., eds) Academic Press Inc. San Diego, Calif. (1990) (Innis); Arnheim & Levinson (Oct. 1, 1990) *C&EN* 36-47; *The Journal Of NIH Research* (1991) 3: 81-94; (Kwoh et al. (1989) *Proc. Natl. Acad. Sci. USA* 86: 1173; Guatelli et al. (1990) *Proc. Natl. Acad. Sci. USA* 87, 1874; Lomell et al. (1989) *J. Clin. Chem.*, 35: 1826; Landegren et al., (1988) *Science* 241: 1077-1080; Van Brunt (1990) *Biotechnology* 8: 291-294; Wu and Wallace (1989) *Gene* 4: 560; and Barringer et al. (1990) *Gene* 89: 117.

Other physical properties of a recombinant SirT1 polypeptide expressed from a particular nucleic acid, can be compared to properties of known SirT1 polypeptides to provide another method of identifying suitable sequences or domains of the SirT1 polypeptide that are determinants of acceptor substrate specificity and/or catalytic activity. Alternatively, a putative SirT1 polypeptide can be mutated, and its role as a SirT1 deacetylase polypeptide, or the role of particular sequences or domains established by detecting a variation in the structure of a carbohydrate normally produced by the unmutated, naturally-occurring, or control SirT1 polypeptide. Those of skill will recognize that mutation or modification of SirT1 polypeptide of the disclosure can be facilitated by molecular biology techniques to manipulate the nucleic acids encoding SirT1 polypeptide, e.g., PCR.

B. Expressing SirT1 Polypeptides in Host Cells

SirT1 proteins of the disclosure can be expressed in a variety of host cells, including *E. coli*, other bacterial hosts, and yeast. The host cells are preferably microorganisms, such as, for example, yeast cells, bacterial cells, or filamentous fungal cells. Examples of suitable host cells include, for example, *Azotobacter* sp. (e.g., *A. vinelandii*), *Pseudomonas* sp., *Rhizobium* sp., *Erwinia* sp., *Escherichia* sp. (e.g., *E. coli*), *Bacillus, Pseudomonas, Proteus, Salmonella, Serratia, Shigella, Rhizobia, Vitreoscilla, Paracoccus* and *Klebsiella* sp., among many others. The cells can be of any of several genera, including *Saccharomyces* (e.g., *S. cerevisiae*), *Candida* (e.g., *C. utilis, C. parapsilosis, C. krusei, C. versatilis, C. lipolytica, C. zeylanoides, C. guilliermondii, C. albicans*, and *C. humicola*), *Pichia* (e.g., *P. farinosa* and *P. ohmeri*), *Torulopsis* (e.g., *T. candida, T. sphaerica, T. xylinus, T. famata*, and *T. versatilis*), *Debaryomyces* (e.g., *D. subglobosus, D. cantarellii, D. globosus, D. hansenii*, and *D. japonicus*), *Zygosaccharomyces* (e.g., *Z. rouxii* and *Z. bailii*), *Kluyveromyces* (e.g., *K. marxianus*), *Hansenula* (e.g., *H. anomala* and *H. jadinii*), and *Brettanomyces* (e.g., *B. lambicus* and *B. anomalus*). Examples of useful bacteria include, but are not limited to, *Escherichia, Enterobacter, Azotobacter, Erwinia, Klebsielia, Bacillus, Pseudomonas, Proteus*, and *Salmonella*.

Typically, the polynucleotide that encodes the SirT1 polypeptides is placed under the control of a promoter that is functional in the desired host cell. An extremely wide variety of promoters are well known, and can be used in the expression vectors of the disclosure, depending on the particular application. Ordinarily, the promoter selected depends upon the cell in which the promoter is to be active. Other expression control sequences such as ribosome binding sites, transcription termination sites and the like are also optionally included. Constructs that include one or more of these control sequences are termed "expression cassettes." Accordingly, the disclosure provides expression cassettes into which the nucleic acids that encode fusion proteins are incorporated for high level expression in a desired host cell.

Expression control sequences that are suitable for use in a particular host cell are often obtained by cloning a gene that is expressed in that cell. Commonly used prokaryotic control sequences, which are defined herein to include promoters for transcription initiation, optionally with an operator, along with ribosome binding site sequences, include such commonly used promoters as the beta-lactamase (penicillinase) and lactose (lac) promoter systems (Change et al., *Nature* (1977) 198: 1056), the tryptophan (trp) promoter system (Goeddel et al., *Nucleic Acids Res.* (1980) 8: 4057), the tac promoter (DeBoer, et al., *Proc. Natl. Acad. Sci. U.S.A.* (1983) 80:21-25); and the lambda-derived $P_L$ promoter and N-gene ribosome binding site (Shimatake et al., *Nature* (1981) 292: 128). The particular promoter system is not critical to the disclosure, any available promoter that functions in prokaryotes can be used.

For expression of SirT1 proteins in prokaryotic cells other than *E. coli*, a promoter that functions in the particular prokaryotic species is required. Such promoters can be obtained from genes that have been cloned from the species, or heterologous promoters can be used. For example, the hybrid trp-lac promoter functions in *Bacillus* in addition to *E. coli*.

A ribosome binding site (RBS) is conveniently included in the expression cassettes of the disclosure. An RBS in *E. coli*, for example, consists of a nucleotide sequence 3-9 nucleotides in length located 3-11 nucleotides upstream of the initiation codon (Shine and Dalgarno, *Nature* (1975) 254: 34; Steitz, In *Biological regulation and development: Gene expression* (ed. R. F. Goldberger), vol. 1, p. 349, 1979, Plenum Publishing, NY).

For expression of the SirT1 proteins in yeast, convenient promoters include GAL1-10 (Johnson and Davies (1984) *Mol. Cell. Biol.* 4:1440-1448) ADH2 (Russell et al. (1983) *J. Biol. Chem.* 258:2674-2682), PHO5 (EMBO J. (1982) 6:675-680), and MFα (Herskowitz and Oshima (1982) in *The Molecular Biology of the Yeast Saccharomyces* (eds. Strathern, Jones, and Broach) Cold Spring Harbor Lab., Cold Spring Harbor, N.Y., pp. 181-209). Another suitable promoter for use in yeast is the ADH2/GAPDH hybrid promoter as described in Cousens et al., *Gene* 61:265-275 (1987). For filamentous fungi such as, for example, strains of the fungi *Aspergillus* (McKnight et al., U.S. Pat. No. 4,935,349), examples of useful promoters include those derived from *Aspergillus nidulans* glycolytic genes, such as the ADH3 promoter (McKnight et al., *EMBO J.* 4: 2093 2099 (1985)) and the tpiA promoter. An example of a suitable terminator is the ADH3 terminator (McKnight et al.).

Either Constitutive or Regulated Promoters can be Used in the Present Disclosure.

Regulated promoters can be advantageous because the host cells can be grown to high densities before expression of the fusion proteins is induced. High level expression of heterologous proteins slows cell growth in some situations. An inducible promoter is a promoter that directs expression of a gene where the level of expression is alterable by environmental or developmental factors such as, for example, temperature, pH, anaerobic or aerobic conditions, light, transcription factors and chemicals. Such promoters are referred to herein as "inducible" promoters, which allow one to control the timing of expression of the glycosyltransferase or enzyme involved in nucleotide sugar synthesis. For *E. coli* and other bacterial host cells, inducible promoters are known to those of skill in the art. These include, for example, the lac promoter, the bacteriophage lambda $P_L$ promoter, the hybrid trp-lac promoter (Amann et al. (1983) *Gene* 25: 167; de Boer et al. (1983) *Proc. Nat'l. Acad. Sci. USA* 80: 21), and the bacteriophage T7 promoter (Studier et al. (1986) *J. Mol. Biol.*; Tabor et al. (1985) *Proc. Nat'l. Acad. Sci. USA* 82: 1074-8). These promoters and their use are discussed in Sambrook et al., supra.

A construct that includes a polynucleotide of interest operably linked to gene expression control signals that, when placed in an appropriate host cell, drive expression of the polynucleotide is termed an "expression cassette." Expression cassettes that encode the fusion proteins of the disclosure are often placed in expression vectors for introduction into the host cell. The vectors typically include, in addition to an expression cassette, a nucleic acid sequence that enables the vector to replicate independently in one or more selected host cells. Generally, this sequence is one that enables the vector to replicate independently of the host chromosomal DNA, and includes origins of replication or autonomously replicating sequences. Such sequences are well known for a variety of bacteria. For instance, the origin of replication from the plasmid pBR322 is suitable for most Gram-negative bacteria. Alternatively, the vector can replicate by becoming integrated into the host cell genomic complement and being replicated as the cell undergoes DNA replication. A preferred expression vector for expression of the enzymes is in bacterial cells is pTGK, which includes a dual tac-gal promoter and is described in PCT Patent Application Publ. NO. WO98/20111.

The construction of polynucleotide constructs generally requires the use of vectors able to replicate in bacteria. A plethora of kits are commercially available for the purification of plasmids from bacteria (see, for example, EasyPrepJ, FlexiPrepJ, both from Pharmacia Biotech; StrataCleanJ, from Stratagene; and, QIAexpress Expression System, Qiagen). The isolated and purified plasmids can then be further manipulated to produce other plasmids, and used to transfect cells. Cloning in *Streptomyces* or *Bacillus* is also possible.

Selectable markers are often incorporated into the expression vectors used to express the polynucleotides of the disclosure. These genes can encode a gene product, such as a protein, necessary for the survival or growth of transformed host cells grown in a selective culture medium. Host cells not transformed with the vector containing the selection gene will not survive in the culture medium. Typical selection genes encode proteins that confer resistance to antibiotics or other toxins, such as ampicillin, neomycin, kanamycin, chloramphenicol, or tetracycline. Alternatively, selectable markers may encode proteins that complement auxotrophic deficiencies or supply critical nutrients not available from complex media, e.g., the gene encoding D-alanine racemase for Bacilli. Often, the vector will have one selectable marker that is functional in, e.g., *E. coli*, or other cells in which the vector is replicated prior to being introduced into the host cell. A number of selectable markers are known to those of skill in the art and are described for instance in Sambrook et al., supra.

Construction of suitable vectors containing one or more of the above listed components employs standard ligation techniques as described in the references cited above.

Isolated plasmids or DNA fragments are cleaved, tailored, and re-ligated in the form desired to generate the plasmids required. To confirm correct sequences in plasmids constructed, the plasmids can be analyzed by standard techniques such as by restriction endonuclease digestion, and/or sequencing according to known methods. Molecular cloning techniques to achieve these ends are known in the art. A wide variety of cloning and in vitro amplification methods suitable for the construction of recombinant nucleic acids are well-known to persons of skill. Examples of these techniques and instructions sufficient to direct persons of skill through many cloning exercises are found in Berger and Kimmel, *Guide to Molecular Cloning Techniques, Methods in Enzymology*, Volume 152, Academic Press, Inc., San Diego, Calif. (Berger); and Current Protocols in Molecular Biology, F. M. Ausubel et al., eds., *Current Protocols*, a joint venture between Greene Publishing Associates, Inc. and John Wiley & Sons, Inc., (1998 Supplement) (Ausubel).

A variety of common vectors suitable for use as starting materials for constructing the expression vectors of the disclosure are well known in the art. For cloning in bacteria, common vectors include pBR322 derived vectors such as pBLUESCRIPT™, and λ-phage derived vectors. In yeast, vectors include Yeast Integrating plasmids (e.g., YIp5) and Yeast Replicating plasmids (the YRp series plasmids) and pGPD-2. Expression in mammalian cells can be achieved using a variety of commonly available plasmids, including pSV2, pBC12BI, and p91023, as well as lytic virus vectors (e.g., vaccinia virus, adeno virus, and baculovirus), episomal virus vectors (e.g., bovine papillomavirus), and retroviral vectors (e.g., murine retroviruses).

The methods for introducing the expression vectors into a chosen host cell are not particularly critical, and such methods are known to those of skill in the art. For example, the expression vectors can be introduced into prokaryotic cells, including *E. coli*, by calcium chloride transformation, and into eukaryotic cells by calcium phosphate treatment or electroporation. Other transformation methods are also suitable.

Translational coupling may be used to enhance expression. The strategy uses a short upstream open reading frame derived from a highly expressed gene native to the translational system, which is placed downstream of the promoter, and a ribosome binding site followed after a few amino acid codons by a termination codon. Just prior to the termination codon is a second ribosome binding site, and following the termination codon is a start codon for the initiation of translation. The system dissolves secondary structure in the RNA, allowing for the efficient initiation of translation. See Squires, et. al. (1988), *J. Biol. Chem.* 263: 16297-16302.

The SirT1 polypeptides can be expressed intracellularly, or can be secreted from the cell. Intracellular expression often results in high yields. If necessary, the amount of soluble, active fusion protein may be increased by performing refolding procedures (see, e.g., Sambrook et al., supra.; Marston et al., *Bio/Technology* (1984) 2: 800; Schoner et al., *Bio/Technology* (1985) 3: 151). In embodiments in which the SirT1 polypeptides are secreted from the cell, either into the periplasm or into the extracellular medium, the DNA sequence is linked to a cleavable signal peptide sequence. The signal sequence directs translocation of the fusion protein through the cell membrane. An example of a suitable vector for use in *E. coli* that contains a promoter-signal sequence unit is pTA1529, which has the *E. coli* phoA promoter and signal sequence (see, e.g., Sambrook et al., supra.; Oka et al., *Proc. Natl. Acad. Sci. USA* (1985) 82: 7212; Talmadge et al., *Proc. Natl. Acad. Sci. USA* (1980) 77: 3988; Takahara et al., *J. Biol. Chem.* (1985) 260: 2670). In another embodiment, the SIRT1 proteins are fused to a subsequence of protein A or bovine serum albumin (BSA), for example, to facilitate purification, secretion, or stability.

The SirT1 polypeptides of the disclosure can also be further linked to other bacterial proteins. This approach often results in high yields, because normal prokaryotic control sequences direct transcription and translation. In *E. coli*, lacZ fusions are often used to express heterologous proteins. Suitable vectors are readily available, such as the pUR, pEX, and pMR100 series (see, e.g., Sambrook et al., supra.). For certain applications, it may be desirable to cleave the non-SirT1 amino acids from the fusion protein after purification. This can be accomplished by any of several methods known in the art, including cleavage by cyanogen bromide, a protease, or by Factor $X_a$ (see, e.g., Sambrook et al., supra.; Itakura et al., *Science* (1977) 198: 1056; Goeddel et al., *Proc. Natl. Acad. Sci. USA* (1979) 76: 106; Nagai et al., *Nature* (1984) 309: 810; Sung et al., *Proc. Natl. Acad. Sci. USA* (1986) 83: 561). Cleavage sites can be engineered into the gene for the fusion protein at the desired point of cleavage.

C. Purification of SirT1 Polypeptides

The SirT1 proteins of the present disclosure can be expressed, e.g., as intracellular proteins or as proteins that are secreted from the cell, and can be used in this form, in the methods of the present disclosure. For example, a crude cellular extract containing the expressed intracellular or secreted SirT1 polypeptide can used in the methods of the present disclosure.

Alternatively, the SirT1 polypeptide can be purified according to standard procedures of the art, including ammonium sulfate precipitation, affinity columns, column chromatography, gel electrophoresis and the like (see, generally, R. Scopes, *Protein Purification*, Springer-Verlag, N.Y. (1982), Deutscher, *Methods in Enzymology Vol. 182: Guide to Protein Purification.*, Academic Press, Inc. N.Y. (1990)). Substantially pure compositions of at least about 70, 75, 80, 85, 90% homogeneity are preferred, and 92, 95, 98 to 99% or more homogeneity are most preferred. The purified proteins may also be used, e.g., as immunogens for antibody production.

To facilitate purification of the SirT1 polypeptides of the disclosure, the nucleic acids that encode the proteins can also include a coding sequence for an epitope or "tag" for which an affinity binding reagent is available, i.e. a purification tag. Examples of suitable epitopes include the myc and V-5 reporter genes; expression vectors useful for recombinant production of fusion proteins having these epitopes are commercially available (e.g., Invitrogen (Carlsbad Calif.) vectors pcDNA3.1/Myc-His and pcDNA3.1/V5-His are suitable for expression in mammalian cells). Additional expression vectors suitable for attaching a tag to a SIRT1 polypeptide of the disclosure, and corresponding detection systems are known to those of skill in the art, and several are commercially available (e.g., FLAG" (Kodak, Rochester N.Y.). Another example of a suitable tag is a polyhistidine sequence, which is capable of binding to metal chelate affinity ligands. Typically, six adjacent histidines are used, although one can use more or less than six. Suitable metal chelate affinity ligands that can serve as the binding moiety for a polyhistidine tag include nitrilo-tri-acetic acid (NTA) (Hochuli, E. (1990) "Purification of recombinant proteins with metal chelating adsorbents" In Genetic Engineering: Principles and Methods, J. K. Setlow, Ed., Plenum Press, NY; commercially available from Qiagen (Santa Clarita, Calif.)). Other purification or epitope tags include, e.g., AU1, AU5, DDDDK (EC5), E tag, E2 tag, Glu-Glu, a 6 residue peptide, EYMPME, derived from the Polyoma middle T protein, HA, HSV, IRS, KT3, S tage, Si tag, T7 tag, V5 tag, VSV-G, β-galactosidase, Ga14, green fluorescent protein (GFP), luciferase, protein C, protein A, cellulose binding protein, GST (glutathione S-transferase), a step-tag, Nus-S, PPI-aces, Pfg 27, calmodulin binding protein, dsb A and fragments thereof, and granzyme B. Epitope peptides and antibodies that bind specifically to epitope sequences are commercially available from, e.g., Covance Research Products, Inc.; Bethyl Laboratories, Inc.; Abcam Ltd.; and Novus Biologicals, Inc.

Purification tags also include maltose binding domains and starch binding domains. Proteins comprising purification tags can be purified using a binding partner that binds the purification tag, e.g., antibodies to the purification tag, nickel or cobalt ions or resins, and amylose, maltose, or a cyclodextrin. Purification tags also include starch binding domains, *E. coli* thioredoxin domains (vectors and antibodies commercially available from e.g., Santa Cruz Biotechnology, Inc. and Alpha Diagnostic International, Inc.), and the carboxy-terminal half of the SUMO protein (vectors and antibodies commercially available from e.g., Life Sensors Inc.). Starch binding domains, such as a maltose binding domain from *E. coli* and SBD (starch binding domain) from an amylase of *A. niger*, are described in WO 99/15636, herein incorporated by reference. Affinity purification of a fusion protein comprising a starch binding domain using a betacyclodextrin (BCD)-derivatized resin is described in WO 2005/014779, published Feb. 17, 2005, herein incorporated by reference in its entirety. In some embodiments, a SirT1 polypeptide comprises more than one purification or epitope tag. Other haptens that are suitable for use as tags are known to those of skill in the art and are described, for example, in the Handbook of Fluorescent Probes and Research Chemicals (6th Ed., Molecular Probes, Inc., Eugene Oreg.). For example, dinitrophenol (DNP), digoxigenin, barbiturates (see, e.g., U.S. Pat. No. 5,414,085), and several types of fluorophores are useful as haptens, as are derivatives of these compounds. Kits are commercially available for linking haptens and other moieties to proteins and other molecules. For example, where the hapten includes a thiol, a heterobifunctional linker such as SMCC can be used to attach the tag to lysine residues present on the capture reagent.

One of skill would recognize that modifications can be made to the catalytic or functional domains of the SirT12 polypeptide without diminishing their biological activity. Some modifications may be made to facilitate the cloning, expression, or incorporation of the catalytic domain into a fusion protein. Such modifications are well known to those of skill in the art and include, for example, the addition of codons at either terminus of the polynucleotide that encodes the catalytic domain to provide, for example, a methionine added at the amino terminus to provide an initiation site, or additional amino acids (e.g., poly His) placed on either terminus to create conveniently located restriction enzyme sites or termination codons or purification sequences.

It must be noted that as used herein and in the appended claims, the singular forms "a", "and", and "the" include plural referents unless the context clearly dictates otherwise. Thus, for example, reference to "a nucleic acid" includes a plurality of such nucleic acids and reference to "the polypeptide" includes reference to one or more polypeptides and equivalents thereof known to those skilled in the art, and so forth.

The publications discussed herein are provided solely for their disclosure prior to the filing date of the present application. Nothing herein is to be construed as an admission that the present disclosure is not entitled to antedate such publication by virtue of prior disclosure. Further, the dates of publication provided may be different from the actual publication dates which may need to be independently confirmed. All citations are incorporated herein by reference.

III. Pharmaceutical Compositions and Administration

Pharmaceutically acceptable carriers are determined in part by the particular composition being administered (e.g., nucleic acid, protein, modulatory compounds or transduced cell), as well as by the particular method used to administer the composition. Accordingly, there are a wide variety of suitable formulations of pharmaceutical compositions of the present disclosure (see, e.g., *Remington's Pharmaceutical Sciences*, 17th ed., 1989). Administration can be in any convenient manner, e.g., by injection, oral administration, inhalation, transdermal application, or rectal administration.

Formulations suitable for oral administration can consist of (a) liquid solutions, such as an effective amount of the packaged nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art. The compound of choice, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this disclosure, compositions can be administered, for example, by intravenous infusion, orally, topically, intraperitoneally, intravesically or intrathecally. Parenteral administration and intravenous administration are the preferred methods of administration. The formulations of commends can be presented in unit-dose or multi-dose sealed containers, such as ampules and vials. Injection solutions and suspensions can be prepared from sterile powders, granules, and tablets of the kind previously described. Cells transduced by nucleic acids for ex vivo therapy can also be administered intravenously or parenterally as described above.

The dose administered to a patient, in the context of the present disclosure should be sufficient to effect a beneficial therapeutic response in the patient over time. The dose will be determined by the efficacy of the particular vector employed and the condition of the patient, as well as the body weight or surface area of the patient to be treated. The size of the dose also will be determined by the existence, nature, and extent of any adverse side-effects that accompany the administration of a particular vector, or transduced cell type in a particular patient.

In determining the effective amount of the vector to be administered in the treatment or prophylaxis of conditions owing to diminished or aberrant expression of the protein, the physician evaluates circulating plasma levels of the vector, vector toxicities, progression of the disease, and the production of anti-vector antibodies. In general, the dose equivalent of a naked nucleic acid from a vector is from about 1 µg to 100 µg for a typical 70 kilogram patient, and doses of vectors which include a retroviral particle are calculated to yield an equivalent amount of therapeutic nucleic acid.

For administration, compounds and transduced cells of the present disclosure can be administered at a rate determined by the LD-50 of the inhibitor, vector, or transduced cell type, and the side-effects of the inhibitor, vector or cell type at various concentrations, as applied to the mass and overall health of the patient. Administration can be accomplished via single or divided doses.

It must be noted that as used herein and in the appended claims, the singular forms "a", "and", and "the" include plural referents unless the context clearly dictates otherwise. Thus, for example, reference to "a nucleic acid" includes a plurality of such nucleic acids and reference to "the polypeptide" includes reference to one or more polypeptides and equivalents thereof known to those skilled in the art, and so forth.

The publications discussed herein are provided solely for their disclosure prior to the priority date of the present application. Nothing herein is to be construed as an admission that the present disclosure is not entitled to antedate such publication by virtue of prior disclosure. Further, the dates of publication provided may be different from the actual publication dates which may need to be independently confirmed. All citations are incorporated herein by reference.

EXAMPLES

Example 1

Materials and Methods

Animals and animal Care. All animal protocols used were approved by the Institutional Animal Care and Use Committee at the University of Washington. The generation and characterization of SirT1$^{co/co}$ mice carrying the SirT1 gene with floxed exon 4 were described (Li, H. et al., *Breast Cancer Res* 9, R1 (2007)). Both aP2-Cre transgenic mice [B6.Cg-Tg (Fabp4-cre)1Rev/J] and Mx1-Cre transgenic mice [B6.Cg-Tg(Mx1-cre)1Cgn/J] were purchased from the Jackson Laboratory (Bar Harbor, Me.). The breeding between the transgenic mice and SirT1$^{co/co}$ mice resulted in aP2-Cre, SirT1$^{+/co}$ mice and Mx1-Cre, SirT1$^{+/co}$ mice, respectively. These mice were backcross with SirT1$^{co/co}$ mice. Both AKO-SIRT1 mice and Mx1-Cre, SirT1$^{co/co}$ mice were identified from the offspring by using PCR-based genotyping methods. Three primers were used to identify wild type, co, and ko loci of the SirT1 gene in a single reaction: 15'co: 5'-GGTTGACT-TAGGTCTTGTCTG (SEQ ID NO 1), 5'ko: 5'-AGGCG-GATTTCTGAGTTCGA (SEQ ID NO2), 3': 5'-CGTCCCT-TGAAATGTTTCCC (SEQ ID NO 3). Both Cre transgenes can be identified by using generic Cre primers provided by the Jackson Laboratory. The two strains of mice were maintained as an inbred strain in a mixed background. To activate Mx1-Cre-mediated recombination in Mx1-Cre, SirT1$^{co/co}$ mice, polyinosinic-polycytidylic acid (also known as pI-pC from Sigma Aldrich) was injected into the mice at 3 weeks of age at 3×250 micrograms with 2-day interval. Mice were housed in a 6-a.m.-to-6-p.m. light cycle special barrier facility. Mice were provided ad libitum access to water and chow of either standard (PicoLab 5053; 20.0% protein, 5.0% fat) or fat diet (PicoLab 5058; 21.8% protein, 9.0% fat). Food consumption was measured by averaging the daily weight difference in the regular chow for 5 consecutive days. Mouse body mass index (BMI) was calculated by dividing weight in grams by anal nasal length in millimeters squared and by multiplying that result 10000.

Measurement of body weight and compositions. For adult mice, body weight was measured once every other week and the weight of relevant tissues was measured at the time of necropsy. Quantitative magnetic resonance (QMR) methods (Echo Medical Systems, Houston, Tex.) were also used to measure body composition. In these methods, a conscious mouse is placed in a sample holder and the sample holder is then inserted into the center of the magnetic resonance machine. Single measurement takes 2 minutes. For a typical experiment, each animal undergoes 3- to 5-replicate measurements. Respiration rates, food intake and body weight were closely monitored during and after the measurement.

Glucose tolerance test. Mice are fasted for 6 hours by removal to a clean cage without food at the end of their dark (feeding) cycle (between 7 am-1 pm). After 6 hours of fasting, mice are weighed and a fasting glucose level is obtained from venous blood from a small tail nick. It is measured with the OneTouch® Ultra Blood Glucose Monitoring System and test strips. Then, 1 mg/g body glucose is injected intraperitoneally and blood glucose values are obtained at 15, 30, 60, and 120 minutes.

RNA isolation. Total RNA was extracted from tissues using Trizol reagent (Gibco BRL) and the RNeasy kit (Qiagen). This included tissue samples from 3 pairs of littermate mice for WAT2 (n=6), WAT16 (n=6), and liver (n=6), and 3 pairs of e13.5 embryos for MEFs (n=6). RNA quality was evaluated with the Agilent 2100 Bioanalyzer, and the concentration determined using a ThermoScientific Nanodrop1000 UV spectrophotometer.

RNA labeling and microarray hybridization. Each RNA sample was amplified using the Ambion Illumina RNA amplification kit with biotin UTP (Enzo) labeling. T7 oligo (dT) primer was used to generate single stranded cDNA followed by a second strand synthesis to generate double-stranded cDNA, which is then column purified. T7 RNA polymerase was used to synthesize biotin-labeled cRNA in vitro. The cRNA was column purified and then checked for size/yield using the Agilent 2100 Bioanalyzer. A total of 1.5 microgram of cRNA was hybridized for each array using standard Illumina protocols with streptavidin-Cy3 (Amersham) being used for detection. Slides were scanned on an Illumina BeadStation and the results were analyzed using BeadStudio software.

Data analysis and normalization. Variance-stabilizing transformation (VST) was used to improve both the detection of differentially expressed genes and to reduce false positive identifications (Lin, S. M. et al., *Nucleic Acids Res* 36 (2), e11 (2008)). After performing VST, we applied quantile normalization across samples using the functions in the 'lumi' Bioconductor package to do all processing (available at www-.bioconductor.orf). For normalization we used the quantile method using the raw intensity data on the arrays (Bolstad, B. M. et al., *Bioinformatics* 19 (2), 185-193 (2003)). The scatter plots and Venn diagrams were generated using GeneSpring GX 7.3.1. Differentially expressed genes were selected using a modified t-statistic with 15% of the standard deviation percentile as the fudge constant and log 2 ratios, followed by Benjamini-Hochberg testing procedure for controlling FDR (False Discovery Rate) of 5% and permutation FDR of 8%, respectively (Satagopan, J. M. & Panageas, K. S., *Stat Med* 22 (3), 481-499 (2003)).

Hierarchical Clustering and significance analysis. The Euclidean distance metric and the Centroid linkage method were used to group data points by agglomerating them one-by-one into ever-growing groups. This grouping was achieved by first finding the shortest link among all of the data points, and then combining those two points into a group. The algorithm then finds the next shortest distance, including the distance from other points to this new group, and groups even further. The resulting clusters were displayed in the Heat Map with the associated Experiment Tree and Gene Tree on the horizontal and vertical axes, respectively.

Analysis of hits using gene ontology terms. Genes were categorized using the Panther classification system. For each molecular function, biological process or pathway term in PANTHER, the genes associated with that term were evaluated according to the likelihood that their numerical values were drawn randomly from the overall distribution of values (Mi, H. et al., *Nucleic Acids Res* 33 (Database issue), D284-288 (2005); Thomas, P. D. et al., *Nucleic Acids Res* 31 (1), 334-341 (2003)). The Mann-Whitney U Test (Wilcoxon Rank-Sum Test) was used to determine the P-value relative to overall list of values that were input (nominal P value=0.05).

Network analysis. Protein interaction networks were generated using Ingenuity Pathways Analysis (IPA, Ingenuity Systems, www.ingenuity.com). The focus genes were overlaid onto a global molecular network developed from direct and or indirect interactions, and sub-networks were algorithmically generated based on their connectivity (Wu, X. & Dewey, T. G., *Methods Mol Biol* 316, 35-48 (2006)). Pathways with a score greater than 4 (p<0.0001) were combined to form a composite network representing the underlying biological process.

Quantitative real-time RT-PCR. Quantitative real-time PCR was performed on identical samples used for Illumina BeadArrays. Mouse Diabesity Stellarrays (Bar Harbor Biosciences), a high-throughput 384-well real-time PCR platform, was utilized to measure simultaneous mRNA and DNA copy number changes. Triplicate RNA and DNA samples were compared with reference samples. Cycle threshold ($C_t$) values were normalized using quantile normalizations, and copy number changes were estimated by ANOVA using R/Maanova. The PCR reactions were performed in triplicates for each gene being validated. Primers used in this experiment can be found at bhbio.com/products/stellarray Example 2

Adipocytic SirT1 Mediates Fat Diet-Induced Weight Gain

Figure 11:
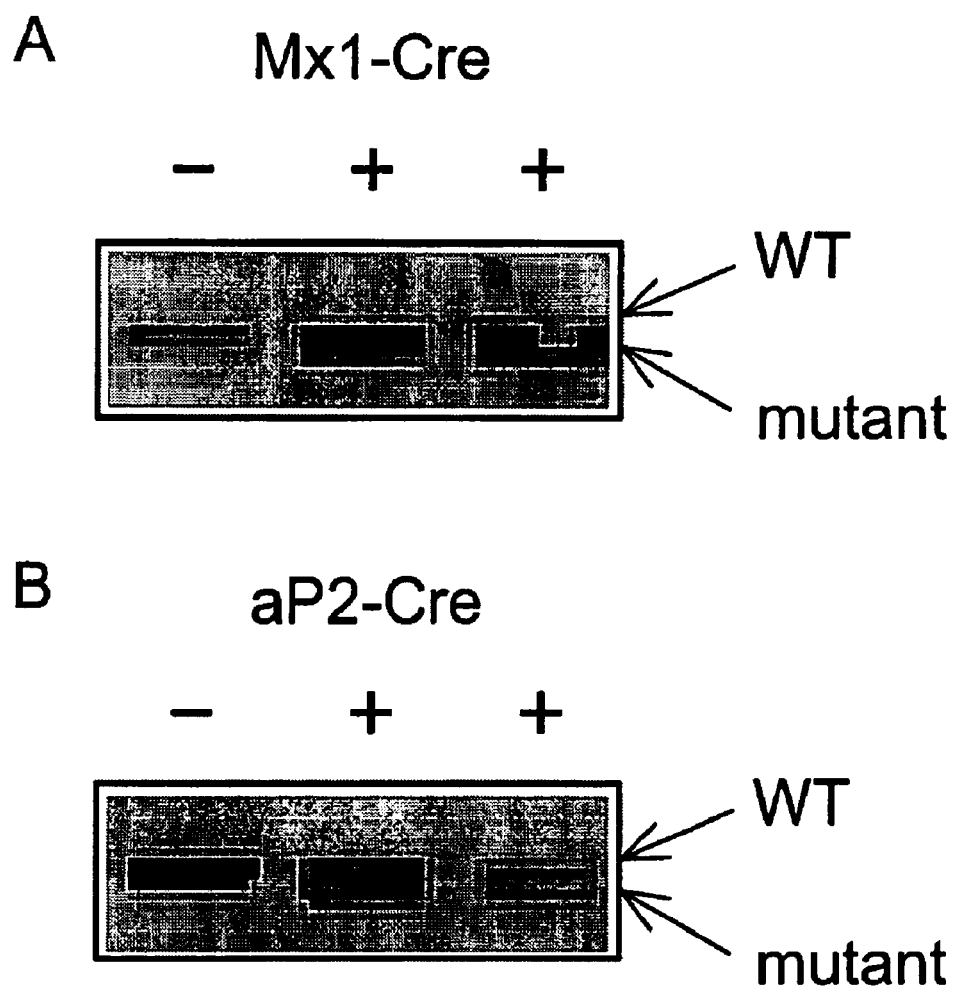
FIG. 11 shows the expression of a deacetylase-dead SirT1 mutant protein in adipocytes of adipocyte-specific SirT1 knockout (AKOSIRT1) mice and Mx1-Cre, SirT1 knockout mice. 11A shows the result of western blot analysis on the protein extract of white adipose tissue from AKOSIRT1 mice in which aP2-Cre transgene is expressed in mature adipocytes (+) and their littermate control mice in which aP2-Cre transgene is not present (−); and 11B shows that an injection of polyinosinic-polycytidylic acid into Mx1-Cre, SirT1 conditional knockout) (SirT1$^{co/co}$ mice at a pre-puberty age activates Mx1-Cre transgene-mediated SirT1 gene deletion (+) and results in the expression of SirT1 mutant protein in multiple lineages of cells and tissues including mammary gland consist of adipocytes.

Adipocyte knockout SIRT1 (AKOSIRT1) mice were generated by breeding SirT1 conditional knockout mice (Li, H. et al., *Breast Cancer Res*, 9:R1 (2007)) with aP2-Cre transgenic mice. The aP2-Cre transgene is expressed in mature adipocytes and activated macrophages (Pelton, P. D. et al., *Biochem Biophys Res Comtnun*, 261:456-8 (1999); Bluher, M. et al., *Dev Cell*, 3:25-38 (2002)). Because the expression of Cre recombinase mediates the deletion of the sequences flanked by loxP sequences, the exon 4 of the SirT1 gene is deleted in Cre-expressing cells, including germ cells, as shown in SirT1-deficient mice derived from crossing CMV-Cre transgene into SirT1 conditional knockout mice (Li, H. et al., *Breast Cancer Res*, 9:R1 (2007)). CMV-Cre transgene expresses in multiple lineages of cells including germ cells. In contrast, aP2-Cre transgene does not express in germ cells and only the mice harboring Cre-transgene may express a phenotype. As shown in FIG. 11*a*, a SirT1 mutant protein is produced in aP2-Cre expressing in adipose tissues in AKO-SIRT1 mice. The "deacetylase-dead" SirT1 mutant protein is encoded by the SirT1 gene harboring an in-frame deletion of exon 4 and lacks a part of NAD-binding site within the highly conserved Sir2 deacetylase domain. This signature SirT1 mutant protein is detected in all lineages of cells in SirT1-deficient mice (SirT1$^{co/co}$ mice, Li, H. et al., *Breast Cancer Res,* 9:R1 (2007)), as well as in many lineages of cells in Mx1-Cre$^+$, SirT1$^{co/co}$ mice after being treated with polyinosinic-polycytidylic acid, including mammary gland consist of adipocytes (FIG. 11*b*).

Obesity develops when food intake and fat storage exceed physiological requirements (Yach, D., Stuckler, D. & Brownell, K. D. *Nat Med,* 12:62-6 (2006); Ogden, C. L. et al., *Jama,* 295:1549-55 (2006)). While genetic factors modify the risk of obesity, environmental and lifestyle factors influence an individual's preference for food intake and physical activity. To determine how diet affects the outcome of the genetic predisposition to obesity, the effect of a modest fat diet was characterized on AKOSIRT1 mice.

Figure 8:
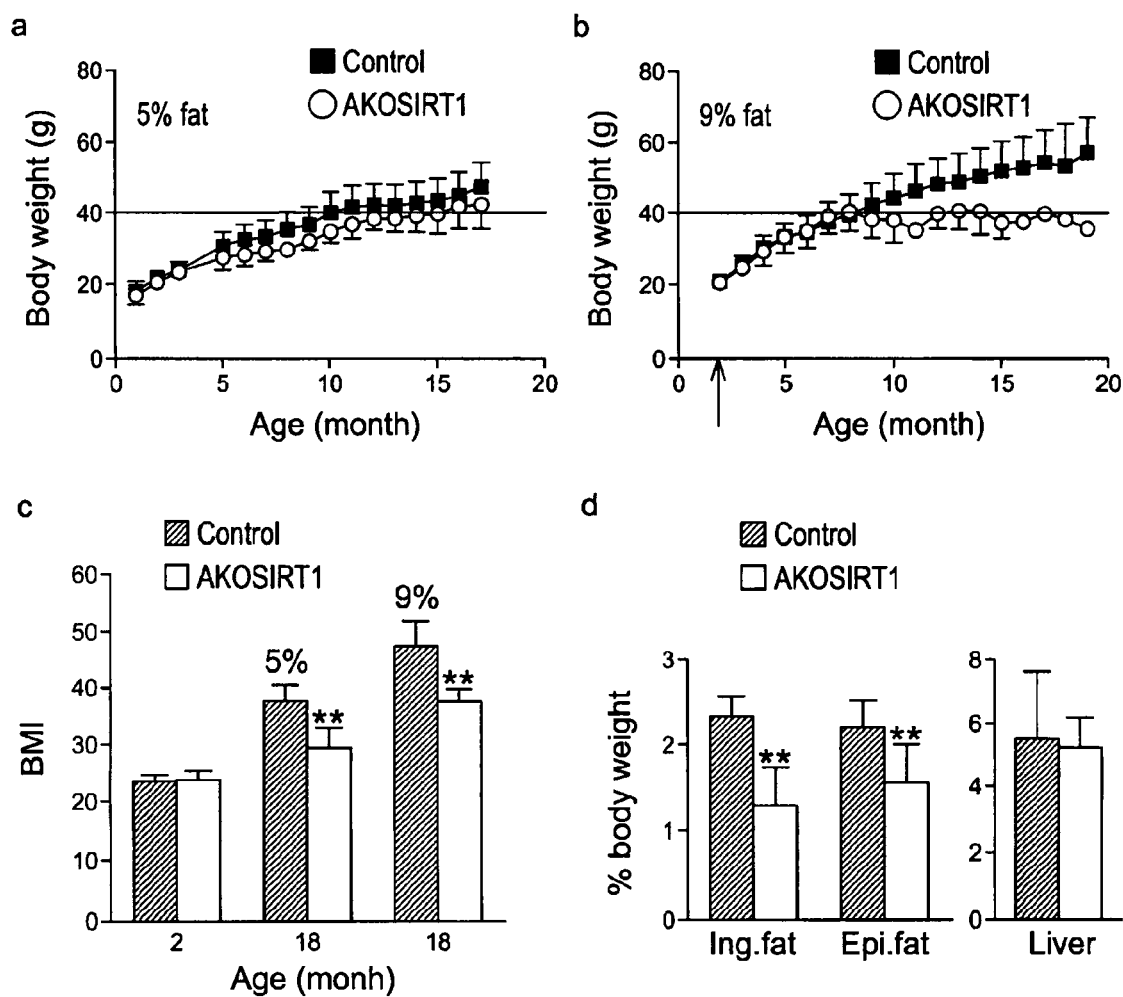
FIG. 8 shows that adipocyte SirT1 mediates diet-induced obesity in adult mice. 8A shows body weights in male mice (n=5) under the standard diet (5% fat); 8B shows body weights in male mice (n=5) fed a 9% fat diet starting at 2 months of age (arrow); 8C shows body mass index (BMI) at 2 and 18 months of age under the feeding condition of either 5% fat or 9% fat. p=0.71, 0.0017, and 0.021, respectively; and 8D shows WAT percentage in total body weight in AKPSIRTI mice at 18 months of age fed a modest fat diet (9% fat). Inguinal (Ing.) fat, p=0.0003; epididymal (Epi.) fat, p=0.008, and liver, p=0.89. Asterisks, p<0.01 (two-tailed t-test). Error bars indicate s.d.

When fed a standard diet (i.e. 5% fat), both AKOSIRT1 mice and control littemiates maximized their body weight (i.e. up to 45 grams) by 18 months of age prior to accelerated aging (FIG. 8*a*). When fed a 9% fat diet starting from 2 months of age, both mice maximized their body weight by 8 months of age (FIG. 8*b*). Beyond this point, control littermates continued a steady gain in body weight, whereas AKO-SIRT1 mice maintained their body weight at a stable level (FIG. 8*b*). By 18 months of age, control littermates became overweight and obese, as measured by their total body weight (up to 70 grams), body mass index (BMI), and WAT percentage in total body weight (FIG. 8*b*-8*d*). In contrast, AKO-SIRT1 mice maintained normal BMI and WAT percentage throughout their adult life despite the change in fat content in their diet (FIG. 8*c*). The divergent point concurred with the completion of normal body growth. Therefore, a physiological switch in the homeostatic control of body weight must take place and as a result, adipocytic SirT1 mediates fat diet-induced weight gain in mature adults.

Figure 9:
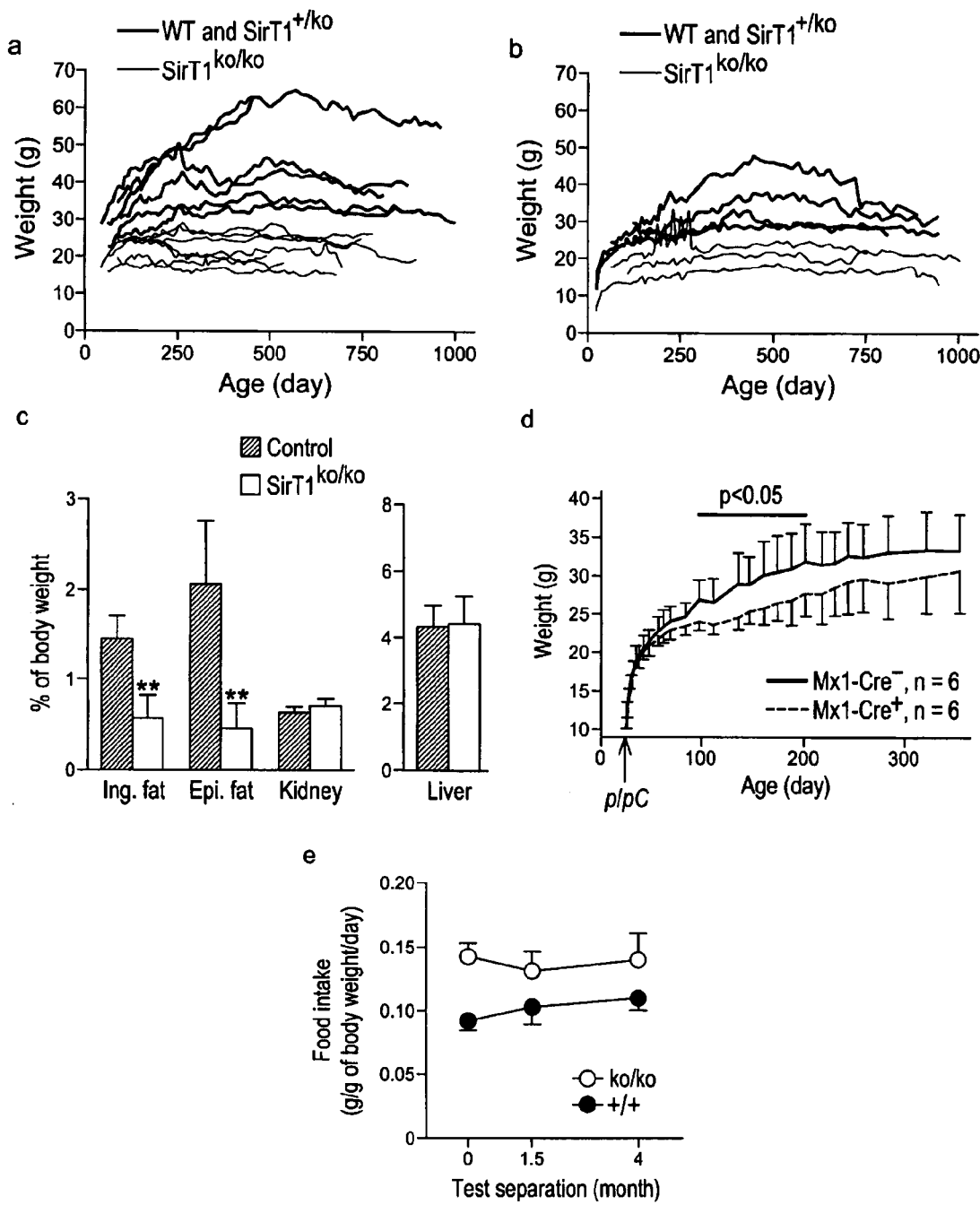
FIG. 9 shows that systemic SirT1 has a profound effect on control of body weight, fat mass, and food intake. 9A shows body weights of male mice after weaning; 9B shows body weights of female mice after weaning, including one SirT1$^{ko/ko}$ female showing five consecutive pregnancies (no pup survived); 9C shows WAT, kidney, and liver percentages of total body weight in mature adults (n=5). Ing, inguinal fat, p<0.0001; Epi, epididymal fat, p<0.0001; liver, p=0.72. Asterisks, p<0.01 (two-tailed t-test); and 9D shows body weights of Mx1-Cre$^+$, SirT1$^{co/co}$ mice and Mx1-Cre-, SirT1$^{co/co}$ control littermates after pI-pC injection at a pre-puberty age; and 9E shows ratios of food intake versus body weight. Error bars represent s.d.

Prior to this physiological switch, systemic SirT1 plays a dominant role in the control of body growth. As shown in FIG. 9*a*-9*c*, mice without systemic SirT1 (e.g. SirT1$^{co/co}$ mice) maintained a reduced but relatively stable body weight throughout their adult lifespan, while displaying disproportionately reduced WAT. In contrast, their control littermates underwent age-related increases and declines in body weight. To delineate the role of systemic SirT1 in postnatal growth, Mx1-Cre, SirT1$^{co/co}$ mice were generated to temporally regulate SirT1 activity in multiple tissues, including the liver. When the expression of the Mx1-Cre transgene was induced at a pre-puberty age, Mx1-Cre$^+$, SirT1$^{co/co}$ mice not only bypassed the perinatal lethality observed in SirT1$^{ko/ko}$ mice but also displayed reduced body weight through postnatal growth (FIG. 9*d*, FIG. 10). These findings demonstrated that the role of systemic SirT1 in control of body growth is independent of its role for postnatal survival. Loss of hepatocyte SirT1 in these mice may attenuate postnatal growth because hepatocyte-specific SirT1 knockout mice also display delayed postnatal growth (Chen, D. et al., *Genes Dev* 22, 1753-7 (2008)). In contrast, loss of adipocyte SirT1 in AKO-SIRT1 mice had little effect on the body growth prior to the physiological switch (FIG. 8*a*). Collectively, these data reveal the age-dependent roles of SirT1 in control of body weight.

Example 3

The Effects of Systemic and Local Sirt1 on Control of Body Weight

Under ad libitum feeding conditions, mice usually eat an amount of food that is determined by their energy requirements. However, adult SirT1$^{ko/ko}$ mice consumed the same amount of food as their control littermates did, thereby maintaining an elevated ratio of food intake versus body weight (FIG. 9*e*). Not intending to be limited by the theory, it is believed that this phenotype could result from deregulated expression of genes implicated in control of food intake in the hypothalamus, such as Enpp1 and Npy. Interestingly, both Enpp1 and Npy were deregulated in WAT of AKOSIRT1 mice (see microarray analysis below). Increased appetite could also result from the indirect effect of SirT1 deficiency on the efficacy of the growth hormone (GH)-IGF-1 signaling axis, which controls almost half of body growth (Baserga, R., *Eur J Cancer* 40, 2013-5 (2004)). Alternatively, systemic SirT1 may exert pleiotropic effects on the age-dependent control of WAT mass and body weight. A deficiency in Ghrelin, which is a gut-derived circulating hormone that stimulates food intake via Npy-containing neurons and mediates the release of GH (Morton, G. J. et al., *Nature* 443, 289-95 (2006)), does not affect postnatal body growth in mice (Sun, Y. et al., *Mol Cell Biol* 23, 7973-81 (2003); Wortley, K. E. et al., *Proc Nall Acad Sci USA* 101, 8227-32 (2004)). As a result, loss of systemic SirT1 could alter the balance between the Ghrelin-Npy/GH loop for control of food intake and the GH-IGF-1 axis for control of proportional body growth.

The results described above indicated that adipocyte SirT1 mediates fat storage in postmitotic mature adipocytes, resulting in diet-induced weight gain in mature adults. It was observed that interfering with SirT1 activity at different ages and/or in specific tissues produces different biological effects. The growth of white adipose tissue (WAT) was accelerated in young AKOSIRT1 mice (FIG. 1*a*). As mice age, WAT percentage in total body weight increased, but the difference between AKOSIRT1 and control littermates was diminished in mature adult mice (FIG. 1*b*). This age-dependent phenotype reveals that adipocytic SirT1 negatively modulates WAT growth during postnatal growth period. In humans, adipocytes increase in size rather than in numbers in both non-obese and obese adult individuals (Prins, J. B. & O'Rahilly, *Clin Sci (Loud)* 92, 3-11 (1997)). The dynamic turnover of adipocytes occurs at approximately 20 years of age (Spalding, K. L. et al., *Nature* 453, 783-7 (2008)), which coincides with the completion of body growth. In the research for the current disclosure, it was found that a modest fat diet accelerates postnatal body growth in mice, such that the physiological switch occurs earlier at 8 months of age corresponding to approximately 30 years of age in humans, suggesting that adipocyte SirT1 mediates control of body weight after reaching normal weight limit. In parallel to the physiological changes at the ages of sexual maturity and body growth, this physiological change marks the beginning of adulthood in mice, which differs from the common practice of using sexual maturity at 7 to 8 weeks of age. Accordingly, reducing the activity of adipocyte SirT1 is a novel therapeutic strategy for treating or preventing obesity in mature adults.

Figure 12:
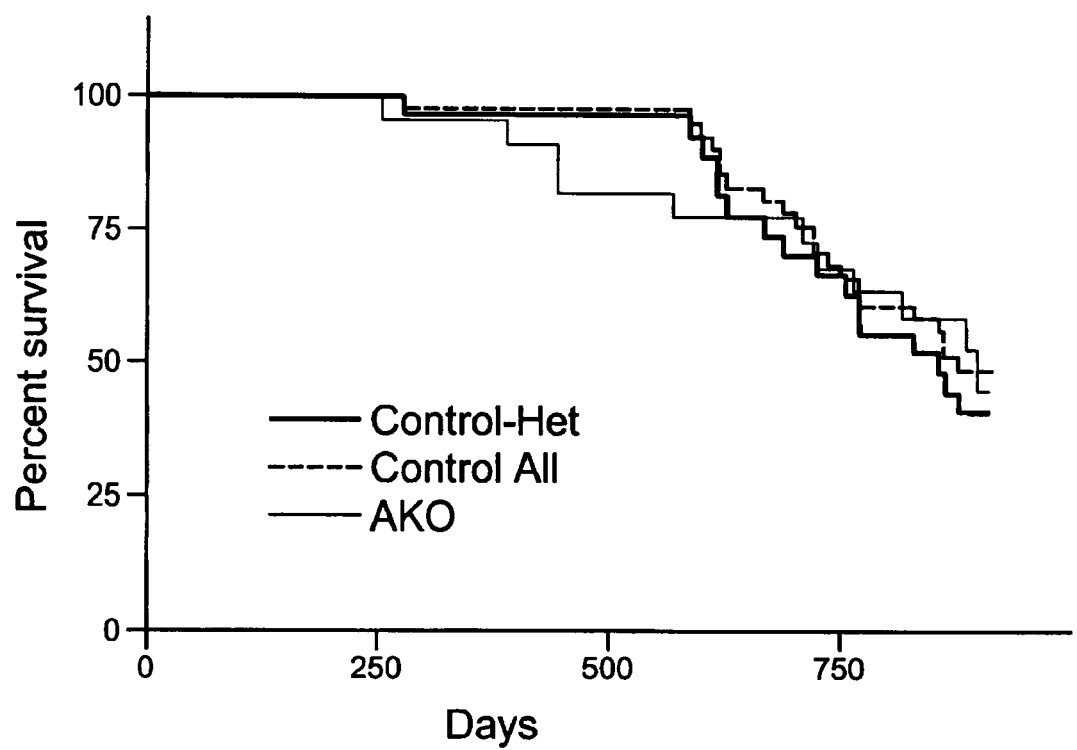
FIG. 12 shows that the mean lifespan of AKOSIRT1 mice was 28 months of age, which is similar to that of littermate control mice when both groups of mice fed normal diet. Three of 15 AKOSIRT1 mice were subjected to euthanasia due to the onset of dermatitis.
Figure 13:
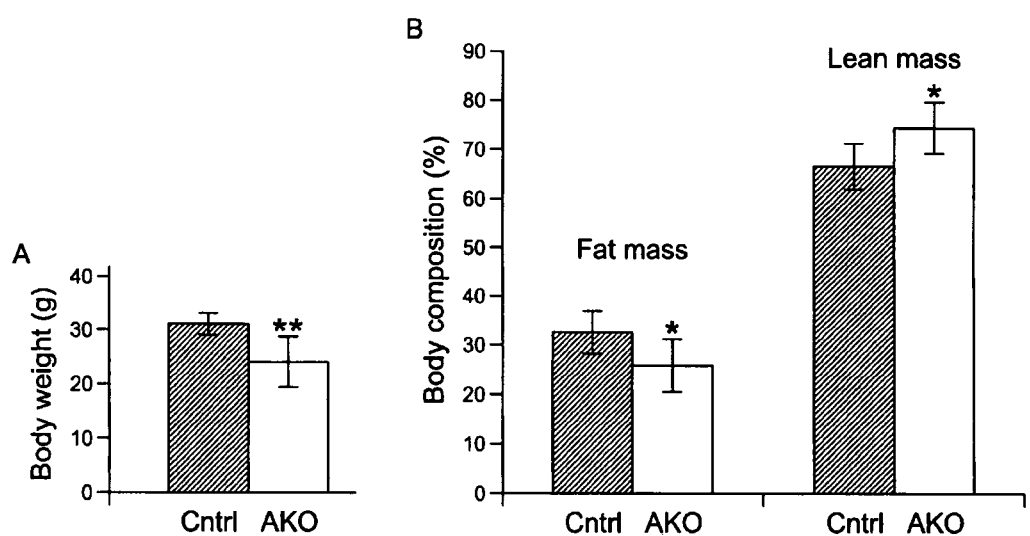
FIG. 13 shows the body composition at 30 months of age using quantitative magnetic resonance (QMR) methods on live mice. 13A shows that AKOSIRT1 mice display lower body weight as compared to littermate control mice (p<0.01, two-tailed t-test); and 13B shows the composition of fat and lean mass, as measured by MRI imaging, has revealed that AKOSIRT1 mice are leaner than their littermate control mice (fat mass: p<0.05; lean mass: p<0.05; two-tailed t-test).
Figure 14:
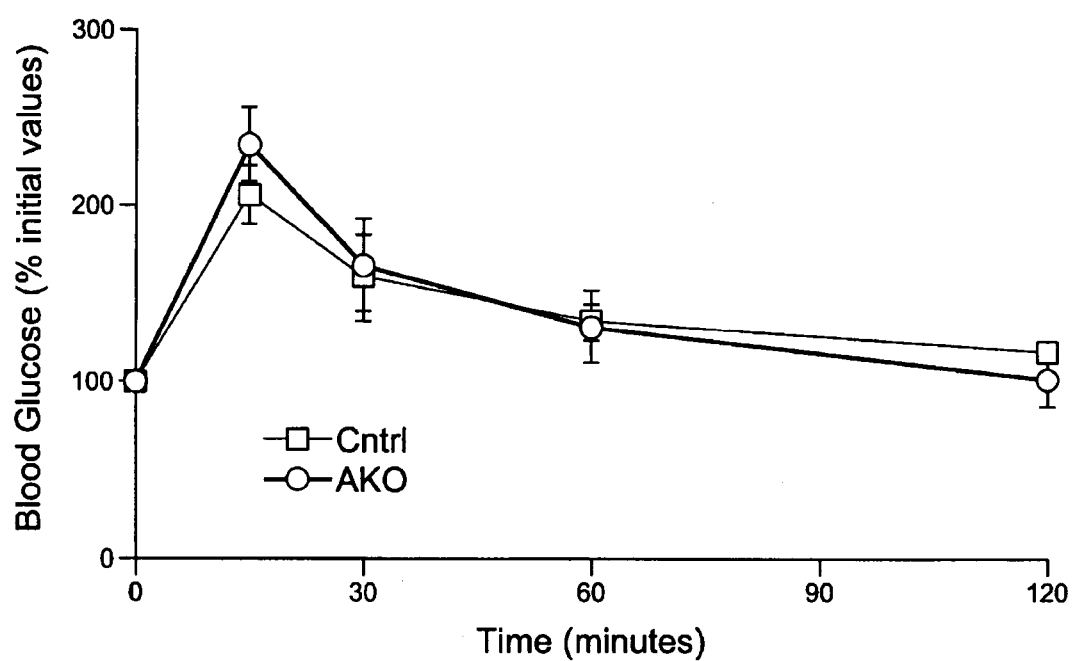
FIG. 14 shows that AKOSIRT1 mice display normal glycemic control at 30 months of age. As measured by using a standard glucose tolerance test, both AKOSIRT1 mice and their littermate control mice have been fasting overnight and the change of serum glucose levels is determined after the administration of glucose.

To evaluate potential adverse effects from the decreased activity of adipocyte SirT1 protein, the life span, body lean mass, and glucose tolerance were measured in AKOSIRT1 mice and compared to control mice. When fed normal fat diet, the mean lifespan of AKOSIRT1 mice were similar to that of littermate control mice (FIG. 12). At 30 months of age, which is beyond the mean lifespan, AKOSIRT1 mice were still leaner and had lower body weight as compared to their littermate control mice (FIGS. 13*a* and 13*b*). In addition, the AKOSIRT1 mice displayed their ability for normal glycemic control as shown by the glucose tolerance test (FIG. 14). These findings suggest that lowering SirT1 activity in adipocytes through adulthood may provide the benefit of health aging, such as leaner body composition and lower body weight, and may not cause insulin resistance while fed normal fat diet. In this context, these findings further confirm that lowering SirT1 activity in adipocytes in adult animals has the benefit of preventing fat diet-induced weight gain.

Example 4

Identification of Genes Whose Expression was Modulated by Sirt1 Activity in Adipocytes The expression of multiple genes may be affected by SirT1 deacetylase. SirT1 deacetylase uses NAD as its co-factor to modify a number of transcription factors, many of which have been implicated in WAT development and function, such as E2F1, PPARγ, PGC-1α, and FOXO1 (Imai, S. et al., *Nature*, 403:795-800 (2000); Picard, F. et al., *Nature*, 429:771-6 (2004); Rodgers, J. T. et al., *Nature*, 434:113-8 (2005); Qiao, L. & Shao, J., *J. Biol Chem*, 281:39915-24 (2006)). Using the Illumina BeadArray platform representing approximately 34,000 mouse genes, genome-wide microarray analysis was performed to identify the genes and pathways modulated by adipocytic SirT1. WAT and liver of control mice displayed age-dependent and tissue-specific gene expression, respectively. When compared to controls, the expression of 311 genes was significantly deregulated in WAT of young AKO-SIRT1 mice (FIG. 2). In comparison, only 64 and 77 genes were differentially expressed in WAT of adult AKOSIRT1 mice and liver of adult) SirT1-deficient)(SirT1$^{ko/ko}$) mice, respectively (FIGS. 3 and 4). Hierarchical clustering of 311 genes using the Euclidean distance metric and the Centroid linkage method identified distinct age- and tissue-dependent gene-expression fingerprints. Noteworthy, the majority of differentially expressed genes did not overlap with the genes whose expression is age-specific and/or tissue-specific (Supplementary FIG. 1), and only a small set of deregulated genes were commonly affected by SirT1 in WAT and liver of adult mice.

Identified genes were annotated in the gene ontology format followed by pathway analyses. Of 311 genes, 118 genes were assigned to 9 composite interaction networks (FIG. 5). The top-ranking network linked 28 genes centered on NF-kappaB and insulin vertices (data not shown). Others and we have previously shown that SirT1 modulates NF-kappaB activation in vitro (Li, H. et al., *Breast Cancer Res* 9, R1 (2007); Yeung, F. et al., *Embo J* 23, 2369-80 (2004); Chen J. et al., *J. Biol Chem.* 48, 40364-74 (2005)). Interestingly, the NF-kappaB node was enriched in both liver and murine embryonic fibroblasts isolated from SirT1$^{ko/ko}$ mice (Supplementary Table 4 and FIG. 5). However, inter and intra-connecting gene modules were disparate between all tissue and cell types analysed. More importantly, the curated NF-kappaB/insulin interaction network consists of several genes implicated in obesity and associated diseases. For example, Lcn2 encodes an adipokine highly expressed by WAT and liver of a rodent model of obesity (Yan, Q. W. et al., *Diabetes* 56, 2533-40 (2007)). Npy encodes a neuropeptide that normally plays a role in hypothalamus for the control of food intake (Morton, G. J. et al., *Nature* 443, 289-95 (2006)). Enpp1 encodes an insulin receptor inhibitor, whose expression is down-regulated during preadipocyte maturation and up-regulated in patients with type 2 diabetes (Maddux, B. A. et al., *Am J Physiol Endocrinol Metab* 290, E746-9 (2006)). Variants of Enpp1 are linked to increased risk of obesity in children and adults (Meyre, D. et al., *Nat Genet* 37, 863-7 (2005)). Indo (indoleamine 2,3-dioxygenase) converts tryptophan, a dietary amino acid, to niacin (Carlson, L. A., *J Intern Med* 258, 94-114 (2005)). Since niacin (i.e. vitamin B1) is converted to nicotinamide and then NAD$^+$ in vivo, their effects on SirT1 activity may activate a regulatory feedback mechanism. The change of the expression of these genes contributes to the phenotypic change in weight control and associated phenotypes.

To independently evaluate the expression of obesity-related genes in WAT, quantitative real-time PCR was performed on a curated panel of 384 Diabesity genes (FIG. 6). As shown in FIG. 7, twenty-four genes were identified as being up-regulated in WAT from young AKOSIRT1 mice, including IGFBP-1, a known target of SirT1 deficiency in WAT of SirT1$^{ko/ko}$ mice (Li, H. et al., *Breast Cancer Res* 9, R1 (2007)). While many of these genes are normally expressed in either the brain or liver, Enpp1 is one of 4 genes normally expressed in WAT. Together, these results suggest that the deregulation of IGFBP-1 and Enpp1 expression could attenuate the efficacy of IGF-1 and insulin signaling. The analysis of SirT1 regulated gene expression as described above has identified the potential for treating or preventing obesity at different age group. Specific examples that may be used as potential targets for treating or preventing obesity include LCN, ENPP1, and INDO.

Although the foregoing disclosure has been described in some detail by way of illustration and example for purposes of clarity of understanding, it will be readily apparent to one of ordinary skill in the art in light of the teachings of this disclosure that certain changes and modifications may be made thereto without departing from the spirit or scope of the appended claims.

What is claimed is:

1. A method for treating or preventing obesity in a subject, the method comprising reducing the activity of a sirtuin 1 (SirT1) deacetylase protein in the subject.

2. The method of claim 1, wherein the step of reducing the activity of a SirT1 deacetylase protein comprises deleting at least partially the gene encoding the SirT1 deacetylase protein.

3. The method of claim 2, wherein deleting at least partially the gene encoding the SirT1 deacetylase protein comprises in-frame deletion of at least partially the gene.

4. The method of claim 3, wherein the in-frame deletion comprises the deletion of exon 4 of the gene.

5. The method of claim 1, wherein the SirT1 deacetylase protein comprises a Sir2 deacetylase domain, and wherein the step of reducing the activity of the SirT1 deacetylase protein comprises introducing at least one mutation into the sequence encoding the Sir2 deacetylase domain, such that the activity of the SirT1 deacetylate protein is reduced.

6. The method of claim 1, wherein the step of reducing the activity of the SirT1 deacetylace protein comprises reducing the expression of the gene encoding the SirT1 deacetylase protein.

7. The method of claim 6, wherein reducing the expression of the gene comprises RNA interference using a SirT1 specific siRNA or miRNA.

8. The method of claim 1, wherein the step of reducing the activity of the SirT1 deacetylase protein comprises contacting an inhibitor with the SirT1 deacetylase protein, such that the activity of the protein is reduced.

9. The method of claim 8, wherein the inhibitor is a sirtuin inhibitor.

10. The method of claim 9, wherein the sirtuin inhibitor is a member selected from a group consisting of:

1,2-dihydro-3H-naphtho[2,1-b]pyran-3-one, 8-bromo-2-phenylsplitomicin, and derivatives thereof, 2-[[(2-hydroxy-1-naphthalenyl)methylene]amino]-N-(1-phen ylethyl) benzamide, and derivatives thereof, 5-(2-hydroxynaphthalen-1-ylmethyl)-6-phenyl-2-thioxo-2,3-dihydro-1H-pyrimidin-4-one, tetrahydro-5-[(2-hydroxy-1-naphthalenyl)methyl]-6-phenyl-2-thioxo-4 (1H)-pyrimidinone, 5-[(2-hydroxy-1-naphthyl) methyl]-2-mercapto-6-phenyl-4(3H)-pyrimidin-one, 6-(4'-Bromophenyl)-5-[2''-hydroxynaphthyl-(1'')-methyl]-2-thioxo-2,3-dihydro-1H-pyrimidin-4-one, and derivatives thereof, 6-chloro-2,3,4,9-tetrahydro-1H-carbazole-1-carboxamide, and indole derivatives thereof, N-[[[4-(Acetylamino)phenyl]amino]thioxomethyl]-4-(1,1-dimethylethyl)benzamide, N-[[[4-[[5-(dimethylamino)-1-oxopentyl]amino]phenyl]amino]thioxomethyl]-4-(1,1-dimethylethyl)-benzamide, and tenovin derivatives thereof, 3-[[3-(4-tert-butylphenyl)1,2,4-oxadiazole-5-carbonyl] amino]-1-[3-(trifluoromethyl) phenyl]thiourea, and oxadiazole-carbonylaminothioureas derivatives thereof, 3,2',3',4'-tetrahydroxychalcone, chalcone polyphenols, and derivatives thereof, 1-benzopyran-2-one, 3,4-dihydrocoumarin, and coumarin derivatives thereof, N-(5-chinolyl)propenamide, and derivatives thereof, suramin, and derivatives thereof, bis(indolyl)maleinimide, and derivatives thereof, nicotinamide, benzamide, 2-anilinobenzamide, and derivatives thereof, N,N-bisbenzyliden-1,4-diamine, and derivatives thereof, anthrachinone, and derivatives thereof, N-(3-phenylpropenoyl)-glycine tryptamide, and derivatives thereof, aristoforin, and derivatives thereof, and thiobarbiturates, and derivatives thereof.

11. The method of claim 1, wherein reducing the activity of the SirT1 deacetylase protein prevents weight gain in the subject.

12. The method of claim 1, wherein reducing the activity of the SirT1 deacetylase protein reduces weight gain in the subject.

13. The method of claim 1, wherein reducing the activity of the SirT1 deacetylase protein reduces weight of the subject.

14. A method of treating or preventing obesity in a subject, the method comprising the step of administering an inhibitor of a sirtuin 1 (SirT1) deacetylase protein to the subject.

15. The method of claim 14, wherein the inhibitor is a siRNA molecule, a miRNA molecule, a small molecule, an antisense molecule, a peptide, or a protein.

16. The method of claim 14, wherein the inhibitor is a member selected from the group consisting of:
- 1,2-dihydro-3H-naphtho[2,1-b]pyran-3-one, 8-bromo-2-phenylsplitomicin, and derivatives thereof,
- 2-[[(2-hydroxy-1-naphthalenyl)methylene]amino]-N-(1-phenylethyl) benzamide, and derivatives thereof,
- 5-(2-hydroxynaphthalen-1-ylmethyl)-6-phenyl-2-thioxo-2,3-dihydro-1H-pyrimidin-4-one, tetrahydro-5-[(2-hydroxy-1-naphthalenyl)methyl]-6-phenyl-2-thioxo-4(1H)-pyrimidinone, 5-[(2-hydroxy-1-naphthyl)methyl]-2-mercapto-6-phenyl-4(3H)-pyrimidin-one, 6-(4'-Bromophenyl)-5-[2"-hydroxynaphthyl-(1")-methyl]-2-thioxo-2,3-dihydro-1H-pyrimidin-4-one, and derivatives thereof,
- 6-chloro-2,3,4,9-tetrahydro-1H-carbazole-1-carboxamide, and indole derivatives thereof,
- N-[[[4-(Acetylamino)phenyl]amino]thioxomethyl]-4-(1,1-dimethylethyl)benzamide, N-[[[4-[[5-(dimethylamino)-1-oxopentyl]amino]phenyl]amino]thioxomethyl]-4-(1,1-dimethylethyl)-benzamide, and tenovin derivatives thereof,
- 3-[[3-(4-tert-butylphenyl)1,2,4-oxadiazole-5-carbonyl]amino]-1-[3-(trifluoromethyl) phenyl]thiourea, and oxadiazole-carbonylaminothioureas derivatives thereof,
- 3,2',3',4'-tetrahydroxychalcone, chalcone polyphenols, and derivatives thereof,
- 1-benzopyran-2-one, 3,4-dihydrocoumarin, and coumarin derivatives thereof,
- N-(5-chinolyl)propenamide, and derivatives thereof,
- suramin, and derivatives thereof,
- bis(indolyl)maleinimide, and derivatives thereof,
- nicotinamide, benzamide, 2-anilinobenzamide, and derivatives thereof,
- N,N-bisbenzyliden-1,4-diamine, and derivatives thereof,
- anthrachinone, and derivatives thereof,
- N-(3-phenylpropenoyl)-glycine tryptamide, and derivatives thereof,
- aristoforin, and derivatives thereof, and
- thiobarbiturates, and derivatives thereof.

17. The method of claim 14, wherein the subject is an adult human.

18. The method of claim 14, wherein the inhibitor is an antibody.

* * * * *

SEQUENCE LISTING

```
<160> NUMBER OF SEQ ID NOS: 3

<210> SEQ ID NO 1
<211> LENGTH: 21
<212> TYPE: DNA
<213> ORGANISM: Unknown
<220> FEATURE:
<223> OTHER INFORMATION: PCR primer for identifying co loci of the SirT1
      gene, as shown on page 39, line 16 of the application

<400> SEQUENCE: 1
ggttgactta ggtcttgtct g                                           21

<210> SEQ ID NO 2
```

```
<211> LENGTH: 20
<212> TYPE: DNA
<213> ORGANISM: Unknown
<220> FEATURE:
<223> OTHER INFORMATION: PCR primer for identifying ko loci of the SirT1
      gene, as shown on page 39, line 17 of the application

<400> SEQUENCE: 2
aggcggattt ctgagttcga                                              20

<210> SEQ ID NO 3
<211> LENGTH: 20
<212> TYPE: DNA
<213> ORGANISM: Unknown
<220> FEATURE:
<223> OTHER INFORMATION: PCR primer for identifying the SirT1 gene, as
      shown on page 39, line 17 of the application

<400> SEQUENCE: 3
cgtcccttgt aatgtttccc                                              20
```